(12) United States Patent
Aebi et al.

(10) Patent No.: US 7,977,358 B2
(45) Date of Patent: Jul. 12, 2011

(54) PYRAZOL DERIVATIVES

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/173,847

(22) Filed: Jul. 16, 2008

(65) Prior Publication Data
US 2009/0029963 A1 Jan. 29, 2009

(30) Foreign Application Priority Data
Jul. 26, 2007 (EP) .................... 07113173

(51) Int. Cl.
A61K 31/454 (2006.01)
C07D 401/14 (2006.01)
(52) U.S. Cl. .................. 514/326; 546/211
(58) Field of Classification Search .......... 514/210.2, 514/218, 253.09, 236.5; 540/575; 544/364, 544/130; 546/211
See application file for complete search history.

(56) References Cited

U.S. PATENT DOCUMENTS

| 5,134,142 | A | 7/1992 | Matsuo et al. |
| 2004/0220170 | A1 | 11/2004 | Atkinson et al. |
| 2005/0020564 | A1 | 1/2005 | Atkinson et al. |
| 2005/0176703 | A1 | 8/2005 | Gabriel et al. |
| 2005/0192302 | A1 | 9/2005 | Xue et al. |
| 2006/0058351 | A1* | 3/2006 | Diaz et al. .......... 514/317 |
| 2006/0264419 | A1 | 11/2006 | Schiemann et al. |
| 2007/0015784 | A1 | 1/2007 | Sundermann et al. |

FOREIGN PATENT DOCUMENTS

| DE | 101 49 370 | 4/2003 |
| DE | 103 15 572 | 10/2004 |
| DE | 10 2004 014 296 | 10/2005 |
| DE | 10 2005 030 051 | 12/2006 |
| EP | 1762568 | 3/2007 |
| JP | 61040266 | 2/1986 |
| WO | WO 99/05823 | 11/1999 |
| WO | WO 03/004480 | 1/2003 |
| WO | WO 03/037274 | 5/2003 |
| WO | WO 03/093266 | 11/2003 |
| WO | WO 2004/047776 | 6/2004 |
| WO | WO 2005/101989 | 11/2005 |
| WO | WO 2006/089076 | 8/2006 |
| WO | WO 2007/008541 | 1/2007 |
| WO | WO 2008/075019 | 6/2008 |

OTHER PUBLICATIONS

Wolff et al., Burger's Medicinal Chemistry and Drug Discovery, 1994, Wiley-Interscience, Fifth Edition, vol. I: Principles and Practice, pp. 975-977.*
Witte et al., J. Org. Chem., 37, pp. 2849-2853 (1972).
Richter, R., Helvetica Chimica Acta, 35, pp. 478-485 (1952).
Jung, J., Tetrahedron, 58, pp. 3639-3646 (2002).
Stara et al., Collect. Czech. Chem. Commun., 64, pp. 649-672 (1999).
Tanaka et al., Bull. Chem. Soc. Jpn., 59, pp. 2631-2632 (1986).
Shawali et al., Tetrahedron, 29, pp. 121-124 (1973).
Mann et al., Synthesis, pp. 331-333 (1985).
Guzman-Perez et al., Bioorg. Med. Chem. Lett., 11, pp. 803-807 (2001).
Bouzard et al., J. Med. Chem., 33, pp. 1344-1352 (1990).
Rosen et al., J. Med. Chem., 31, pp. 1598-1611 (1988).
Mitsumori et al., J. Am. Chem. Soc. 129, pp. 1040-1041 (2006).
Huang et al., Tetrahedron, 54, pp. 1254712560 (1998).
Zhao et al., Heterocycles, 39, pp. 163-170 (1994).
Wysong et al., J. Org. Chem., 61, pp. 7650-7651 (1996).
Smith et al., J. Med. Chem., 38, pp. 3772-3779 (1995).
Ksander et al., J. Org. Chem., 42, pp. 1180-1185 (1977).
Machetti et al., Tetrahedron, 57, pp. 4995-4498 (2001).
Tamaki et al., J. Org. Chem., 66, pp. 3593-3596 (2001).
Taylor et al., Tetrahedron Lett., 37, pp. 1297-1300 (1996).
Palazzino et al., II Farmaco—Ed. Sc., 41, pp. 566-576 (1986).

* cited by examiner

*Primary Examiner* — Kamal A Saeed
*Assistant Examiner* — Kristin Bianchi
(74) *Attorney, Agent, or Firm* — George W. Johnston; Patricia S. Rocha-Tramaloni

(57) ABSTRACT

The invention is concerned with novel pyrazol derivatives of formula (I),

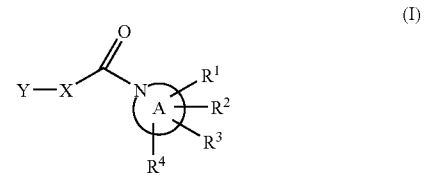

wherein

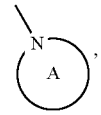

$R^1$, $R^2$, $R^3$, $R^4$, X and Y are as defined herein, as well as physiologically acceptable salts thereof. These compounds are antagonists of CCR-2 receptor and/or CCR-5 receptor and can be used as medicaments.

17 Claims, No Drawings

PYRAZOL DERIVATIVES

PRIORITY TO RELATED APPLICATION(S)

This application claims the benefit of European Patent Application No. 07113173.4, filed Jul. 26, 2007, which is hereby incorporated by reference in its entirety.

BACKGROUND OF THE INVENTION

The compounds of formula (I) are CCR2 receptor (Chemokine Receptor 2/Monocyte chemotactic protein 1 receptor) antagonists and also CCR5 receptor (Chemokine Receptor 5). Chemokines are a family of small, secreted proinflammatory cytokines functioning as chemoattractants for leukocytes. They promote trafficking of leukocytes in response to inflammatory or homeostatic signals. Chemokine orchestrate directed migration from and to vascular beds into lymphoid and peripheral tissues by establishing chemotactic gradients and activation of adhesion molecules. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Monocyte Chemotactic protein 1 (CCL2) is considered to be a major chemokine mediating inflammatory processes in these diseases through the CCR2 receptor on different leukocyte subsets, in particular monocytes. In particular CCR2 and its ligands are considered to be involved in the development of atherosclerosis, peripheral vascular diseases and critical limb ischemia. There is a large body of information from animal models of MCP-1 and CCR2 ko mice in wt or apoE-/- or LDL-R-/- backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

CCR2 is also important in diseases with inflammatory components like rheumatoid arthritis, asthma, multiple sclerosis, transplant rejection and ischemia reperfusion injury with specific prominent effects in nephropathy and peripheral vascular diseases. In addition preclinical data suggest CCR2 and its ligands are involved in the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of the before mentioned diseases. The present invention provides the novel compounds of formula (I) which are CCR2 receptor antagonists, with some antagonist activity also at CCR5.

SUMMARY OF THE INVENTION

The present invention relates to novel pyrazol derivatives of formula (I),

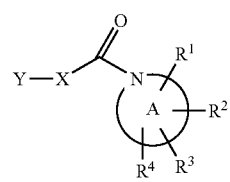

wherein

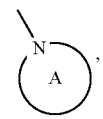

$R^1$, $R^2$, $R^3$, $R^4$, X and Y are as defined herein, as well as physiologically acceptable salts thereof.

DETAILED DESCRIPTION OF THE INVENTION

The invention is concerned with novel pyrazol derivatives of formula (I),

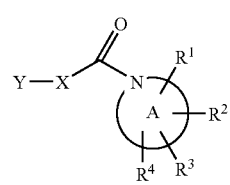

, wherein

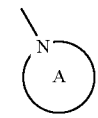

is a non-aromatic mono-cyclic radical of four to eight ring atoms, in which one or two ring atoms are nitrogen atoms with the remaining ring atoms being carbon atoms;

provided that, when

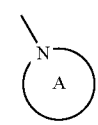

contains the second ring nitrogen atom, said ring nitrogen atom is not directly bonded to another heteroatom or to a carbonyl group;

X is

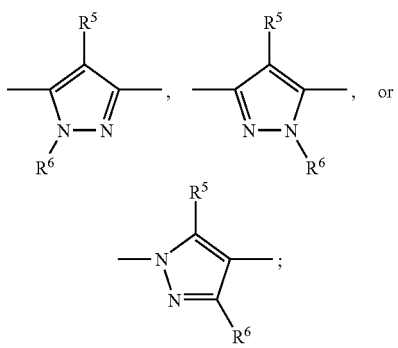

Y is phenyl or heteroaryl, said heteroaryl being an aromatic mono-cyclic radical of six ring atoms, in which one or two ring atoms are nitrogen atoms, the remaining ring atoms being carbon atoms, and said phenyl and said heteroaryl being substituted by one, two or three substituents independently selected from the group consisting of $C_{1-8}$ alkyl, halo $C_{1-6}$ alkyl, $C_{1-6}$ alkoxy, halo $C_{1-6}$ alkyoxy, halogen, cyano, optionally substituted phenyl, optionally substituted heteroaryl, optionally substituted $C_{3-7}$ cycloalkyl, optionally substituted heterocyclyl, $C_{1-6}$ alkylvinyl, halo $C_{1-6}$ alkylvinyl, optionally substituted $C_{3-7}$ cycloalkylvinyl, optionally substituted heterocyclylvinyl, optionally substituted phenylvinyl, optionally substituted heteroarylvinyl, $C_{1-6}$ alkylethynyl, halo $C_{1-6}$ alkylethynyl, optionally substituted $C_{3-7}$ cycloalkylethynyl, optionally substituted heterocyclylethynyl, optionally substituted phenylethynyl, optionally substituted heteroarylethynyl, $C_{1-6}$ alkylcarbonylamino, halo $C_{1-6}$ alkyl carbonylamino, optionally substituted $C_{3-7}$ cycloalkylcarbonylamino, optionally substituted heterocyclylcarbonylamino, optionally substituted phenylcarbonylamino and optionally substituted heteroarylcarbonylamino;

$R^1$, $R^2$, $R^3$ and $R^4$ are, when attached to a ring carbon atom, independently are selected from the group consisting of hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, halogen, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl or amino optionally substituted by one or two substituents independently selected from $C_{1-6}$ alkyl, acyl, heteroalkyl, optionally substituted $C_{3-7}$ cycloalkyl or optionally substituted heterocyclyl, and optionally substituted heterocyclyl, in which one of the ring carbon atoms of the heterocyclyl may be a ring carbon atom of another ring which is $C_{3-7}$ cycloalkyl or heterocyclyl, one or two ring carbon atoms of said another ring being optionally replaced by a carbonyl group; and when two of $R^1$, $R^2$, $R^3$ and $R^4$ are attached to the same ring carbon atom, they can, together with the carbon atom to which they are attached, form a $C_{3-7}$ cycloalkyl ring or heterocyclyl ring; or when attached to a ring nitrogen atom, $R^1$, $R^2$, $R^3$ and $R^4$ are independently hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl, optionally substituted $C_{3-7}$ cycloalkyl $C_{1-6}$ alkyl, optionally substituted heterocyclyl or optionally substituted heterocyclyl-$C_{1-6}$ alkyl;

$R^5$ is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, trimethylsilanyl $C_{2-6}$ alkenyl, trimethylsilanyl $C_{2-6}$ alkynyl, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenyl-methoxy-$C_{1-6}$ alkyl;

$R^6$ is hydrogen, $C_{1-6}$ alkyl, halo $C_{1-6}$ alkyl, heteroalkyl, $C_{3-7}$ cycloalkyl, $C_{3-7}$ cycloalkyl $C_{1-6}$ alkyl, heteroaryl, optionally substituted heteroaryl or $C_{1-6}$ alkylcarbonylamino $C_{1-4}$ alkyl;

provided that the compounds wherein Y is mono- or di-fluorosubstituted phenyl, mono- or di-methyl substituted phenyl, mono-chloro substituted phenyl, mono-methoxy substituted phenyl, mono-phenyl substituted phenyl, mono-chloro-mono-methyl substituted phenyl, mono-fluoro-mono-methoxy substituted phenyl and mono-chloro substituted pyridyl are excluded; or a prodrug or a pharmaceutically acceptable salt thereof.

Further, the invention is concerned with a process for the manufacture of the above compounds, pharmaceutical preparations which contain such compounds, the use of these compounds for the production of pharmaceutical preparations.

Unless otherwise indicated, the following definitions are set forth to illustrate and define the meaning and scope of the various terms used to describe the invention herein.

The term "heteroatom" means a nitrogen atom, an oxygen atom or a sulphur atom.

The term "halogen" or "halo" means fluorine, chlorine, bromine and iodine, with chlorine and fluorine being preferred.

The term "$C_{1-6}$ alkyl", alone or in combination with other groups, means a branched or straight-chain monovalent alkyl radical, having one to six carbon atoms. The term "$C_{1-8}$ alkyl", alone or in combination with other groups, means a branched or straight-chain monovalent alkyl radical, having one to eight carbon atoms. This term is further exemplified by such radicals as methyl, ethyl, n-propyl, isopropyl, n-butyl, s-butyl, t-butyl, n-hexyl.

The term "halo $C_{1-6}$ alkyl" means $C_{1-6}$ alkyl substituted by one or more same or different halogen atoms.

The term "$C_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "halo $C_{1-6}$ alkoxy", alone or in combination with other groups, means $C_{1-6}$ alkoxy substituted by one or more, preferably one to three halogens.

The term "$C_{2-6}$ alkenyl", alone or in combination with other groups, means a straight-chain or branched hydrocarbon residue comprising a carbon-carbon double bond, having two to six carbon atoms. This term is further exemplified by such radicals as ethenyl, 2-propenyl.

The term "hydroxy $C_{2-6}$ alkenyl" or "$C_{1-6}$ alkoxy $C_{2-6}$ alkenyl" means $C_{2-6}$ alkenyl substituted by one or more, preferably one or two hydroxy groups or $C_{1-6}$ alkoxy groups, respectively; most preferred are hydroxy $C_{3-6}$ alkenyl and $C_{1-6}$ alkoxy $C_{3-6}$ alkenyl groups.

The term "$C_{2-6}$-alkynyl", alone or in combination with other groups, means a straight-chain or branched hydrocarbon residue comprising a carbon-carbon triple bond, having two to six carbon atoms. This term is further exemplified by such radicals as ethynyl, 2-propynyl.

The term "hydroxy $C_{2-6}$ alkynyl" or "$C_{1-6}$ alkoxy $C_{2-6}$ alkenyl" means $C_{2-6}$ alkynyl substituted by one or more, preferably one or two hydroxy groups or $C_{1-6}$ alkoxy groups, respectively; most preferred are hydroxy $C_{3-6}$ alkynyl and $C_{1-6}$ alkoxy $C_{3-6}$ alkynyl groups.

The term "acyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

The term "heteroalkyl" means $C_{1-6}$ alkyl substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heteroalkoxy" means $C_{1-6}$ alkoxy substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heterocyclyl" means non-aromatic mono-cyclic radicals of four to eight ring atoms, in which one to three ring atoms are heteroatoms independently selected from N, O and $S(O)_n$ (where n is an integer from 0 to 2), the remaining ring atoms being C, and one or two of the ring carbon atoms of the heterocyclyl being optionally replaced with a carbonyl group.

The term "heteroaryl" means an aromatic mono- or bi-cyclic radical of five to ten ring atoms, having one to three ring heteroatoms independently selected from N, O, and S, the remaining ring atoms being C.

The term "optionally substituted $C_{3-7}$ cycloalkyl" means $C_{3-7}$ cycloalkyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl and $C_{1-6}$ alkylsulfonyl.

The term "optionally substituted phenyl" means a phenyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl and $C_{1-6}$ alkylsulfonyl.

The term "optionally substituted heterocyclyl" means a heterocyclyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, $C_{1-6}$ alkylcarbonylamino, mono- or di-$C_{1-6}$ alkyl substituted aminocarbonyl, $C_{1-6}$ alkylthio, $C_{1-6}$ alkylsulfinyl and $C_{1-6}$ alkylsulfonyl.

The term "optionally substituted heteroaryl" means a heteroaryl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and —NHCO—$C_{1-6}$ Alkyl.

The term, "$C_{1-6}$ alkylsulfonyl", "$C_{1-6}$ alkylsulfinyl" and "$C_{1-6}$ alkylthio", alone or combination with other groups, means $C_{1-6}$ alkyl-$SO_2$—, $C_{1-6}$ alkyl-SO— and $C_{1-6}$ alkyl-S—, respectively.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compounds of formula (I),

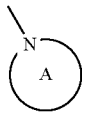

is preferably diazepan-1-yl, piperazin-1-yl, piperidin-1-yl or pyrrolidin-1-yl, more preferably piperidin-1-yl.

ii) In the compounds of formula (1), preferably two of $R^1$, $R^2$, $R^3$ and $R^4$ are hydrogen, and, the other two are, when attached to a ring carbon atom, independently hydrogen, hydroxy, amino optionally substituted by one or two substituents independently selected from the group consisting of $C_{1-6}$ alkyl, heteroalkyl, optionally substituted $C_{3-7}$ cycloalkyl and optionally substituted heterocyclyl or optionally substituted heterocyclyl, in which one of the ring carbon atoms of the heterocyclyl may be a ring carbon atom of another ring which is heterocyclyl, one or two ring carbon atoms of said another ring being optionally replaced by a carbonyl group, and when they are attached to the same ring carbon atom, they can, together with the carbon atom to which they are attached, form heterocyclyl ring, and when attached to a ring nitrogen atom, the other two are independently hydrogen, $C_{1-6}$ alkyl, heteroalkyl, optionally substituted $C_{3-7}$ cycloalkyl or optionally substituted heterocyclyl-$C_{1-6}$ alkyl.

More preferably, three of $R^1$, $R^2$, $R^3$ and $R^4$ are hydrogen, and the other one is attached to a ring carbon atom and optionally substituted heterocyclyl, in which one of the ring carbon atoms of the heterocyclyl may be a ring carbon atom of another ring which is heterocyclyl, one or two ring carbon atoms of said another ring being optionally replaced by a carbonyl group.

Further more preferably, three of $R^1$, $R^2$, $R^3$ and $R^4$ are hydrogen, and the other one is attached to a ring carbon atom and optionally substituted pyrrolidin-1-yl, in which one of the ring carbon atoms of the pyrrolidin-1-yl may be a ring carbon atom of another ring which is heterocyclyl, one or two ring carbon atoms of said another ring being optionally replaced by a carbonyl group. Hydroxy, $C_{1-6}$ alkyl carbonylamino, such as methylcarbonylamino, or hydroxy $C_{1-6}$ alkyl, such as hydroxy methyl, are especially preferred as the substituent of pyrrolidin-1-yl. Unsubstituted pyrrolidin-1-yl is also especially preferred.

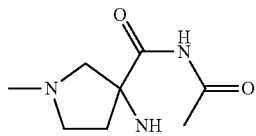

is also preferred as

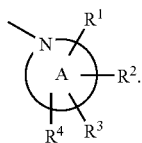

iii) In the compounds of formula (I), X is preferably

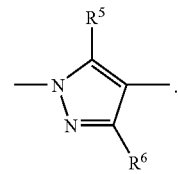

iv) In the compounds of formula (I), $R^5$ is preferably hydrogen, $C_{1-6}$ alkyl, heteroalkyl or optionally substituted $C_{3-7}$ cycloalkyl, more preferably $R^5$ is $C_{1-6}$ alkyl or optionally substituted $C_{3-7}$ cycloalkyl, and $R^5$ is especially methyl or cyclopropyl.

v) In the compounds of formula (I), $R^6$ is preferably hydrogen, $C_{1-6}$ alkyl, heteroalkyl or $C_{3-7}$ cycloalkyl, more preferably $R^6$ is $C_{1-6}$ alkyl, and $R^6$ is especially methyl. Heteroaryl, especially pyridyl or pyrimidinyl is also preferred for $R^6$.

vi) In the compounds of formula (I), Y is preferably phenyl or heteroaryl, which is an aromatic mono-cyclic radical of six ring atoms, in which one or two ring atoms are nitrogen atoms, the remaining ring atoms being carbon atoms, said phenyl and said heteroaryl being substituted by one or two substituents independently selected from the group consisting of $C_{1-8}$ alkyl, halo $C_{1-6}$ alkyl, $C_{1-6}$ alkoxy, halo $C_{1-6}$ alkyoxy, halogen, optionally substituted phenyl, optionally substituted heteroaryl, optionally substituted $C_{3-7}$ cycloalkylvinyl, optionally substituted phenylvinyl, $C_{1-6}$ alkylethynyl, optionally substituted phenylethynyl, halo $C_{1-6}$ alkyl carbonylamino and optionally substituted phenylcarbonylamino. More preferred substituents are one or two substituents independently selected from the group consisting of chloro, halo $C_{1-6}$ alkyl and halo $C_{1-6}$ alkyoxy. Trifluoromethyl or trifluoromethoxy is especially preferred as a substituent.

Preferred heteroaryl as Y is pyridyl or pyrimidinyl, especially pyridyl.

Phenyl or pyridyl, said phenyl and said pyridyl being substituted by one substituent, which is trifluoromethyl or trifluoromethoxy, is especially preferred as Y. Phenyl or pyridyl, said phenyl and said pyridyl being substituted by two chlorines, is also preferred as Y.

vii) Compounds, wherein Y is trifluoromethyl or trifluoromethoxy, $R^5$ is cyclopropyl and $R^6$ is pyridyl, pyrimidinyl or methyl are especially preferred.

viii) A preferred compound of the invention is a compound of formula (I), which is

[3,5-Dimethyl-1-(5-trifluoromethyl-pyridin-3-yl)-1H-pyrazol-4-yl]-(4-pyrrolidin-1-yl-piperidin-1-yl)-methanone,

[5-Cyclopropyl-3-methyl-1-(3-trifluoromethoxy-phenyl)-1H-pyrazol-4-yl]-(4-pyrrolidin-1-yl-piperidin-1-yl)-methanone,

[5-Cyclopropyl-3-methyl-1-(3-trifluoromethyl-phenyl)-1H-pyrazol-4-yl]-(4-pyrrolidin-1-yl-piperidin-1-yl)-methanone,

[5-Cyclopropyl-3-methyl-1-(3-trifluoromethoxy-phenyl)-1H-pyrazol-4-yl]-[4-((S)-2-hydroxymethyl-pyrrolidin-1-yl)-piperidin-1-yl]-methanone, 7-{1-[5-Cyclopropyl-3-methyl-1-(3-trifluoromethoxy-phenyl)-1H-pyrazole-4-carbonyl]-piperidin-4-yl}-1,3,7-triaza-spiro[4.4]nonane-2,4-dione,

[5-Cyclopropyl-3-methyl-1-(3-trifluoromethoxy-phenyl)-1H-pyrazol-4-yl]-[4-((R)-3-hydroxy-pyrrolidin-1-yl)-piperidin-1-yl]-methanone or N—((R)-1-{1-[5-Cyclopropyl-3-methyl-1-(3-trifluoromethoxy-phenyl)-1H-pyrazole-4-carbonyl]-piperidin-4-yl}-pyrrolidin-3-yl)-acetamide,

[5-Cyclopropyl-3-pyridin-4-yl-1-(3-trifluoromethoxy-phenyl)-1H-pyrazol-4-yl]-(4-pyrrolidin-1-yl-piperidin-1-yl)-methanone,

[5-Cyclopropyl-3-pyridin-4-yl-1-(3-trifluoromethoxy-phenyl)-1H-pyrazol-4-yl]-[4-((S)-2-hydroxymethyl-pyrrolidin-1-yl)-piperidin-1-yl]-methanone,

[5-Cyclopropyl-3-pyridin-3-yl-1-(3-trifluoromethyl-phenyl)-1H-pyrazol-4-yl]-(4-pyrrolidin-1-yl-piperidin-1-yl)-methanone,

[5-Cyclopropyl-3-pyridin-4-yl-1-(3-trifluoromethyl-phenyl)-1H-pyrazol-4-yl]-[4-((S)-2-hydroxymethyl-pyrrolidin-1-yl)-piperidin-1-yl]-methanone,

[5-Cyclopropyl-3-pyrimidin-5-yl-1-(4-trifluoromethoxy-phenyl)-1H-pyrazol-4-yl]-(4-pyrrolidin-1-yl-piperidin-1-yl)-methanone,

[5-Cyclopropyl-3-methyl-1-(3-trifluoromethyl-phenyl)-1H-pyrazol-4-yl]-[4-((S)-2-hydroxymethyl-pyrrolidin-1-yl)-piperidin-1-yl]-methanone, N—((R)-1-{1-[5-Cyclopropyl-3-methyl-1-(3-trifluoromethyl-phenyl)-1H-pyrazole-4-carbonyl]-piperidin-4-yl}-pyrrolidin-3-yl)-acetamide, or N-((3R,5S)-1-{1-[5-Cyclopropyl-3-methyl-1-(3-trifluoromethoxy-phenyl)-1H-pyrazole-4-carbonyl]-piperidin-4-yl}-5-hydroxymethyl-pyrrolidin-3-yl)-acetamide.

General Synthetic Procedures

The compounds of formula (I) can be manufactured by methods known in the art, by the methods given below, by the methods given in the examples or by analogous methods. Appropriate reaction conditions for the individual reaction steps are known to a person skilled in the art. Starting materials are either commercially available or are known or can be prepared by methods given below, by methods described in references cited in the text or by methods described in the examples, or by methods known in the art. The syntheses of the compounds of formula (I) are described in scheme 3 and 4. Schemes 1 and 2 describe the synthesis of intermediates.

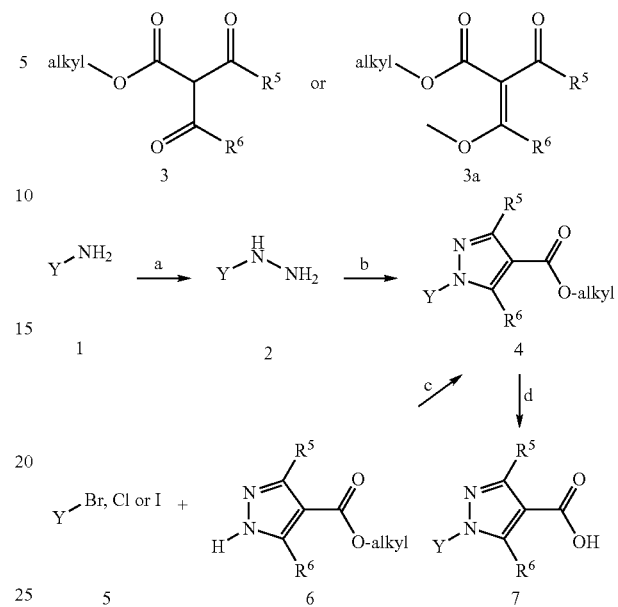

Scheme 1

(In Scheme 1, $R^5$, $R^6$ and Y are as defined before, and alkyl means $C_{1-6}$ alkyl.)

Anilines 1 (scheme 1) are known or can be prepared by methods known in the art, e.g. anilines are available by reduction of the corresponding nitro compound, anilines with substituents equal to an alk-1-ynyl group can be prepared from aniline carrying bromo or iodo functions by reaction with an alk-1-yne under Sonogashira reaction conditions: treatment with copper (I) iodide and tetrakis-(triphenylphosphine)-palladium(0) in piperidine between room temperature and about 100° C. Optionally any substituent present in anilines 1 can be modified at any state of the synthesis, e.g. by hydrogenation of a double or a triple bond to a single bond. Hydrazines 2 are known or can be prepared from anilines 1 by following e.g. the procedure described in Witte, John; Boeketheide, V. Journal of Organic Chemistry (1972), 37(18), 2849-53, with sodium nitrite followed by reduction with tin(II) chloride in 25% aqueous hydrochloric acid at 0° C. to RT (step a). Pyrazoles 4 can then be synthesized beginning with hydrazines 2 and beta-diketo esters 3 in aqueous acetic acid e.g. in analogy to Richter, Rob. Helvetica Chimica Acta (1952), 35, 478-85 (step b). Beta-diketo esters 3 are commercially available or can be synthesized from reaction of the beta-keto ester with the corresponding acid chloride in the presence of anhydrous magnesium chloride and pyridine in $CH_2Cl_2$ at 2° C. to RT or using iPrMgCl in THF at 0° C.

Alternatively beta-diketoesters 3 can be transformed into the methyl enolethers 3a with caesium carbonate and methyl trifluoromethanesulfonate in MeCN at 2° C. to RT and can then be reacted with hydrazines 2 optionally as HCl salt in a solvent like MeOH in the presence of $Et_3N$ at −20° C. up to RT to give pyrazoles 4. Pyrazoles 4 can also be prepared with pyrazoles 6 synthesized as described in J Jung. Tetrahedron (2002), 58, (18), 3639-3639 and then subsequently coupled with bromo or iodo or chloro (in the case of heteroaryl) compounds 5 in the presence of copper iodide and cesium carbonate in DMA at 100 to 160° C. (step c).

Hydrolysis of the esters 4 with aqueous NaOH in DMSO or alcoholic solvent at RT to 40° C. gave acids 7 (step d).

Scheme 2

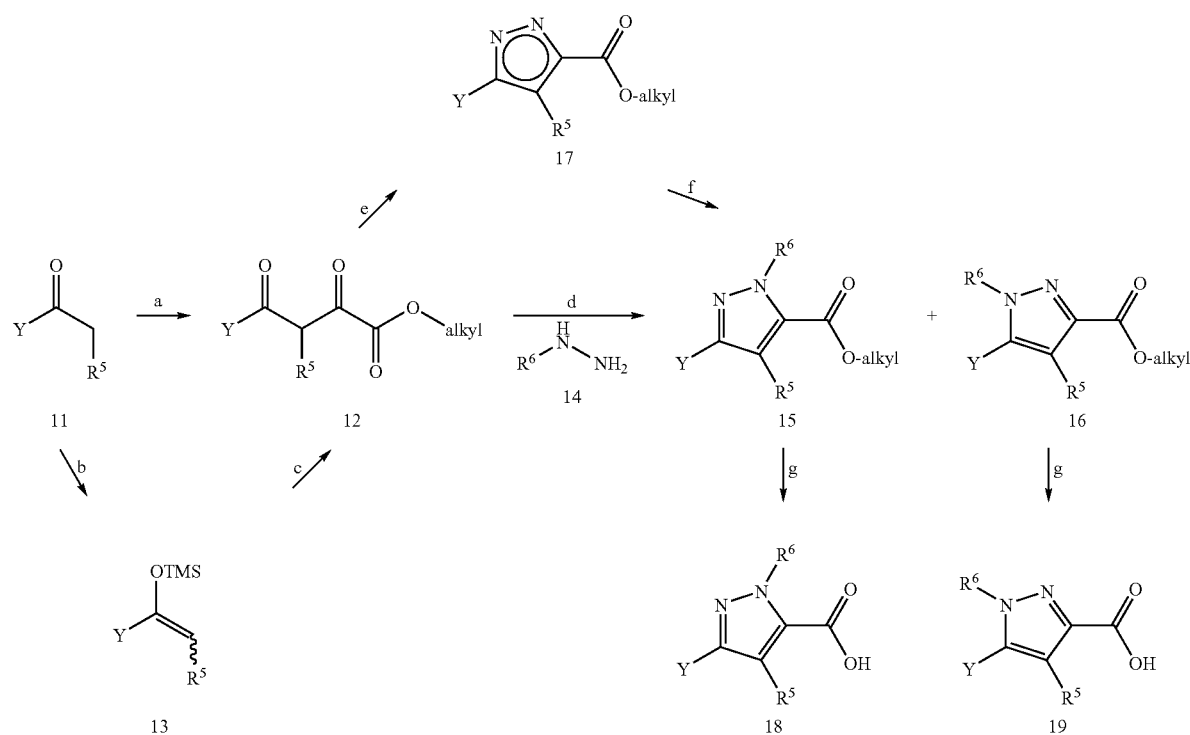

(In Scheme 2, $R^5$, $R^6$ and Y are as defined before, and alkyl means $C_{1-6}$ alkyl.)

Substituted acetophenones and heteroaryl ketones 11 are commercially available, known or can be prepared by methods known in the art (scheme 2). Acylation of compounds 11 with oxalate derivatives can be performed under standard conditions, e.g. with diethyl oxalate in the presence of a base like sodium ethoxide at temperatures between −78° C. and 50° C. in solvents like ethanol, or with lithium hexamethyldisilazide at temperatures between −78° C. and ambient temperature in solvents like ether, to form after subsequent acidification free ethyl pyruvates 12 (step a). Alternatively, pyruvates 12 can be synthesized via i) transforming ketones 11 into the corresponding silyl enol ethers 13, e.g. through treatment with trimethylsilyl chloride in the presence of a base like triethylamine at temperatures between 0° C. and 40° C. in a solvent like acetonitrile (step b) and ii) in situ formation of a metal enol ether, e.g. with zinc chloride and subsequent acylation with an acylation reagent like ethyl oxalyl chloride at temperatures between 0° C. and 50° C. in a solvent like toluene or dichloromethane (step c). Pyruvates 12 can be converted to regioisomeric pyrazoles 15 and 16 through condensation with hydrazines $H_2NNHR^6$ 14 which are commercially available, known or can be prepared by methods known in the art, e.g. at temperatures between ambient temperature and then reflux temperature of the solvent in solvents like ethanol (step d). Alternatively, pyrazoles 15 and 16 can be synthesized via i) reacting pyruvates 12 with hydrazine, preferably at reflux temperature in ethanol (step e) and ii) conversion of the obtained pyrazoles 17 into regioisomeres 15 and 16 under standard conditions, e.g. through 1 alkylation with an alkyl halogenide in the presence of a base like potassium hydroxide at temperatures between 20° C. and the reflux temperature of the solvent in solvents like ethanol (step f).

Regioisomeric pyrazoles 15 and 16 can easily be separated by standard techniques, e.g. through column chromatography on silica. Hydrolysis of esters 15 and 16 can be performed by methods well known in the art, e.g. aqueous NaOH in DMSO at RT to 40° C. gave acids 18 or 19 respectively (step g).

Scheme 3

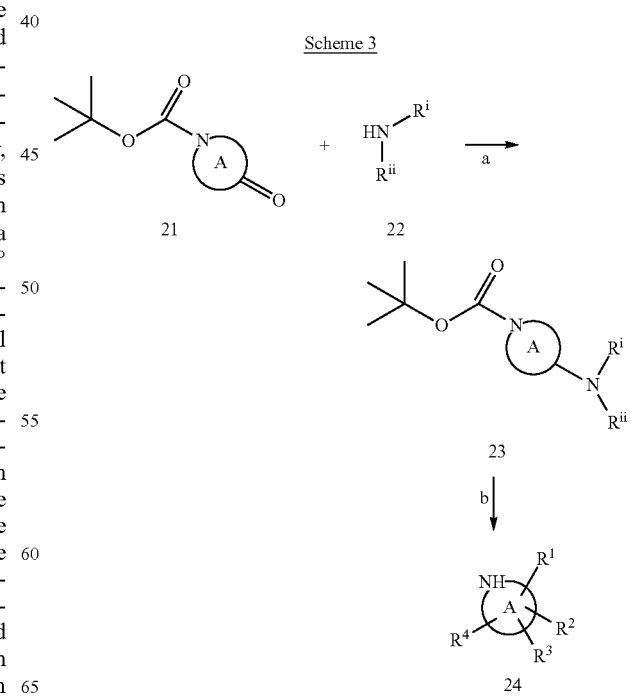

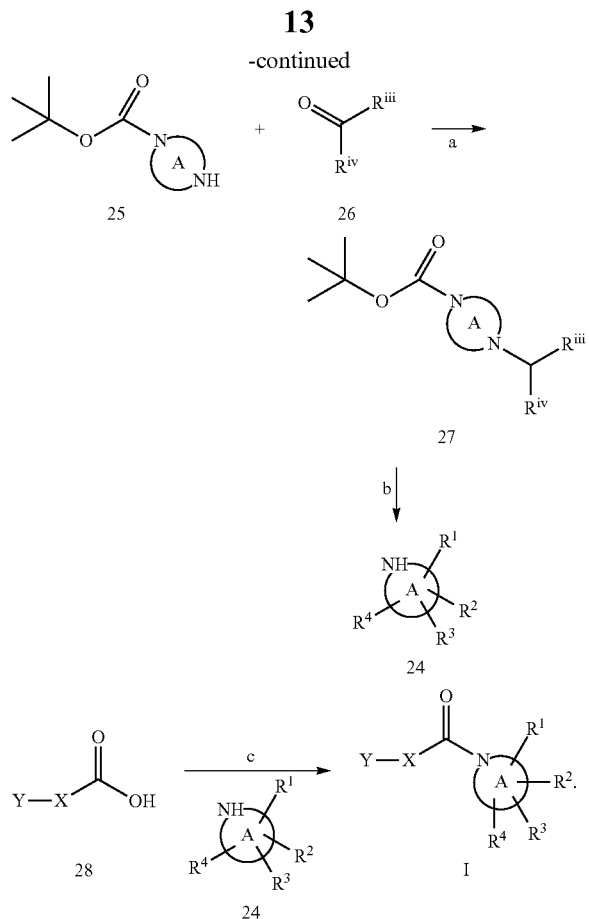

R¹, R², R³, R⁴, X and Y are as defined before.

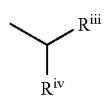

is heterocyclyl, which is a non-aromatic mono-cyclic radical of four to eight ring atoms, in which two ring atoms are nitrogen atoms, the remaining ring atoms being carbon atoms. $R^i$ and $R^{ii}$ are independently hydrogen, $C_{1-6}$ alkyl, acyl, heteroalkyl, optionally substituted $C_{3-7}$ cycloalkyl or optionally substituted heterocyclyl, or is optionally substituted heterocyclyl.

is $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl or optionally substituted $C_{3-7}$ cycloalkyl $C_{1-6}$ alkyl, optionally substituted heterocyclyl or optionally substituted heterocyclyl $C_{1-6}$ alkyl.)

Secondary amines 24 (scheme 3) are known, can be prepared by methods known in the art, methods described in the examples or can be prepared e.g. by reductive amination of ketones 21 with secondary amines 22 or by reductive amination of secondary amines 25 with ketones 26, e.g. using sodium triacetoxy-borohydride, sodium cyano-borohydride or borane-pyridine complex as reagents in the presence of acetic acid and potentially a base like trietylamine in a solvent like halo-alkane optionally with ethanol at temperatures around RT (step a). Such a reductive amination leads to Boc-protected adducts 23 or 27 which are subsequently deprotected by well established procedures as e.g. trifluoroacetic acid with or without an additional solvent or alcoholic hydrogen chloride to give secondary amines 24 (step b). Pyrazole carboxylic acids 28 can then be coupled with secondary amines 24 by coupling methods like use of O-(7-azabenzotriazol-1-yl)-1,1,3,3-tetramethyluronium hexafluorophosphate (HATU), triethyl amine in N,N-dimethylformamide or by reaction of the pyrazole carboxylic acids 28 first with 2-chloro-4,6-dimethoxy-[1,3,5]triazine and N-methylmorpholine in acetonitrile followed by addition of the secondary amines 24 (0° C. to RT) or by activation of the acid 28 with oxalyl chloride/catalytic amount of DMF, followed by reaction with amines 24 in the presence of a tertiary amine like triethyl amine (step c).

Scheme 4

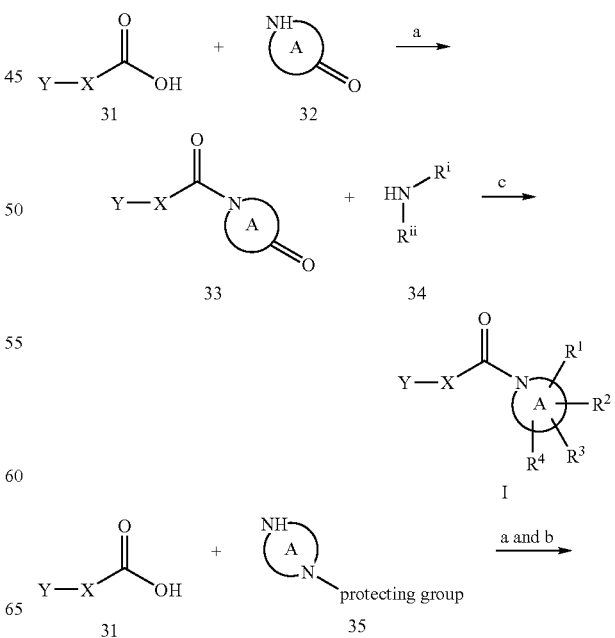

-continued

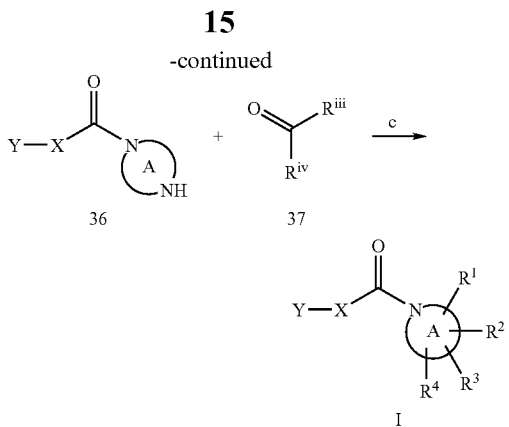

(In Scheme 4,

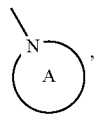

$R^1$, $R^2$, $R^3$, $R^4$, X and Y are as defined before.

is heterocyclyl, which is a non-aromatic mono-cyclic radical of four to eight ring atoms, in which two ring atoms are nitrogen atoms, the remaining ring atoms being carbon atoms. $R^i$ and $R^{ii}$ are independently hydrogen, $C_{1-6}$ alkyl, acyl, heteroalkyl, optionally substituted $C_{3-7}$ cycloalkyl or optionally substituted heterocyclyl, or

is optionally substituted heterocyclyl.

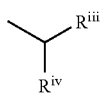

is $C_{1-6}$ alkyl, halo $C_{1-6}$ alkyl, heteroalkyl, $C_{2-6}$ alkenyl, $C_{2-6}$ aklynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl or optionally substituted $C_{3-7}$ cycloalkyl $C_{1-6}$ alkyl, optionally substituted heterocyclyl or optionally substituted heterocyclyl $C_{1-6}$ alkyl.)

Amide 33 or 36 (scheme 4) can be prepared from pyrazole carboxylic acids 31 and amines 32 or 35 by methods known in the art, methods described in the examples or can be prepared e.g. like use of O-(7-azabenzotriazol-1-yl)-1,1,3,3-tetramethyluronium hexafluorophosphate (HATU), triethyl amine in N,N-dimethylformamide (step a). In case of amine 36, the coupling product has to be deprotected e.g. Boc-deprotection is established with trifluoroacetic acid with or without an additional solvent or alcoholic hydrogen chloride to give secondary amines 36 (step a and b). Reductive amination of ketones 33 with secondary amines 34 or by reductive amination of secondary amines 36 with ketones 37 ($R^i$, $R^{ii}$, $R^{iii}$, $R^{iv}$, representing substituents as described in the claims for $R^1$ to $R^4$) e.g. using sodium triacetoxy-borohydride, sodium cyanoborohydride or borane-pyridine complex as reagents in the presence of acetic acid and potentially a base like trietylamine in a solvent like halo-alkane optionally with ethanol at temperatures around RT (step c) give the final compounds I.

Newly Y substituted pyrazole I can be prepared from pyrazole I (with Y containing a bromo or iodo aryl or heteroaryl system) by methods well known in the art. Suzuki coupling with boronic acids in the presence of a catalyst like palladium-(II)-acetate and in the presence of tricyclohexylphosphine and a base like potassium phosphate in a solvent like toluene or N,N-dimethylformamide in a temperature range preferably between about 70° C. and about 130° C. Sonogashira coupling was performed in analogy to Stara, Irena G.; Stary, Ivo; Kollarovic, Adrian; Teply, Filip; Saman, David; Fiedler, Pavel. Collect. Czech. Chem. Commun. (1999), 64(4), 649-672, with a reagent containing a terminal acetylene function in the presence of copper(I) iodide, tetrakis-(triphenylphosphine)-palladium in piperidine at 50° C. to 80° C. The triple bond in the acetylenic substituent can optionally be reduced to a single bond by hydrogenation using e.g. $PtO_2$ or Pd/C as catalyst. Pyrazole I (with Y containing a nitro aryl or heteroaryl system) could be hydrogenated with Pd/C as catalyst and then further reacted with acid chlorides or coupled with acids in the presence of coupling reagents like HATU or EDCI (N-(3-Dimethylaminopropyl)-N'-ethylcarbodiimide hydrochloride). Optionally any substituent present in I can be modified at the ester state (ester 4 scheme 1, or ester 15 or 16 in scheme 2) of the synthesis.

Scheme 5

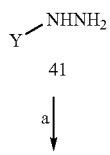

-continued

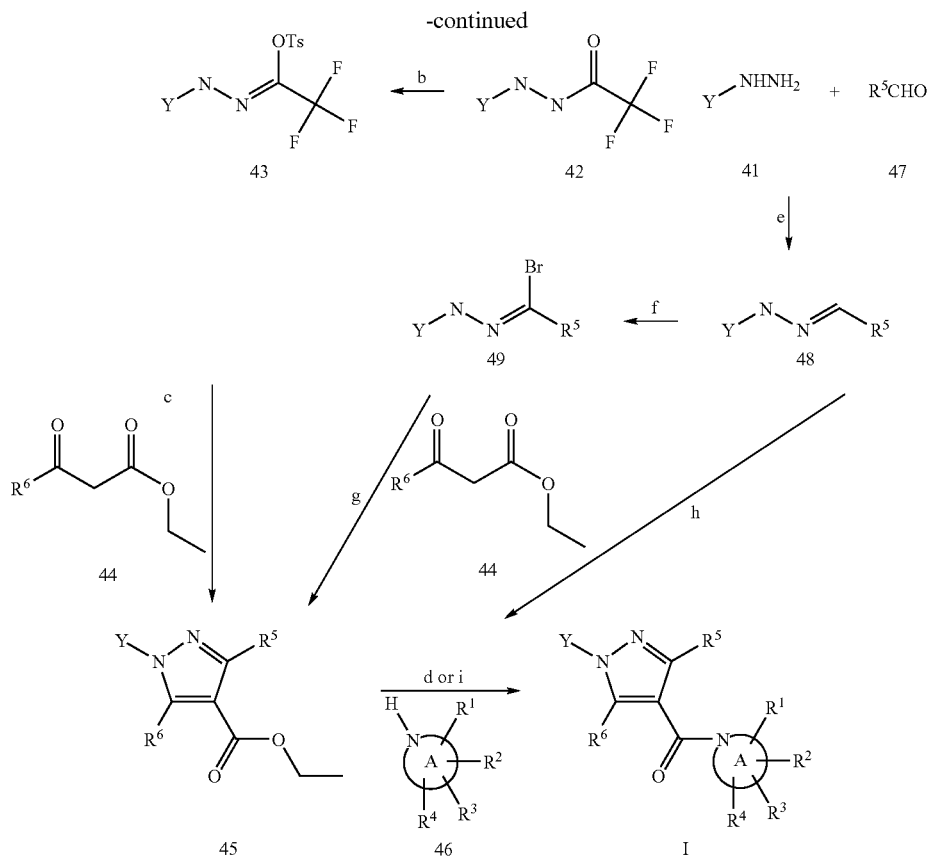

(In Scheme 5,

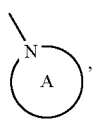

$R^1, R^2, R^3, R^4, R^5, R^6$ and Y are as defined before. Hydrazines 41 (scheme 5) are known or can be prepared by methods known in the art (see scheme 1). Hydrazine 41 can be reacted with trifluoroacetic acid anhydride to hydrazide 42 (step a) and is then further transformed with p-toluenesulfonyl chloride/N-methylmorpholine to the tosyl derivative 43 (step b). Following conditions described in Kiyoshi Tanaka et al. Bull. Chem. Soc. Jpn., 59, 2631 (1986), deprotonation of beta-ketoester 44 with sodium ethanolate in ethanol and reaction with tosylate 43 at 0° C. to room temperature gives pyrazole 45 (step c). Hydrolysis of the ester and coupling with the amine 46 as already described in scheme 2 and scheme 3 gives the Final compound I (step d).

Alternatively haydrazone 48 was prepared from hydrazine 41 and aldehyde 47 in the presence of sodium acetate in acetic acid at room temperature to 50° C. (step e). Following literature procedure (A. S. Shawali and H. M. Hassanee, Tetratrahedron, 29, 121 (1973)) hydrazone 48 can be brominated with bromine in acetic acid (step f). The corresponding bromide 49 reacts then with the deprotonated beta-ketoester 44 (sodium ethanolate in ethanol) at 0° C. to 50° C. to give pyrazole 45 (step g). Following literature procedure (Gerhard Mann et al. Synthesis, 331 (1985)) hydrazone 48 can also be reacted with beta-ketoester 44 in the presence of zinc chloride at room temperature to 170° C. (step h).

In case $R^6$ contains a protected group, pyrazole 45 is an ideal intermediate for deprotection and introduction of new groups to give 45 with a new $R^6$. In case $R^6$ is an alkyne or furane, these groups can further be transformed to an acid and further to hetero aryl systems by methods known in the art. Hydrolysis of the ester and coupling with the amine 46 is already described in scheme 2 and scheme 3 and gives the final compound I (step i).

As described above, the compounds of formula (I) are CCR2 receptor antagonists, with some antagonist activity also at CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication. The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by the following assays.

Receptor Binding Assay

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a topcounter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin. For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of general formula (I) exhibit IC50 values in the Ca mobilisation assay or in the receptor binding assay of 0.1 nM to 10 µM, preferably 1 nM to 1.5 µM for CCR2. The following table shows measured values in the calcium mobilization assay for some selected compounds of the present invention.

| Example | IC50(µM) |
|---------|----------|
| 29      | 0.100    |
| 76      | 0.122    |
| 83      | 0.658    |
| 122     | 0.73     |

| Example | IC50(µM) |
|---------|----------|
| 119     | 0.306    |
| 138     | 0.154    |
| 139     | 0.141    |
| 161     | 0.0972   |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations:
AcOH=Acetic acid, BOC=t-Butyloxycarbonyl, BuLi=Butyllithium, CDI=1,1-carbonyldiimidazole, $CH_2Cl_2$=dichloromethane, DCE=1,2-dichloroethane, DIBALH=Di-i-butylaluminium hydride, DCC=N,N'-Dicyclohexylcarbodiimide, DMA=N,N-Dimethylacetamide, DMAP=4-Dimethylaminopyridine, DMF=N,N-Dimethylformamide, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HATU=O-(7-azabenzotriazol-1-yl)-1,1,3,3-tetramethyluronium hexafluorophosphate, HOBT=1-Hydroxybenzo-triazole, Huenig's base=$iPr_2NEt$=N-Ethyl diisopropylamine, LAH=Lithium aluminium hydride, LDA=Lithium diisopropylamide, $LiBH_4$=Lithium borohydride, MeOH=Methanol, NaI=Sodium iodide, Red-Al=Sodium bis(2-methoxyethoxy)aluminium hydride, RT=room temperature, TBDMSCl=t-Butyldimethylsilyl chloride, TFA=Trifluoroacetic acid, THF=Tetrahydrofurane, quant=quantitative.

General Remarks
All reactions were performed under argon.

Intermediate 1

1-{3-[(E)-2-(4-Chloro-phenyl)-vinyl]-phenyl}-3,5-diethyl-1H-pyrazole-4-carboxylic acid A) 3-Oxo-2-propionyl-pentanoic acid methyl ester 5.21 g=5.02 ml (39.2 mmol) of 3-oxo-pentanoic acid methyl ester were dissolved in 30 ml of $CH_2Cl_2$, the solution was cooled to 2° C. and 3.81 g (39.2 mmol) of anhydrous magnesium chloride were added in small portions. Then, 6.21 g=6.34 ml (78.4 mmol) of pyridine were added to this suspension between 2° C. and 5° C., followed by 3.89 g=3.67 ml (41.2 mmol) of propionyl chloride. The reaction mixture was warmed up to RT and 1 hour later poured into crashed ice, acidified with HCl (25%) to pH 1-2 and extracted twice with $Et_2O$. The organic phases were dried over magnesium sulfate, filtered and evaporated to give 7.62 g of title compound as light yellow oil. MS: 185.1 ([M−H]−).

B) (E and/or Z)-3-Methoxy-2-propionyl-pent-2-enoic acid methyl ester 7.50 g (40.3 mmol) of 3-oxo-2-propionyl-pentanoic acid methyl ester were dissolved in 40 ml of MeCN and the mixture cooled to 2° C. While stirring, 13.26 g (40.3 mmol) of caesium carbonate were added in small portions and the reaction then warmed up to RT. 6.86 g=4.73 ml (40.3 mmol) of methyl trifluoromethanesulfonate were then added drop by drop between 22 and 25° C. After 90 min, the reaction mixture was poured into crashed ice and extracted twice with $Et_2O$; the organic phases were washed with water, dried over magnesium sulfate, filtered and evaporated to give 7.86 g of crude compound as yellow oil.

C) 1-(3-Bromo-phenyl)-3,5-diethyl-1H-pyrazole-4-carboxylic acid methyl ester

A solution of 7.10 g (35.5 mmol) of (E and/or Z)-3-methoxy-2-propionyl-pent-2-enoic acid methyl ester in 10 ml of MeOH was added to a solution of 8.09 g (35.5 mmol) of 3-bromophenylhydrazine hydrochloride in 150 ml of MeOH and the mixture was cooled to −20° C. To this mixture was added a solution of 3.79 g=5.22 ml (37.2 mmol) of $Et_3N$ in 40 ml of MeOH drop by drop and the reaction was then warmed up to RT. After 20 hours, it was poured into crashed ice and extracted twice with $Et_2O$; the organic phases were washed with water, dried over magnesium sulfate, filtered and evaporated to give 7.62 g of the title compound as light red oil. MS: 337.1 ($MH^+$, 1 Br).

D) 1-{3-[(E)-2-(4-Chloro-phenyl)-vinyl]-phenyl}-3,5-diethyl-1H-pyrazole-4-carboxylic acid methyl ester 2.10 g (5.0 mmol) of 1-(3-bromo-phenyl)-3,5-diethyl-1H-pyrazole-4-carboxylic acid methyl ester and 1.82 g (10.0 mmol) of (E)-2-(4-chlorophenyl)vinyl boronic acid were dissolved in 50 ml of DMF. 12.5 ml of anhydrous potassium phosphate (tribasic, 2 M in water) were added drop by drop below 25° C., followed by 0.29 g (0.2 mmol) of tetrakis-(triphenylphosphine)-palladium. The reaction mixture was then stirred at 80° C. for 20 hours, cooled to RT, poured into crashed ice and extracted twice with $CH_2Cl_2$; the organic phases were washed with water, dried over magnesium sulfate, filtered and evaporated. The residue was purified by flash column chromatography (n-heptane:EtOAc 1:0-8:2) to afford the title compound as light yellow solid. MS: 395.0 ($MH^+$, 1 Cl).

E) 1-{3-[(E)-2-(4-Chloro-phenyl)-vinyl]-phenyl}-3,5-diethyl-1H-pyrazole-4-carboxylic acid A solution of 1.78 g (4.5 mmol) of 1-{3-[(E)-2-(4-chlorophenyl)-vinyl]-phenyl}-3,5-diethyl-1H-pyrazole-4-carboxylic acid methyl ester in 100 ml of THF/MeOH (1:1) was treated with 11.3 ml of lithium hydroxide solution (1 M in water) at RT and then stirred at reflux (boiling temperature=80° C.) for 60 hours. The reaction mixture was then cooled to RT and evaporated. The residue was partitioned between water and $CH_2Cl_2$, acidified with HCl (2N) to pH 1-2 and extracted twice with $CH_2Cl_2$. The organic phases were washed with water, dried over magnesium sulfate, filtered and evaporated to give 1.69 g of crude title compound as light yellow solid. MS: 379.2 ([M–H]$^-$, 1 Cl).

Intermediate 2

3,5-Diethyl-1-(3-hex-1-ynyl-phenyl)-1H-pyrazole-4-carboxylic acid

A) 3,5-Diethyl-1-(3-hex-1-ynyl-phenyl)-1H-pyrazole-4-carboxylic acid methyl ester A solution of 4.20 g (10.0 mmol) of 1-(3-bromo-phenyl)-3,5-diethyl-1H-pyrazole-4-carboxylic acid methyl ester (intermediate 1C) in 35 ml of piperidine was treated with 0.19 g (1.0 mmol) of copper(I)iodide and 1.16 g (1.0 mmol) of tetrakis-(triphenylphosphine)-palladium. The reaction mixture was warmed up to 60° C. and after 15 min, a solution of 0.82 g=1.00 ml (10.0 mmol) of hex-1-yne in 15 ml of piperidine was added drop by drop during 1 hour. After 30 min, the oil bath temperature was steadily increased to 80° C. The reaction mixture was then stirred at 80° C. for 4 hours, and subsequently cooled down to RT. The solvent was evaporated and the residue poured into crashed ice, acidified with HCl (37%) to pH 1-2 and extracted twice with EtOAc; the organic phases were washed with water, dried over magnesium sulfate, filtered and evaporated. The residue was purified by flash column chromatography (n-heptane:EtOAc 1:0-9:1) to afford the title compound as light yellow oil. MS: 339.0 (MH$^+$).

B) 3,5-Diethyl-1-(3-hex-1-ynyl-phenyl)-1H-pyrazole-4-carboxylic acid

In analogy to the procedure described for intermediate 1E, 3,5-diethyl-1-(3-hex-1-ynyl-phenyl)-1H-pyrazole-4-carboxylic acid methyl ester has been saponified to give the title compound as colorless oil. MS: 323.2 ([M–H]$^-$).

Intermediate 3

1-{3-[(E)-2-(4-Chloro-phenyl)-vinyl]-phenyl}-3,5-bis-methoxymethyl-1H-pyrazole-4-carboxylic acid In analogy to the procedures described for intermediates 1A-E, the title compound has been obtained by i) condensation of methyl 4-methoxyacetoacetate with methoxyacetyl chloride to give 4-methoxy-2-(2-methoxy-acetyl)-3-oxo-butyric acid methyl ester; ii) methylation of 4-methoxy-2-(2-methoxy-acetyl)-3-oxo-butyric acid methyl ester with methyl trifluoromethanesulfonate to give (E and/or Z)-3,4-dimethoxy-2-(2-methoxy-acetyl)-but-2-enoic acid methyl ester; iii) condensation of (E and/or Z)-3,4-dimethoxy-2-(2-methoxy-acetyl)-but-2-enoic acid methyl ester with (3-bromo-phenyl)-hydrazine to give 1-(3-bromo-phenyl)-3,5-bis-methoxymethyl-1H-pyrazole-4-carboxylic acid methyl ester; iv) reaction of 1-(3-bromo-phenyl)-3,5-bis-methoxymethyl-1H-pyrazole-4-carboxylic acid methyl ester with (E)-2-(4-chlorophenyl)vinyl boronic acid to give 1-{3-[(E)-2-(4-chloro-phenyl)-vinyl]-phenyl}-3,5-bis-meth-oxymethyl-1H-pyrazole-4-carboxylic acid methyl ester; v) saponification of 1-{3-[(E)-2-(4-chloro-phenyl)-vinyl]-phenyl}-3,5-bis-methoxymethyl-1H-pyrazole-4-carboxylic acid methyl ester to give the title compound as light brown solid. MS: 411.2 ([M–H]$^-$, 1 Cl).

Intermediate 4

1-{3-[(E)-2-(4-Chloro-phenyl)-vinyl]-phenyl}-3,5-dimethyl-1H-pyrazole-4-carboxylic acid In analogy to the procedure described in Example 14C], but with 2.8 eq of $K_3PO_4$, 1-(3-bromo-phenyl)-3,5-dimethyl-1H-pyrazole-4-carboxylic acid and trans-2-(4-chlorophenyl) vinylboronic acid gave after suspending in $CH_2Cl_2$ and filtration the title compound in 63% yield as light yellow solid. MS: 352.2 (M$^+$, 1 Cl).

Intermediate 5

1-(4-Benzofuran-2-yl-pyrimidin-2-yl)-5-cyclopropyl-1H-pyrazole-4-carboxylic add

A) 4-Benzofuran-2-yl-2-methylsulfanyl-pyrimidine

4-Chloro-2-methylthiopyrimidine (1.6 g, 10.0 mmol), 2-benzofuranboronic acid (1.9 g, 12.0 mmol), tetrakis-(triphenylphosphine)-palladium (0.3 g, 0.3 mmol) were dissolved in dioxane (10 ml) and aqueous $Na_2CO3$ (11 ml, 2M solution in water, 22 mmol) was added. The reaction was heated to 80° C. under argon for 16 h after which time the dioxane was evaporated and the reaction mixture diluted with water and extracted with $CH_2Cl_2$. The organic was dried ($Na_2SO_4$), concentrated and the residue purified by flash column chromatography ($CH_2Cl_2$:n-heptane 8:2) to afford the title compound (1.0 g, 43%) as a white solid. MS: 243.0 (MH$^+$).

B) 4-Benzofuran-2-yl-2-methanesulfonyl-pyrimidine

Intermediate 5A (1.0 g, 4 mmol) was dissolved in $CH_2Cl_2$ (10 ml), cooled to 0° C. and meta-chloroperbenzoic acid (2.2 g, 85%, 11 mmol) was added. The reaction was stirred for 1 h after which time the reaction was diluted with $CH_2Cl_2$ and repeatedly washed with saturated $NaHCO_3$ and the organic dried ($Na_2SO_4$) and concentrated to afford the title compound (1.1 g, 100%) as a white solid. MS: 275.0 (MH$^+$).

C) (4-Benzofuran-2-yl-pyrimidin-2-yl)-hydrazine dihydrochloride salt

Intermediate 5B (1.1 g, 4 mmol) was dissolved in a mixture of DMF (8 ml) and hydrazine monohydrate (1.3 ml, 25 mol) and heated to 130° C. for 1 h. The resulting solid was collected by filtration, dissolved in 25% HCl (10 ml) and heated to reflux for 30 minutes after which time the reaction was concentrated affording the title compound (1.2 g, quant) as a yellow solid. MS: 227.1 (MH$^+$).

D) 1-(4-Benzofuran-2-yl-pyrimidin-2-yl)-5-cyclopropyl-1H-pyrazole-4-carboxylic acid methyl ester Intermediate 5C (1.2 g, 4 mmol) was suspended with 2-cyclopropanecarbonyl-3-dimethylamino-acrylic acid methyl ester (1.8 g, 9 mmol) (prepared as described Bioorg. Med. Chem. Lett. 2001, 11, 6, p 803) in DMF (10 ml) and heated to 80° C. for 40 minutes after which time the reaction was concentrated, the residue redissolved in EtOAc, washed with E) 1-(4-Benzofuran-2-yl-pyrimidin-2-yl)-5-cyclopropyl-1H-pyrazole-4-carboxylic acid To intermediate 5D (1.4 g, 4 mmol) in DMSO (5 ml) was added a solution of NaOH (1.3 ml, 6M in water, 8 mmol) and the mixture stirred for 16 h after which time 1M HCl was added allowing isolation of the title product (0.8 g, 61%) by filtration, a yellow solid. MS: 347.1 (MH$^+$).

Intermediate 6

3,5-Dimethyl-1-(5-trifluoromethyl-pyridin-3-yl)-1H-pyrazole-4-carboxylic acid

A) 3,5-Dimethyl-1-(5-trifluoromethyl-pyridin-3-yl)-1H-pyrazole-4-carboxylic acid ethyl ester 3,5-Dimethyl-1H-pyrazole-4-carboxylic acid ethyl ester (0.10 g, 1 mmol) (prepared as described in Tett 2002, 58, 18, p 3639), 3-bromo-5-trifluoromethyl-pyridine (0.16 g, 1 mmol), copper iodide (0.02 g, 0.2 mmol) and cesium carbonate (1.0 g, 3 mmol) were suspended in DMA (0.5 ml) and heated to 160° C. for 16 h. The reaction was diluted with EtOAc, washed repeatedly with ammonium hydroxide, brine and dried (Na$_2$SO$_4$) and concentrated. The residue was purified by flash column chromatography (EtOAc:n-heptane 1:9-2:8 gradient affording the title compound (0.07 g, 35%) as a yellow oil. MS: 314.2 (MH$^+$).

B) 3,5-Dimethyl-1-(5-trifluoromethyl-pyridin-3-yl)-1H-pyrazole-4-carboxylic acid Intermediate 6A (0.07 g, 0.2 mmol) was dissolved in EtOH (0.5 ml) and a solution of NaOH (0.07 ml, 6M in water, 0.4 mmol) added. The reaction was stirred overnight after which time the reaction was made acidic by addition of Amberlite IR120 plus resin, the mixture filtered and concentrated, affording the title compound (0.06 g, 80%) as a off-white solid. MS: 286.1 (MH$^+$).

Intermediate 7

3,5-Dimethyl-1-(3-trifluoromethyl-phenyl)-1H-pyrazole-4-carboxylic acid

A) 3,5-Dimethyl-1-(3-trifluoromethyl-phenyl)-1H-pyrazole-4-carboxylic acid ethyl ester The title compound was prepared in analogy to intermediate 6A by reaction of 3,5-Dimethyl-1H-pyrazole-4-carboxylic acid ethyl ester (2 g, 12 mmol) with 3-trifluoroiodobenzene (3.9 g, 14 mmol) affording the desired product (1.2 g, 30%) as a yellow liquid. MS: 313.2 (MH$^+$).

B) 3,5-Dimethyl-1-(3-trifluoromethyl-phenyl)-1H-pyrazole-4-carboxylic acid

The title compound was prepared in analogy to intermediate 6 by hydrolysis of intermediate 7A with sodium hydroxide affording the product as a white solid. MS: 283.1 (M−H).

Intermediate 8

3,5-Dimethyl-1-(3-trifluoromethoxy-phenyl)-1H-pyrazole-4-carboxylic acid

A) 3,5-Dimethyl-1-(3-trifluoromethoxy-phenyl)-1H-pyrazole-4-carboxylic acid ethyl ester The title compound was prepared in analogy to intermediate 6A by reaction of 3,5-Dimethyl-1H-pyrazole-4-carboxylic acid ethyl ester (2 g, 12 mmol) with 3-trifluoromethoxy-iodobenzene (6.7 g, 14 mmol) affording the desired product (2.9 g, 73%) as a colourless liquid. MS: 329.2 (MH$^1$).

B) 3,5-Dimethyl-1-(3-trifluoromethoxy-phenyl)-1H-pyrazole-4-carboxylic acid

The title compound was prepared in analogy to intermediate 6 by hydrolysis of intermediate 8A with sodium hydroxide affording the product as a white solid. MS: 301.1 (MH$^1$).

Intermediate 9

1-[3,5-Dimethyl-1-(3-trifluoromethoxy-phenyl)-1H-pyrazole-4-carbonyl]-piperidin-4-one Intermediate 8 (0.9 g, 3 mmol), 4-piperidone monohydrate hydrochloride (0.4 g, 4 mmol), EDCI (0.7 g, 4 mmol), HOBT (0.4 g, 3 mmol) were mixed in DMF (15 ml) and triethylamine (1.2 ml, 9 mmol) was added. The mixture was heated at 60° C. for 3 h after which time the reaction was concentrated, the residue redissolved in CH$_2$Cl$_2$, washed with saturated NaHCO$_3$, brine, dried (Na$_2$SO$_4$) and concentrated. The residue was purified by flash column chromatography (EtOAc:n-heptane 1:1) affording the title compound (1.1 g, 92%) as a colourless oil. MS: 382.2 (MH$^+$).

Intermediate 10

1-[3,5-Dimethyl-1-(3-trifluoromethoxy-phenyl)-1H-pyrazole-4-carbonyl]-pyrrolidin-3-one The title compound was prepared in analogy to intermediate 9 by reaction of intermediate 8 with pyrolidinone hydrochloride (prepared by HCl in dioxane deprotection of Boc-pyrrolidinone) affording the product as a colourless oil. MS: 368.1 (MH$^+$).

Intermediate 11

3-Cyclopropyl-5-methyl-1-(3-trifluoromethyl-phenyl)-1H-pyrazole-4-carboxylic acid A) 2-Cyclopropanecarbonyl-3-oxo-butyric acid ethyl ester To a solution of ethylacetoacetate (11.0 g, 85 mmol) in THF (20 ml) at 0° C. under argon atmosphere was added isopropylmagnesium chloride (42 ml, 2 M in THF, 85 mmol) dropwise. The reaction was stirred for 0.5 h. This solution was then transferred by cannula to a solution of cyclopropylcarbonylchloride (8.8 g, 85 mmol) and imidazole (0.3 g, 4 mmol) in THP (30 ml), also under argon at 0° C. The reaction was stirred for 2 h at 0° C. and 1 h at room temperature before the reaction was quenched by addition of 10% citric acid solution. The reaction was then extracted with EtOAc, dried (Na$_2$SO$_4$) and concentrated. Purification by flash column

B) 5-Cyclopropyl-3-methyl-1H-pyrazole-4-carboxylic acid ethyl ester

To a solution of intermediate 11A (3.8 g, 19 mmol) in EtOH (20 ml) was added hydrazine monohydrochloride (1.3 g, 19 mmol) in water (10 ml). The reaction was stirred for 1 h after which time the reaction was concentrated and the residue recrystallised from EtOAc, affording the title compound (3.2 g, 83%) as a white, crystalline solid. MS: 195.1 (MH$^+$).

C) 3-Cyclopropyl-5-methyl-2-(3-trifluoromethyl-phenyl)-1H-pyrazole-4-carboxylic acid ethyl ester and 5-cyclopropyl-3-methyl-1-(3-trifluoromethyl-phenyl)-1H-pyrazole-4-carboxylic acid ethyl ester The title compound was prepared in analogy to intermediate 8A affording 3-cyclopropyl-5-methyl-2-(3-trifluoromethyl-phenyl)-1H-pyrazole-4-carboxylic acid ethyl ester as the major product. MS: 339.1 (MH$^+$).

The minor regioisomer 5-cyclopropyl-3-methyl-1-(3-trifluoromethyl-phenyl)-1H-pyrazole-4-carboxylic acid ethyl ester can also be isolated from this reaction. MS: 339.1 (MH$^+$).

D) 3-Cyclopropyl-5-methyl-1-(3-trifluoromethyl-phenyl)-1H-pyrazole-4-carboxylic acid The title compound was prepared from the major product intermediate 6 by hydrolysis with sodium hydroxide in analogy to intermediate 8C. MS: 311.1 (MH$^+$).

Intermediate 12

5-Cyclopropyl-3-methyl-1-(3-trifluoromethyl-phenyl)-1H-pyrazole-4-carboxylic acid The title compound was prepared by sodium hydroxide hydrolysis of the minor isomer-cyclopropyl-3-methyl-1-(3-trifluoromethyl-phenyl)-1H-pyrazole-4-carboxylic acid ethyl ester from formation of intermediate 11. MS: 311.1 (MH$^+$).

Intermediate 13

3-Cyclopropyl-5-methyl-1-(3-trifluoromethoxy-phenyl)-1H-pyrazole-4-carboxylic acid

A) 3-Cyclopropyl-5-methyl-1-(3-trifluoromethoxy-phenyl)-1H-pyrazole-4-carboxylic acid ethyl ester and 5-Cyclopropyl-3-methyl-1-(3-trifluoromethoxy-phenyl)-1H-pyrazole-4-carboxylic acid ethyl ester 3-Cyclopropyl-5-methyl-1-(3-trifluoromethoxy-phenyl)-1H-pyrazole-4-carboxylic acid ethyl ester was prepared from intermediate 11B and 3-trifluoromethoxyiodobenzene in analogy to intermediate 6 as the major product of the reaction. MS: 355.2 (MH$^+$).

5-Cyclopropyl-3-methyl-1-(3-trifluoromethoxy-phenyl)-1H-pyrazole-4-carboxylic acid ethyl ester can also be isolated as the minor regioisomer from the reaction. MS: 327.1 (MH$^+$).

B) 3-Cyclopropyl-5-methyl-1-(3-trifluoromethoxy-phenyl)-1H-pyrazole-4-carboxylic acid The title compound was prepared from 3-Cyclopropyl-5-methyl-1-(3-trifluoromethoxy-phenyl)-1H-pyrazole-4-carboxylic acid ethyl ester by hydrolysis with sodium hydroxide in analogy to intermediate 6. MS: 327.1 (MH$^+$).

Intermediate 14

5-Cyclopropyl-3-methyl-1-(3-trifluoromethoxyphenyl)-1H-pyrazole-4-carboxylic acid The title compound was prepared by sodium hydroxide hydrolysis of the minor isomer-5-cyclopropyl-3-methyl-1-(3-trifluoromethoxy-phenyl)-1H-pyrazole-4-carboxylic acid ethyl ester from formation of intermediate 6. MS: 327.1 (MH$^+$).

Alternatively, 5-cyclopropyl-3-methyl-1-(3-trifluoromethoxy-phenyl)-1H-pyrazole-4-carboxylic acid can be prepared with complete regioselectivity by the following protocol.

To a solution of intermediate 11A, 2-cyclopropanecarbonyl-3-oxo-butyric acid ethyl ester (2.0 g, 10 mmol) in acetic acid (10 ml), cooled at 5° C., was added a solution of (3-Trifluoromethoxy-phenyl)-hydrazine (2.1 g, 11 mmol) in acetic acid (10 ml). The reaction was allowed to come to room temperature (1 h) after which time the reaction was concentrated, the residue dissolved in DCM, washed with saturated NaHCO$_3$, (Na$_2$SO$_4$) and concentrated. Purification by flash column chromatography (EtOAc:n-heptane 1:9) afforded 5-cyclopropyl-3-methyl-1-(3-trifluoromethoxy-phenyl)-1H-pyrazole-4-carboxylic acid ethyl ester (2.8 g, 77%). Saponification of the ester with NaOH in analogy to intermediate 6 affords the title compound.

Intermediate 15

1-[5-Cyclopropyl-3-methyl-1-(3-trifluoromethoxy-phenyl)-1H-pyrazole-4-carbonyl]-piperidin-4-one Reaction of intermediate 14 with 4-piperidone monohydrate hydrochloride in analogy to intermediate 9 affords the title compound. MS: 408.2 (MH$^+$).

Intermediate 16

3,5-Dicyclopropyl-1-(3-trifluoromethyl-phenyl)-1H-pyrazole-4-carboxylic acid

A) 2-Cyclopropanecarbonyl-3-oxo-butyric acid ethyl ester

To a suspension of magnesium chloride (3.3 g, 35 ml) in CH$_2$Cl$_2$ (15 ml) under argon at 0° C. was added methyl-3-cyclopropyl-oxopropanoate (5.0 g, 35 mmol), followed by pyridine (2.8 ml, 35 mmol). The mixture was stirred for 1 h before the addition of a solution of cyclopropylcarbonylchloride (3.2 ml, 35 mol) in CH$_2$Cl$_2$ (5 ml), followed by more pyridine (2.8 ml, 35 mmol) and the mixture was stirred for a further 1 h. The reaction was washed repeatedly with 6N HCl, dried (Na$_2$SO$_4$) and concentrated. Purification by flash column chromatography (EtOAc:n-heptane 1:9) afforded the title product (7.4 g, 99%) as a colourless oil. MS: 211.1 (MH+).

B) 3,5-Dicyclopropyl-1H-pyrazole-4-carboxylic acid methyl ester

The title compound was prepared in analogy to intermediate 11B by reaction of intermediate 16A 2-cyclopropanecarbonyl-3-oxo-butyric acid ethyl ester with hydrazine monohydrochloride. MS: 207.1 (MH+).

C) 3,5-Dicyclopropyl-1-(3-trifluoromethyl-phenyl)-1H-pyrazole-4-carboxylic acid methyl ester The title compound was prepared by reaction of intermediate 16B 3,5-dicyclopropyl-1H-pyrazole-4-carboxylic acid methyl ester with 3-trifluoromethlyiodobenzene in analogy to intermediate 6A. MS: 367.2 (MH+).

D) 3,5-Dicyclopropyl-1-(3-trifluoromethyl-phenyl)-1H-pyrazole-4-carboxylic acid The title compound was prepared by reaction of intermediate 16B with NaOH in analogy to intermediate 6. MS: 353.1 (MH+).

Intermediate 17

3,5-Dicyclopropyl-1-(3-trifluoromethyl-phenyl)-1H-pyrazole-4-carboxylic acid

A) 3,5-Dicyclopropyl-1-(3-trifluoromethoxy-phenyl)-1H-pyrazole-4-carboxylic acid methyl ester The title compound was prepared by reaction of intermediate 16A with 3-trifluormethoxyidobenzene in analogy to intermediate 6A. MS: 351.1 (MH+).

B) 3,5-Dicyclopropyl-1-(3-trifluoromethoxy-phenyl)-1H-pyrazole-4-carboxylic acid The title compound was prepared by hydrolysis of intermediate 17A in analogy to intermediate 6. MS: 337.1 (MH+).

Intermediate 18

Methyl-(R)-pyrrolidin-3-yl-(tetrahydro-pyran-4-yl)-amine

A) ((R)-1-Benzyl-pyrrolidin-3-yl)-methyl-(tetrahydro-pyran-4-yl)-amine

To a solution of (R)-1-benzyl-pyrrolidin-3-ylamine (1.0 g, 6 mmol), tetrahydro-4H-pyran-4-one (0.6 g, 6 mmol) in $CH_2Cl_2$ (15 ml) was added acetic acid (0.7 ml, 11 mmol) and sodium triacetoxyborohydride (1.4 g, 7 mmol) and the reaction stirred for 1 h. EtOH (15 ml) was added to the reaction, followed by formaldehyde (1 ml, 36% solution in water) and finally sodium cyanoborohydride (0.4 g, 7 mmol) and the reaction stirred for a further 15 minutes. The reaction was then concentrated, the residue redissolved in $CH_2Cl_2$, washed with saturated $NaHCO_3$, dried ($Na_2SO_4$) and concentrated. Purification by flash column chromatography (CH2Cl2: MeOH 9:1) afforded the title product (0.7 g, 44%) as a brown oil. MS: 275.2 (MH+).

B) 3 Methyl-(R)-pyrrolidin-3-yl-(tetrahydro-pyran-4-yl)-amine

A suspension of intermediate 18A (0.68 g, 2 mmol), palladium hydroxide on charcoal (0.1 g), cyclohexene (1 ml) in EtOH (10 ml) was heated at reflux for 2 h. The reaction was then filtered through Hyflo and concentrated to afford the title compound (0.4 g, 91%) as a brown gum. MS: 185.2 (MH+).

Intermediate 19

Methyl-(S)-pyrrolidin-3-yl-(tetrahydro-pyran-4-yl)-amine

The title compound was prepared in analogy to intermediate 18 starting from (S)-1-benzyl-pyrrolidin-3-ylamine. MS: 185.2 (MH+).

Intermediate 20

(R)-4-Pyrrolidin-3-yl-morpholine dihydrochloride

A) 4-((R)-1-Benzyl-pyrrolidin-3-yl)-morpholine

To a solution of 1,4-anhydroerythritol (1.9 g, 18 mmol) in water (10 ml) was added sodium periodate (0.7 g, 18 mmol) and the reaction stirred for 16 h. Acetonitrile (10 ml) was added to the mixture and the reaction was filtered to remove precipitated salts. (R)-1-benzyl-pyrrolidin-3-ylamine (1.0 g, 6 mmol) was added as a solution in acetonitrile (5 ml) to the filtrate, followed by sodium cyanoborohydride (1.1 g, 18 mmol). The reaction was stirred for 10 minutes after which time the reaction the acetonitrile removed by evaporation, the mixture made basic by addition of $NaHCO_3$, and repeatedly extracted with $CH_2Cl_2$. The combined organic extracts were dried ($Na_2SO_4$) and concentrated. Purification by flash column chromatography ($CH_2Cl_2$:MeOH 9:1) afforded the title product (0.4 g, 28%) as a brown gum. MS: 247.2 (MH+).

B) (R)-4-Pyrrolidin-3-yl-morpholine dihydrochloride

To a solution of intermediate 20A (0.4 g, 2 mmol) in MeOH (10 ml) was added palladium on charcoal (0.1 g) and the mixture made acidic by addition of 25% HCl. The mixture was stirred under 1 atmosphere of hydrogen for 16 h, after which time the reaction was filtered through Hyflo and concentrated to afford the title compound (0.3 g, 86%) as a brown gum. MS: 156.9 (MH+).

Intermediate 21

N-((trans)-4-Hydroxy-pyrrolidin-3-yl)-acetamide hydrochloride

A) N-((trans)-1-Benzyl-4-hydroxy-pyrrolidin-3-yl)-acetamide

To a solution of (trans)-4-azido-1-benzyl-pyrrolidin-3-ol (0.6 g, 3 mmol) (prepared as described in J. Med. Chem 1990, 33, 5, 1344) in MeOH (10 ml) was added Rainey nickel (0.5 g) and the reaction was stirred under one atmosphere of hydrogen for 1 h. The reaction was then filtered through Hyflo and concentrated. The residue was redissolved in $CH_2Cl_2$ (5 ml) and added to saturated $NaHCO_3$ (5 ml) and stirred vigorously while acetic anhydride (0.2 ml, 2 mmol) was added. The reaction was stirred for 15 minutes after which time the organic was separated, were dried ($Na_2SO_4$) and concentrated. Purification by flash column chromatography (CH2Cl2:MeOH 9:1) afforded the title product (0.4 g, 68%). MS: 235.1 (MH$^+$).

B) N-((trans)-4-Hydroxy-pyrrolidin-3-yl)-acetamide hydrochloride

The title product was prepared from intermediate 21A by hydrogenation in a manner identical to intermediate 20. MS: 145.1 (MH$^+$).

Intermediate 22

3-Methyl-pyrrolidine

3-Methyl-pyrrolidine was prepared as described in J. Med. Chem. 2000, 43, 23, 4388.

Intermediate 23

(trans)-4-Methyl-pyrrolidin-3-ol hydrochloride

The title compound was prepared from (trans)-1-Benzyl-4-methyl-pyrrolidin-3-ol (described in J. Med. Chem. 1992, 35, 22, 4205) by hydrogenation in an analogous manner to intermediate 20. MS: 102.2 (MH$^+$).

Intermediate 24

(cis)-4-Methyl-pyrrolidin-3-ol

A) (trans)-3-Hydroxy-4-methyl-pyrrolidine-1-carboxylic acid tert-butyl ester To a solution of intermediate 23 (0.5 g, 4 mmol) in CH$_2$Cl$_2$ (10 ml) and triethylamine (1 ml, 7 mmol) was added Boc anhydride (0.8 g, 4 mmol) and the reaction stirred for 2 h after which time it was washed with saturated NaHCO3, dried (Na$_2$SO$_4$) and concentrated affording the title product (0.8 g, quant.). MS: 202.4 (MH$^+$).

B) (cis)-3-Methyl-4-(4-nitro-benzoyloxy)-pyrrolidine-1-carboxylic acid tert-butyl ester To a solution of intermediate 24A (0.8 g, 4 mmol), triphenylphosphine (1.1 g, 4 mmol), 4-nitrobenzoic acid (0.7 g, 4 mmol) in toluene (10 ml) cooled to 0° C. is added diisopropylazodicarboxylate (0.9 ml, 4 mmol) dropwise. The reaction is then allowed to reach room temperature and stirred for 16 h after which time the reaction mixture was absorbed onto silica gel and purified by flash column chromatography (EtOAc:n-heptane 2:8). The title product was thus obtained as a white solid (1.0 g, 79%). MS: 351.3 (MH$^+$).

C) (cis)-3-Hydroxy-4-methyl-pyrrolidine-1-carboxylic acid tert-butyl ester

Intermediate 24B (1.0 g, 3 mmol) was dissolved in MeOH (10 ml) and sodium hydroxide (1.5 ml, 6M, 9 mmol) and the mixture heated to reflux for 1 h. The methanol was then evaporated and the residue redissolved in EtOAc, washed with saturated NaHCO3, dried (Na$_2$SO$_4$). Purification by flash column chromatography (CH$_2$Cl$_2$:MeOH 98:2) afforded the title product (0.6 g, quant.) as a colourless gum. MS: 202.4 (MH$^+$).

D) ((cis)-4-Methyl-pyrrolidin-3-ol hydrochloride

To a solution of intermediate 24C (0.6 g, 3 mmol) in dioxane (3 ml) was added hydrochloric acid (3 ml, 4N in dioxane, 12 mmol) and the reaction stirred for 2 h, after which time the reaction was concentrated affording the titled product (0.4 g, quant.) as a white powder. MS: 102.1 (MH$^+$).

Intermediate 25

3-Methyl-pyrrolidin-3-ol hydrochloride

A) 1-Benzyl-3-methyl-pyrrolidin-3-ol

Benzyl-3-methyl-pyrrolidin-3-ol was prepared as described in Tett Lett 1996, 37, 8, 1297, by addition of 1-benzylpyrolidin-3-one to methyl magnesium chloride.

B) 3-Methyl-pyrrolidin-3-ol hydrochloride

To a solution of intermediate 25A (2.0 g, 11 mmol) in MeOH (20 ml), was added 25% hydrochloric acid to acidify the reaction followed by palladium acetate (50 mg). Hydrogen was gently bubbled into the reaction while it was agitated in a sonication bath for a period of 2 h after which time the reaction was filtered through Hyflo and concentrated to afford the title product (1.5 g, quant) as a brown solid. MS: 102.1 (MH$^+$).

Intermediate 26

(3R,5S)-5-Methyl-pyrrolidin-3-ol hydrochloride

The title compound was prepared by treatment of (2S,4R)-4-Hydroxy-2-methyl-pyrrolidine-1-carboxylic acid tert-butyl ester (described in J. Med. Chem 1988, 31, 8, 1598) with hydrochloric acid analogously to intermediate 24. MS: 102.2 (MH$^+$).

Intermediate 27

(3R,5R)-5-Methyl-pyrrolidin-3-ol hydrochloride

The title compound was prepared by treatment of (2R,4R)-4-Hydroxy-2-methyl-pyrrolidine-1-carboxylic acid tert-butyl ester (described in J. Med. Chem 1988, 31, 8, 1598) with hydrochloric acid analogously to intermediate 24. MS: 102.2 (MH$^+$).

Intermediate 28

(3S,5S)-5-Methyl-pyrrolidin-3-ol hydrochloride

The title compound was prepared by treatment of (2S,4S)-4-Hydroxy-2-methyl-pyrrolidine-1-carboxylic acid tert-butyl ester (described in J. Am. Chem. Soc. 2006, 128, 4, 1040) with hydrochloric acid analogously to intermediate 24. MS: 102.4 (MH$^+$).

Intermediate 29

(3S,5R)-5-Methyl-pyrrolidin-3-ol hydrochloride

The title compound was prepared by treatment of (2S,4R)-4-Hydroxy-2-methyl-pyrrolidine-1-carboxylic acid tert-butyl ester (described in J. Am. Chem. Soc. 2006, 128, 4, 1040) with hydrochloric acid analogously to intermediate 24. MS: 102.2 (MH$^+$).

Intermediate 30

((2S,3R)-2-Methyl-pyrrolidin-3-ol hydrochloride

To a solution of (2S,3R)-1-benzyl-3-benzyloxy-2-methyl-pyrrolidine (1.5 g, 5 mmol) (prepared as described in Tetrahedron 1998, 54, 12547) in MeOH (10 ml) was added 25% hydrochloric acid to acidify and palladium on charcoal (0.5 g). The reaction was stirred under an atmosphere of hydrogen for 16 h after which time it was filtered through Hyflo and concentrated to afford the titled product (0.6 g, 75%) as a gum. MS: 102.2 ($MH^+$).

Intermediate 31

(trans)-3-Pyrrolidin-1-yl-piperidin-4-ol hydrochloride

The titled product was prepared by deprotection of (trans)-4-hydroxy-3-pyrrolidin-1-yl-piperidine-1-carboxylic acid tert-butyl ester (described in Heterocycles 1994, 39, 1, 163) with hydrochloric acid analogously to intermediate 30. MS: 171.0 ($MH^+$).

Intermediate 32

1-Piperidin-4-yl-imidazolidin-2-one

Prepared following the protocol published in WO2005/101989 (A2)

Intermediate 33

1,3,8-Triaza-spiro[4.5]decane-2,4-dione

Prepared according to the procedure published in J. Org. Chem. 1996, 61, 22, 7650-7651.

Intermediate 34

1-Oxa-3,8-diaza-spiro[4.5]decan-2-one

Prepared according to the procedure published in J. Med. Chem. 1995, 38, 3772-3779.

Intermediate 35

2,8-Diaza-spiro[4.5]decane-1,3-dione

Prepared according to the procedure published in J. Med. Chem. 1995, 38, 3772-3779.

Intermediate 36 cis-(3-Methoxy-tetrahydro-pyran-4-yl)-methyl-amine

A slurry of 3-methoxy-tetrahydro-pyran-4-one (0.4 g, 3 mmol-described in WO03/093266(A1)), ammonium formate (1.9 g, 30 mmol), 10% palladium on charcoal (1 g) in water:MeOH (1:5, 6 ml) was stirred overnight after which time it was filtered through Hyflo, the mixture concentrated to remove the MeOH, the residue taken up in $Et_2O$, dried ($Na_2SO_4$) and concentrated to afford the title product (0.2 g, 49%) as a yellow oil (contaminated by 10-20% of the trans isomer). $^1$H NMR (300 MHz, $CDCl_3$) (cis isomer) δ 1.60-1.80 (2H, m), 2.95-3.00 (1H, m), 3.22-3.43 (5H, m). 3.82-3.95 (1H, m), 4.01-4.13 (1H, m).

Intermediate 37

(R)-Pyrrolidin-3-yl-(tetrahydro-pyran-4-yl)-carbamic acid tert-butyl ester

To a solution of (R)-1-benzyl-pyrrolidin-3-ylamine (1.0 g, 6 mmol), tetrahydro-4H-pyran-4-one (0.6 g, 6 mmol) in $CH_2Cl_2$ (15 ml) was added acetic acid (0.7 ml, 11 mmol) and sodium triacetoxyborohydride (1.4 g, 7 mmol) and the reaction stirred for 1 h. The mixture was then washed with saturated $NaHCO_3$ and dried ($Na_2SO4$). Boc anhydride (1.3 g, 6 mmol) was then added and the reaction stirred for a further hour after which time it was partially concentrated and through a plug of silica ($CH_2Cl_2$:MeOH 95:5) and concentrated. To the residue (0.3 g, 1 mmol), cyclohexene (1 ml) in EtOH (10 ml) was added palladium hydroxide on charcoal (0.1 g) and the mixture was heated to reflux for 2 h after which time the reaction was filtered through Hyflo and concentrated to afford the title product (0.2 g, 85%) as an orange gum. MS: 271.2 ($MH^+$)

Intermediate 38

(2-Methyl-1-piperidin-4-yl-pyrrolidin-2-yl)-methanol dihydrochloride

A) 4-(2-Hydroxy-2-methyl-2-methyl-pyrrolidin-1-yl)-piperidine-1-carboxylic acid tert-butyl ester To a solution of (2-Methyl-pyrrolidin-2-yl)-methanol (0.2 g, 2 mmol) (prepared by reduction of alpha-methyl-DL-proline), 4-boc-piperidinone (1 g, 5 mmol), acetic acid (0.1 ml, 2 mmol) in $CH_2Cl_2$ (10 ml) was added sodium triacetoxyborohydride (1.1 g, 5 mmol) and the reaction stirred for 3 h. The reaction was then diluted with $CH_2Cl_2$, washed with saturated $NaHCO_3$, dried ($Na_2SO_4$) and concentrated. Purification by flash column chromatography (EtOAc:n-heptane 1:1) afforded the title product (0.05 g, 10%) as a light brown gum. MS: 299.2 ($MH^+$)

B) (2-Methyl-1-piperidin-4-yl-pyrrolidin-2-yl)-methanol dihydrochloride

To a solution of intermediate 38A (0.05 g, 0.1 mmol) in dioxane (1 ml) was added hydrochloric acid (2 ml, 4N in dioxane) and the reaction stirred for 1 h. The reaction was then concentrated to afford the titled product (0.05 g, quant) as a light brown gum. MS: 199.1 ($MH^+$)

Intermediate 39

1-(1-{3-[(E)-2-(4-Chloro-phenyl)-vinyl]-phenyl}-3,5-dimethyl-1H-pyrazole-4-carbonyl)-pyrrolidin-3-ylamine hydrochloride A) [1-(1-{3-[(E)-2-(4-Chloro-phenyl)-vinyl]-phenyl}-3,5-dimethyl-1H-pyrazole-4-carbonyl)-pyrrolidin-3-yl]-carbamic acid tert-butyl ester To a solution of intermediate 4 (1.1 g, 3 mmol), 3-(tert-butoxycarbonylamino)-pyrolidine (0.6 g, 3 mmol), EDCI (0.69 g, 4 mmol) and HOBT (0.4 g, 3 mmol) in DMF (20 ml) was added triethylamine (0.6 ml, 5 mmol) and the reaction stirred for 2 h. The reaction was then concentrated, redissolved in $CH_2Cl_2$, washed with 10% citric acid solution, saturated $NaHCO_3$, dried ($Na_2SO_4$) and concentrated. Purification by flash column chromatography (EtOAc:n-heptane 4:1-1:0 gradient) afforded the title product (1.3 g, 82%) as a white foam. MS: 521.3 (M+, 1 Cl)

B) 1-(1-{3-[(E)-2-(4-Chloro-phenyl)-vinyl]-phenyl}-3,5-dimethyl-1H-pyrazole-4-carbonyl)-pyrrolidin-3-yl-amine hydrochloride Intermediate 39A was treated with hydrochloric acid in a similar manner to intermediate 38 affording the title product as a white solid. MS: 421.3 (M+, 1 Cl)

Example 1

(1-{3-[(E)-2-(4-Chloro-phenyl)-vinyl]-phenyl}-3,5-diethyl-1H-pyrazol-4-yl)-[4-(2-hydroxy-ethyl)-[1,4]diazepan-1-yl]-methanone

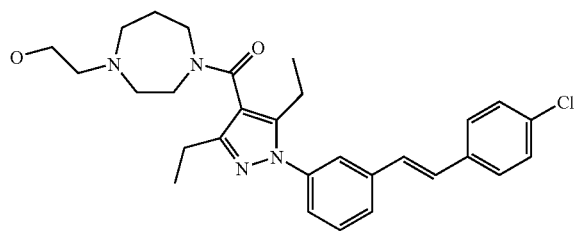

A solution of 0.20 g (0.50 mmol) of 1-{3-[(E)-2-(4-chloro-phenyl)-vinyl]-phenyl}-3,5-diethyl-1H-pyrazole-4-carboxylic acid (intermediate 1) and 0.21 g (0.50 mmol) of HATU were dissolved in 8 ml of DMF at RT. While stirring, 0.16 g=0.22 ml (1.60 mmol) of Et₃N were added drop by drop. After 30 min, a solution of 0.076 g (0.50 mmol) of 2-[1,4]diazepan-1-yl-ethanol in 2 ml of DMF were added drop by drop and stirring was continued for 20 hours at RT. The reaction mixture was poured into crashed ice and extracted twice with EtOAc; the organic phases were washed with water, dried over magnesium sulfate, filtered and evaporated. The residue was purified by flash column chromatography (CH₂Cl₂/MeOH 1:0-9:1) to afford the title compound as colorless oil. MS: 507.4 (MH+, 1 Cl).

Example 2

(1-{3-[(E)-2-(4-Chloro-phenyl)-vinyl]-phenyl}-3,5-diethyl-1H-pyrazol-4-yl)-[4-(1-methyl-piperidin-4-ylmethyl)-piperazin-1-yl]-methanone

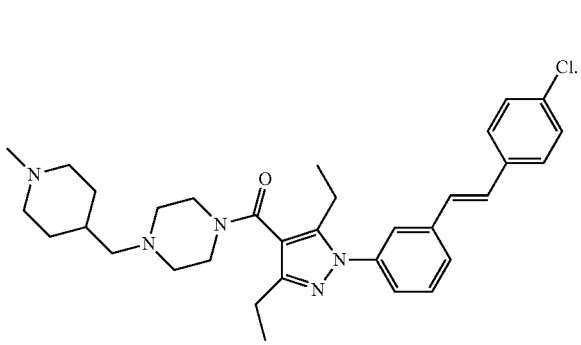

A solution of 0.40 g (1.10 mmol) of 1-{3-[(E)-2-(4-chloro-phenyl)-vinyl]-phenyl}-3,5-diethyl-1H-pyrazole-4-carboxylic acid (intermediate 1) and 0.18 g (1.1 mmol) of 2-chloro-4,6-dimethoxy-[1,3,5]triazine were dissolved in 10 ml of MeCN. The solution was then cooled down to 0° C. and 0.32 g=0.35 ml (3.2 mmol) of N-methylmorpholine was added drop by drop. After 2 hours stirring at 0° C., a solution of 0.21 g (1.1 mmol) 1-(1-methyl-piperidin-4-ylmethyl)-piperazine in 3 ml of MeCN was added drop by drop. Then, the mixture was warmed up to RT and stirring continued for 20 hours. Subsequently, it was poured into crashed ice and extracted twice with EtOAc; the organic phases were washed with water, dried over magnesium sulfate, filtered and evaporated. The residue was purified by flash column chromatography (CH₂Cl₂/MeOH 1:0-7.5:2.5) to afford the title compound as colorless solid. MS: 560.2 (MH+, 1 Cl).

Example 3

(1-{3-[(E)-2-(4-Chloro-phenyl)-vinyl]-phenyl}-3,5-diethyl-1H-pyrazol-4-yl)-(4-pyrrolidin-1-yl-piperidin-1-yl)-methanone

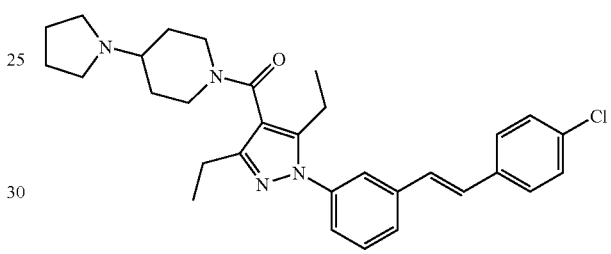

In analogy to the procedure described for example 2, 1-{3-[(E)-2-(4-chloro-phenyl)-vinyl]-phenyl}-3,5-diethyl-1H-pyrazole-4-carboxylic acid (intermediate 1) and 4-pyrrolidin-1-yl-piperidine gave the title compound as colorless oil. MS: 517.3 (MH+, 1 Cl).

Example 4

[rac]-(1-{3-[(E)-2-(4-Chloro-phenyl)-vinyl]-phenyl}-3,5-diethyl-1H-pyrazol-4-yl)-(3-diethylamino-pyrrolidin-1-yl)-methanone

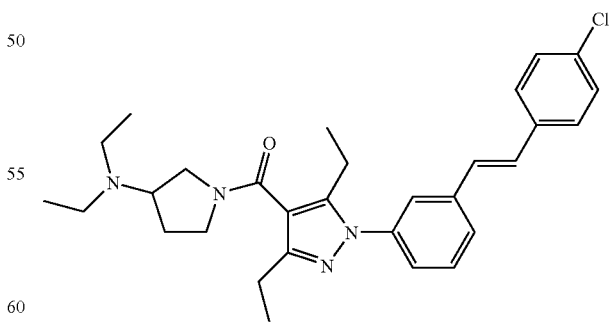

In analogy to the procedure described for example 2, 1-{3-[(E)-2-(4-chloro-phenyl)-vinyl]-phenyl}-3,5-diethyl-1H-pyrazole-4-carboxylic acid (intermediate 1) and [rac]-diethyl-pyrrolidin-3-yl-amine gave the title compound as colorless oil. MS: 505.3 (MH+, 1 Cl).

Example 5

[3,5-Diethyl-1-(3-hex-1-ynyl-phenyl)-1H-pyrazol-4-yl]-(4-pyrrolidin-1-yl-piperidin-1-yl)-methanone

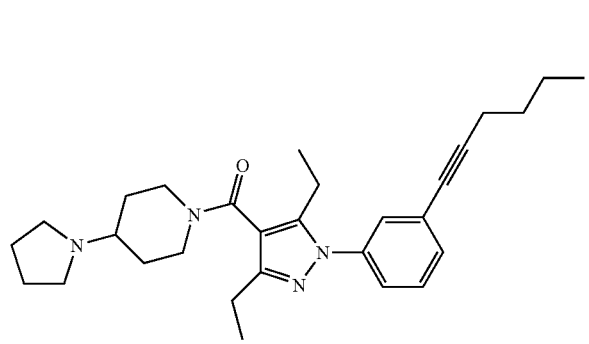

In analogy to the procedure described for example 1,3,5-diethyl-1-(3-hex-1-ynyl-phenyl)-1H-pyrazole-4-carboxylic acid (intermediate 2) and 4-pyrrolidin-1-yl-piperidine gave the title compound as colorless oil. MS: 461.5 (MH$^+$).

Example 6

[3,5-Diethyl-1-(3-hexyl-phenyl)-1H-pyrazol-4-yl]-[4-(2-hydroxy-ethyl)-[1,4]diazepan-1-yl]-methanone

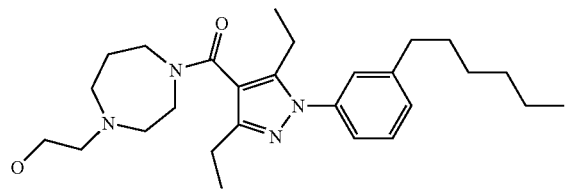

A) [3,5-Diethyl-1-(3-hex-1-ynyl-phenyl)-1H-pyrazol-4-yl]-[4-(2-hydroxy-ethyl)-[1,4]diazepan-1-yl]-methanone In analogy to the procedure described for example 1,3,5-diethyl-1-(3-hex-1-ynyl-phenyl)-1H-pyrazole-4-carboxylic acid (intermediate 2) and 2-[1,4]diazepan-1-yl-ethanol gave the title compound as light yellow oil. MS: 451.3 (MH$^+$).

B) [3,5-Diethyl-1-(3-hexyl-phenyl)-1H-pyrazol-4-yl]-[4-(2-hydroxy-ethyl)-[1,4]diazepan-1-yl]-methanone 0.027 g of Pd—C (10%) was added to a solution of 0.11 g (0.30 mmol) of [3,5-diethyl-1-(3-hex-1-ynyl-phenyl)-1H-pyrazol-4-yl]-[4-(2-hydroxy-ethyl)-[1,4]diazepan-1-yl]-methanone in 5 ml of MeOH and the reaction mixture was then hydrogenated with H$_2$ (1 bar) at RT for 1 hour. After removal the catalyst by filtration, the solvent was evaporated completely to afford the title compound as light yellow oil. MS: 455.3 (MH$^+$).

Example 7

[3,5-Diethyl-1-(3-hexyl-phenyl)-1H-pyrazol-4-yl]-(4-pyrrolidin-1-yl-piperidin-1-yl)-methanone

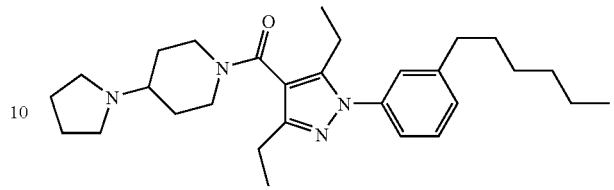

In analogy to the procedure described for example 6B, [3,5-diethyl-1-(3-hex-1-ynyl-phenyl)-1H-pyrazol-4-yl]-(4-pyrrolidin-1-yl-piperidin-1-yl)-methanone (example 5) was hydrogenated to give the title compound as yellow oil. MS: 465.5 (MH$^+$).

Example 8

[rac]-(3-Diethylamino-pyrrolidin-1-yl)-[3,5-diethyl-1-(3-hexyl-phenyl)-1H-pyrazol-4-yl]-methanone

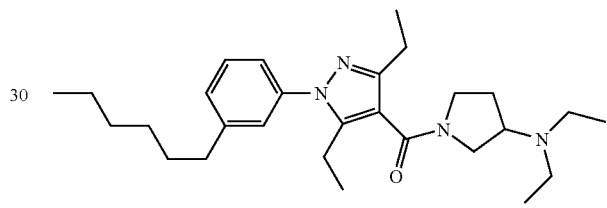

In analogy to the procedure described for example 1,3,5-diethyl-1-(3-hex-1-ynyl-phenyl)-1H-pyrazole-4-carboxylic acid (intermediate 2) and [rac]-diethyl-pyrrolidin-3-yl-amine gave [rac]-(3-diethylamino-pyrrolidin-1-yl)-[3,5-diethyl-1-(3-hex-1-ynyl-phenyl)-1H-pyrazol-4-yl]-methanone as light red oil [MS: 449.3 (MH$^+$)], which was subsequently hydrogenated in analogy to the procedure described for example 6B to yield the title compound as light yellow solid. MS: 453.5 (MH$^+$).

Example 9

(1-{3-[(E)-2-(4-Chloro-phenyl)-vinyl]-phenyl}-3,5-bis-methoxymethyl-1H-pyrazol-4-yl)-[4-(2-hydroxy-ethyl)-[1,4]diazepan-1-yl]-methanone

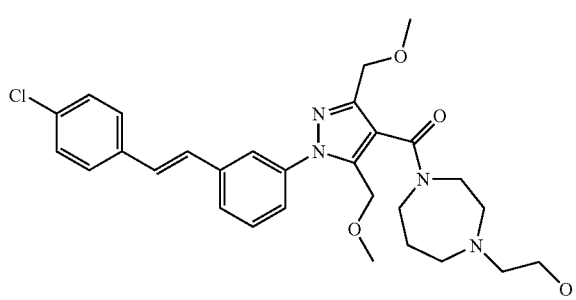

In analogy to the procedure described for example 1, 1-{3-[(E)-2-(4-chloro-phenyl)-vinyl]-phenyl}-3,5-bis-methoxymethyl-1H-pyrazole-4-carboxylic acid (intermediate 3) and 2-[1,4]diazepan-1-yl-ethanol gave the title compound as brown oil. MS: 539.3 (MH+, 1 Cl).

Example 10

(1-{3-[(E)-2-(4-Chloro-phenyl)-vinyl]-phenyl}-3,5-bis-methoxymethyl-1H-pyrazol-4-yl)-(4-pyrrolidin-1-yl-piperidin-1-yl)-methanone

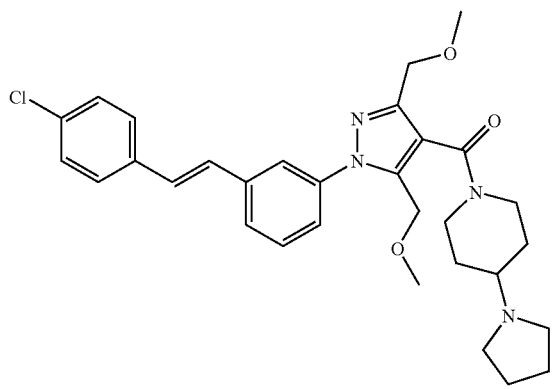

In analogy to the procedure described for example 1, 1-{3-[(E)-2-(4-chloro-phenyl)-vinyl]-phenyl}-3,5-bis-methoxymethyl-1H-pyrazole-4-carboxylic acid (intermediate 3) and 4-pyrrolidin-1-yl-piperidine gave the title compound as brown solid. MS: 549.3 (MH+, 1 Cl).

Example 11

[rac]-(1-{3-[(E)-2-(4-Chloro-phenyl)-vinyl]-phenyl}-3,5-bis-methoxymethyl-1H-pyrazol-4-yl)-(3-diethylamino-pyrrolidin-1-yl)-methanone

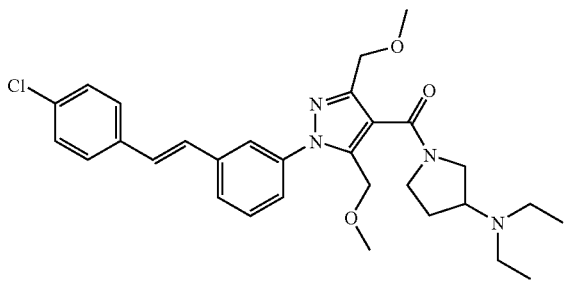

In analogy to the procedure described for example 1, 1-{3-[(E)-2-(4-chloro-phenyl)-vinyl]-phenyl}-3,5-bis-methoxymethyl-1H-pyrazole-4-carboxylic acid (intermediate 3) and [rac]-diethyl-pyrrolidin-3-yl-amine gave the title compound as brown solid. MS: 537.3 (MH+, 1 Cl).

Example 12

[5-(3-benzofuran-2-yl-phenyl)-2-methyl-2H-pyrazol-3-yl]-(3-diethylamino-pyrrolidin-1-yl)-methanone

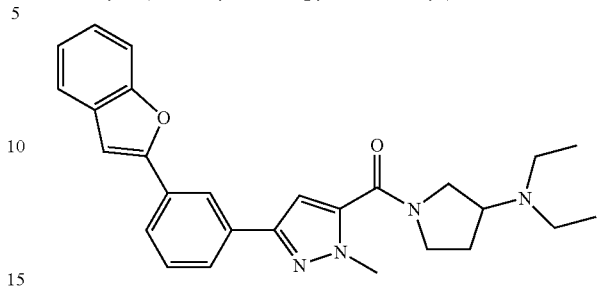

A] 5-(3-bromo-phenyl)-2-methyl-2H-pyrazole-3-carboxylic acid methyl ester and 5-(3-bromo-phenyl)-1-methyl-1H-pyrazole-3-carboxylic acid methyl ester 3.00 g (10.52 mmol) of 4-(3-bromo-phenyl)-2,4-dioxo-butyric acid methyl ester were suspended in 16 ml of EtOH and 0.485 g (10.52 mmol) of methylhydrazine were added. The reaction was heated under reflux (65° C.) for 5 h. Then the solvent was evaporated and the residue was partitioned between aqueous 1N HCl/EtOAc (3×). The organic phases were washed with aqueous sat. NaCl, dried (Na$_2$SO$_4$) and evaporated. The crude product was purified by flash chromatography (SiO$_2$, n-heptane/EtOAc 99:1) to give 1.64 g (37%) of 5-(3-bromo-phenyl)-2-methyl-2H-pyrazole-3-carboxylic acid methyl ester (and ethyl ester) as white powder (MS: methyl ester 295.1 MH+, 1 Br; ethyl ester 309.1 MH+, 1 Br) and 1.11 g (28%) of 5-(3-bromo-phenyl)-1-methyl-1H-pyrazole-3-carboxylic acid methyl ester (and ethyl ester) as yellow oil (MS: methyl ester 295.1 MH+, 1 Br; ethyl ester 309.1 MH+, 1 Br).

B] 5-(3-benzofuran-2-yl-phenyl)-2-methyl-2H-pyrazole-3-carboxylic acid methyl ester 1.40 g (4.74 mmol) of 5-(3-bromo-phenyl)-2-methyl-2H-pyrazole-3-carboxylic acid methyl ester (6') (and ethyl ester) was dissolved in 15 ml of toluene and 1.6 ml of H$_2$O. Then 1.54 g (9.49 mmol) of benzo[b]furan-2-boronic acid, 5.42 g (25.52 mmol) of K$_3$PO$_4$, 0.29 g (1.04 mmol) of tricyclohexylphosphine and 0.117 g (0.52 mmol) of palladium-II-acetate were added. The reaction mixture was degassed (argon) several times at each addition. The reaction was heated (100° C.) for 24 h. At RT, the mixture was partitioned between chilled water/EtOAc (3×). The organic phases were washed with water, with aqueous sat. NaHCO$_3$, dried (Na$_2$SO$_4$), filtered (black palladium complex stayed with Na$_2$SO$_4$) and evaporated. Then the residual product was dissolved in hot CH$_2$Cl$_2$ and crystallized at RT. It was filtered to give 0.918 g (58%) of 5-(3-benzofuran-2-yl-phenyl)-2-methyl-2H-pyrazole-3-carboxylic acid methyl ester as white powder. MS: 332.2 (M+).

C] 5-(3-benzofuran-2-yl-phenyl)-2-methyl-2H-pyrazole-3-carboxylic acid

A suspension of 0.90 g (2.71 mmol) of 5-(3-benzofuran-2-yl-phenyl)-2-methyl-2H-pyrazole-3-carboxylic acid methyl ester (6'A) in 8.50 ml of DMSO was treated at RT with 1.35 ml (5.42 mmol) of aqueous 1N NaOH. After 2 h, reaction was diluted with chilled water and extracted 1× with Et$_2$O. The water phase was acidified with aqueous 10% KHSO$_4$ and extracted with Et$_2$O (2×). These organic phases were washed with aqueous 10% NaCl, dried (Na$_2$SO$_4$) and evaporated to give 0.84 g (97%) of the title compound as white powder. MS: 317.1 (M−H⁻).

D] [5-(3-benzofuran-2-yl-phenyl)-2-methyl-2H-pyrazol-3-yl]-(3-diethylamino-pyrrolidin-1-yl)-methanone A solution of 0.124 g (0.39 mmol) of 5-(3-benzofuran-2-yl-phenyl)-2-methyl-2H-pyrazole-3-carboxylic acid in 1.28 ml of DMF was treated with 0.063 g (0.39 mmol) of CDI. After 4 h, 0.055 g (0.39 mmol) of 3-(diethylamino)pyrrolidine and 0.217 ml (1.56 mmol) of Et$_3$N in 1.28 ml of DMF were added and stirring was continued for 2 h. The solution was partitioned between aqueous saturated NaHCO$_3$/Et$_2$O (3×). The organic phases were washed with aqueous saturated NaHCO$_3$ and aqueous 10% NaCl, dried (Na$_2$SO$_4$) and evaporated. The crude product was crystallized with Et$_2$O/pentane to give 0.130 g (75%) of [5-(3-benzofuran-2-yl-phenyl)-2-methyl-2H-pyrazol-3-yl]-(3-diethylamino-pyrrolidin-1-yl)-methanone as light pink powder. MS: 443.2 (MH⁺).

Example 13

[5-(3-Benzofuran-2-yl-phenyl)-2-methyl-2H-pyrazol-3-yl)-[4-(2-hydroxy-ethyl)-[1,4]diazepan-1-yl]-methanone

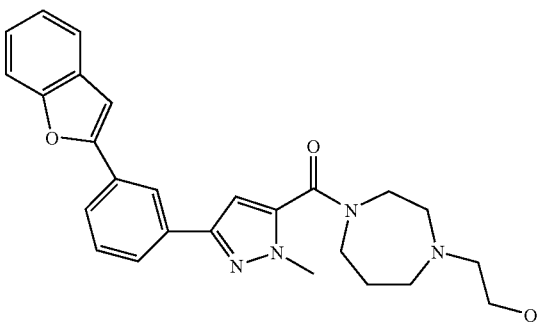

In analogy to the procedure described in Example 16D], 5-(3-benzofuran-2-yl-phenyl)-2-methyl-2H-pyrazole-3-carboxylic acid (Example 12C]) and 2-(1,4-diazepan-1-yl)ethan-1-ol with DCC and catalytic amount of DMAP gave the title compound in 32% yield as white foam. MS: 445.1 (MH⁺).

Example 14

[5-(3-benzofuran-2-yl-phenyl)-1-methyl-1H-pyrazol-3-yl]-(3-diethylamino-pyrrolidin-1-yl)-methanone

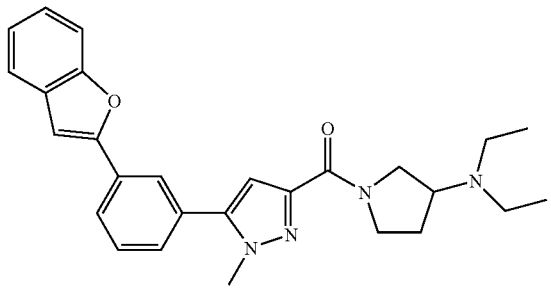

A] 5-(3-bromo-phenyl)-1-methyl-1H-pyrazole-3-carboxylic acid and 5-(3-benzofuran-2-yl-phenyl)-1-methyl-1H-pyrazole-3-carboxylic acid 0.49 g (1.66 mmol) of 5-(3-bromo-phenyl)-1-methyl-1H-pyrazole-3-carboxylic acid methyl ester (6) (and ethyl ester) (Example 12A]) was dissolved in 5.28 ml of toluene and 2.40 ml of H$_2$O. Then 0.538 g (3.32 mmol) of benzo[b]furan-2-boronic acid, 1.896 g (8.93 mmol) of K$_3$PO$_4$, 0.102 g (0.37 mmol) of tricyclohexylphosphine and 0.042 g (0.19 mmol) of palladium-II-acetate were added. The reaction mixture was degassed (argon) several times at each addition. Then it was heated (100° C.) for 24 h. At RT, the mixture was partitioned between chilled water/EtOAc (3×). The organic phases were washed with water, with aqueous sat. NaHCO$_3$, dried (Na$_2$SO$_4$) and evaporated to give 0.256 g of a mixture 1:1 of starting material and expected benzofuran esters (¹H-NMR).

The aqueous phase was then acidified with aqueous 10% KHSO$_4$ and extracted with CH$_2$Cl$_2$. These organic phases were washed with aqueous 10% KHSO$_4$, dried (Na$_2$SO$_4$) and evaporated to give 0.321 g of a mixture 1:1 of 5-(3-bromo-phenyl)-1-methyl-1H-pyrazole-3-carboxylic acid (MS: 279.0 M−H⁻, 1 Br) and 5-(3-benzofuran-2-yl-phenyl)-1-methyl-1H-pyrazole-3-carboxylic acid (MS: 317.1 M−H⁻) as light brown gum.

B] [5-(3-bromo-phenyl)-1-methyl-1H-pyrazol-3-yl]-(3-diethylamino-pyrrolidin-1-yl)-methanone and [5-(3-benzofuran-2-yl-phenyl)-1-methyl-1H-pyrazol-3-yl]-(3-diethylamino-pyrrolidin-1-yl)-methanone (The equivalences of reagents and the yield were calculated for the 5-(3-bromo-phenyl)-1-methyl-1H-pyrazole-3-carboxylic acid as starting material.)

In analogy to the procedure described in Example 12D], the mixture 1:1 of bromo and benzofuran acids and 3-(diethylamino)pyrrolidine gave [5-(3-bromo-phenyl)-1-methyl-1H-pyrazol-3-yl]-(3-diethylamino-pyrrolidin-1-yl)-methanone (MS: 405.2 MH⁺, 1 Br) and [5-(3-benzofuran-2-yl-phenyl)-1-methyl-1H-pyrazol-3-yl]-(3-diethylamino-pyrrolidin-1-yl)-methanone (MS: 443.2 MH⁺) in 80% yield as light brown viscous oil.

C] [5-(3-benzofuran-2-yl-phenyl)-1-methyl-1H-pyrazol-3-yl]-(3-diethylamino-pyrrolidin-1-yl)-methanone (The equivalences of reagents and the yield were calculated for [5-(3-bromo-phenyl)-1-methyl-1H-pyrazol-3-yl]-(3-diethylamino-pyrrolidin-1-yl)-methanone as starting material.) 0.370 g (0.91 mmol) of the mixture [5-(3-bromo-phenyl)-1-methyl-1H-pyrazol-3-yl]-(3-diethylamino-pyrrolidin-1-yl)-methanone and [5-(3-benzofuran-2-yl-phenyl)-1-methyl-1H-pyrazol-3-yl]-(3-diethylamino-pyrrolidin-1-yl)-methanone was dissolved in 8.00 ml of DMF. Then 0.189 g (1.14 mmol, 1.25 eq) of benzo[b]furan-2-boronic acid, 0.360 g (1.64 mmol, 1.80 eq) of K$_3$PO$_4$ and 0.105 g (0.09 mmol, 0.10 eq) of tetrakis-(triphenylphosphine)-palladium were added. The reaction mixture was degassed (argon) several times at each addition. It was heated (100° C.) for 24 h. At RT, the mixture was partitioned between aqueous sat. NaHCO$_3$/Et$_2$O (3×). The organic phases were washed with aqueous sat. NaHCO$_3$, dried (Na$_2$SO$_4$) and evaporated. Purification by flash chromatography (SiO$_2$, MeOH/CH$_2$Cl$_2$ 2:98) gave 0.299 g (73%) of title compound as brown foam. MS: 443.2 (MH$^+$).

Example 15

[5-(3-benzofuran-2-yl-phenyl)-1-methyl-1H-pyrazol-3-yl]-[4-(2-hydroxy-ethyl)-[1,4]diazepan-1-yl]-methanone

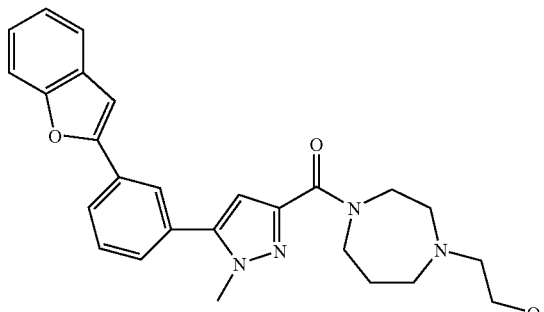

A] 5-(3-bromo-phenyl)-1-methyl-1H-pyrazole-3-carboxylic acid

In analogy to the procedure described in Example 12C], 5-(3-bromo-phenyl)-1-methyl-1H-pyrazole-3-carboxylic acid methyl ester (and ethyl ester) (Example 12A]) gave 5-(3-bromo-phenyl)-1-methyl-1H-pyrazole-3-carboxylic acid in quantitative yield as white gum. MS: 279.1 (M−H$^-$, 1 Br).

B] 5-(3-benzofuran-2-yl-phenyl-1-methyl-1H-pyrazole-3-carboxylic acid

In analogy to the procedure described in Example 13C], but with 2.8 eq of K$_3$PO$_4$ and an acidic extraction, 5-(3-bromo-phenyl)-1-methyl-1H-pyrazole-3-carboxylic acid and benzo[b]furan-2-boronic acid gave 5-(3-benzofuran-2-yl-phenyl)-1-methyl-1H-pyrazole-3-carboxylic acid in 55% yield as light yellow powder. MS: 317.1 (M−H$^-$).

C] [5-(3-benzofuran-2-yl-phenyl)-1-methyl-1H-pyrazol-3-yl]-[4-(2-hydroxy-ethyl)-[1,4]diazepan-1-yl]-methanone In analogy to the procedure described in Example 12D], 5-(3-benzofuran-2-yl-phenyl)-1-methyl-1H-pyrazole-3-carboxylic acid and 2-(1,4-diazepan-1-yl)ethan-1-ol gave [5-(3-benzofuran-2-yl-phenyl)-1-methyl-1H-pyrazol-3-yl]-[4-(2-hydroxy-ethyl)-[1,4]diazepan-1-yl]-methanone in 5% yield as light yellow oil. MS: 445.1 (MH$^+$).

Example 16

[5-(3-benzofuran-2-yl-phenyl)-1,4-dimethyl-1H-pyrazol-3-yl]-[4-(2-hydroxy-ethyl)-[1,4]diazepan-1-yl]-methanone

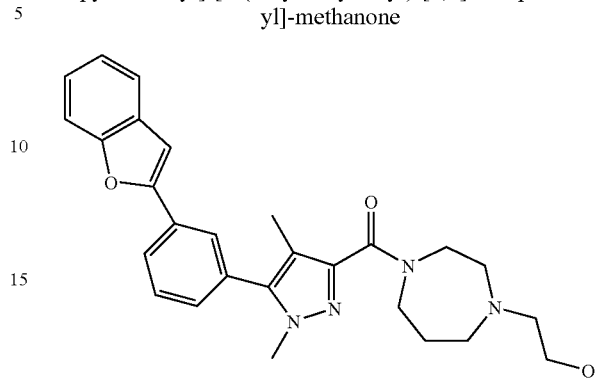

A] 5-(3-bromo-phenyl)-2,4-dimethyl-2H-pyrazole-3-carboxylic acid ethyl ester and 5-(3-bromo-phenyl)-1,4-dimethyl-1H-pyrazole-3-carboxylic acid ethyl ester 4.00 g (8.02 mmol) of 4-(3-bromo-phenyl)-3-methyl-2,4-dioxo-butyric acid ethyl ester (synthesized from 3'-bromopropiophenone and diethyl oxalate, following a procedure described in Ksander, Gary M.; McMurry, John E.; Johnson, Mark. A method for the synthesis of unsaturated carbonyl compounds. Journal of Organic Chemistry (1977), 42(7), 1180-5) were dissolved in 12.20 ml of MeOH and 0.37 g (8.02 mmol) of methylhydrazine were added. The reaction was heated under reflux (65° C.) for 1 h. Then the reaction was partitioned between chilled aqueous 1N HCl/EtOAc (3×). The organic phase was washed with aqueous 1N HCl, with aqueous sat. NaCl, dried (Na$_2$SO$_4$) and evaporated. The crude product was purified by flash chromatography (SiO$_2$, n-heptane/EtOAc 99:1) to give 0.61 g of 5-(3-bromo-phenyl)-2,4-dimethyl-2H-pyrazole-3-carboxylic acid ethyl ester as yellow oil (MS: 323.2 MH$^+$, Br) and 1.731 g of 5-(3-bromo-phenyl)-1,4-dimethyl-1H-pyrazole-3-carboxylic acid ethyl ester as yellow oil (MS: 323.2 MH$^+$, Br).

B] 5-(3-benzofuran-2-yl-phenyl)-1,4-dimethyl-1H-pyrazole-3-carboxylic acid ethyl ester In analogy to the procedure described in Example 14C] but with 2.8 eq of K$_3$PO$_4$, 5-(3-bromo-phenyl)-1,4-dimethyl-1H-pyrazole-3-carboxylic acid ethyl ester and benzo[b]furan-2-boronic acid gave 5-(3-benzofuran-2-yl-phenyl)-1,4-dimethyl-1H-pyrazole-3-carboxylic acid ethyl ester in 73% yield as light brown foam. MS: 361.4 (MH$^+$).

C] 5-(3-benzofuran-2-yl-phenyl)-1,4-dimethyl-1H-pyrazole-3-carboxylic acid

A suspension of 0.615 g (1.71 mmol) of 5-(3-benzofuran-2-yl-phenyl)-1,4-dimethyl-1H-pyrazole-3-carboxylic acid ethyl ester in 5.50 ml of DMSO was treated at RT with 0.85 ml (3.41 mmol) of aqueous 1N NaOH. After 2 h, reaction was heated at 45° C. for 30 min. Then it was diluted with chilled water and extracted with Et$_2$O. The water phase was acidified with aqueous 10% KHSO$_4$ and extracted with Et$_2$O (2×). These organic phases were washed with aqueous 10% NaCl, dried (Na$_2$SO$_4$) and evaporated to give 0.481 g (84%) of 5-(3-benzofuran-2-yl-phenyl)-1,4-dimethyl-1H-pyrazole-3-carboxylic acid as light brown powder. MS: 331.4 (M–H⁻).

D] [5-(3-benzofuran-2-yl-phenyl)-1,4-dimethyl-1H-pyrazol-3-yl]-[4-(2-hydroxy-ethyl)-[1,4]diazepan-1-yl]-methanone To a suspension of 0.060 g (0.18 mmol) of 5-(3-benzofuran-2-yl-phenyl)-1,4-dimethyl-1H-pyrazole-3-carboxylic acid in 2 ml of CH₂Cl₂ was added 0.031 g (0.22 mmol) of 2-(1,4-diazepan-1-yl)ethan-1-ol, diluted in 1.7 ml of CH₂Cl₂. This solution was treated at 0° C. with 0.048 g (0.23 mmol) of DCC. The reaction was allowed to warm up over night to RT, then partitioned between aqueous saturated NaHCO₃/EtOAc (3×). The organic phases were washed with aqueous saturated NaHCO₃, dried (Na₂SO₄) and evaporated. The residue was suspended in EtOAc and filtered to remove the DCC urea. Purification by flash chromatography (SiO₂—NH₂, n-heptane/EtOAc 1:4) gave 0.033 g (39%) of [5-(3-benzofuran-2-yl-phenyl)-1,4-dimethyl-1H-pyrazol-3-yl]-[4-(2-hydroxy-ethyl)-[1,4]diazepan-1-yl]-methanone as white oil. MS: 459.3 (MH⁺).

Example 17

[5-(3-benzofuran-2-yl-phenyl)-1,4-dimethyl-1H-pyrazol-3-yl]-[4-(2-hydroxy-ethyl)-piperazin-1-yl]-methanone

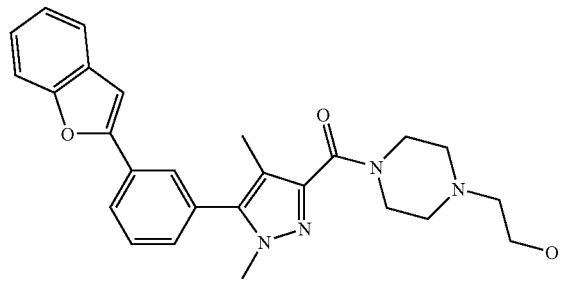

In analogy to the procedure described in Example 16D], 5-(3-benzofuran-2-yl-phenyl)-1,4-dimethyl-1-pyrazole-3-carboxylic acid (Example 16C]) and N-(2-hydroxyethyl)-piperazine gave the title compound in 5% yield as yellow solid. MS: 445.1 (MH⁺).

Example 18

[5-(3-Benzofuran-2-yl-phenyl)-1,4-dimethyl-1H-pyrazol-3-yl]-(4-morpholin-4-yl-piperidin-1-yl)-methanone

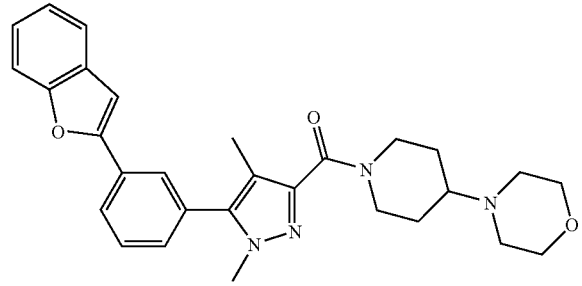

A suspension of 0.080 g (0.24 mmol) of 5-(3-benzofuran-2-yl-phenyl)-1,4-dimethyl-1H-pyrazole-3-carboxylic acid (Example 16C]) in 1.5 ml of CH₂Cl₂ was treated at RT with 1 drops of DMF. 0.02 ml (0.29 mmol, 1.2 eq) of oxalyl chloride in 0.5 ml CH₂Cl₂ were added dropwise and stirring was continued for 1 h. The solution was evaporated, redissolved in 1 ml of CH₂Cl₂, cooled (0° C.) and treated with a solution of 0.041 g (0.24 mmol, 1 eq) of 4-(piperidine-4-yl)-morpholine and 0.07 ml (0.48 mmol, 2 eq) of triethylamine in 0.5 ml of CH₂Cl₂. The reaction was stirred for 3 h at this temperature, then partitioned three times between EtOAc and aqueous saturated NaHCO₃, dried over Na₂SO₄ and evaporated to give 0.134 g (quant.) of the title compound as light yellow foam. MS: 485.3 (MH⁺).

Example 19

[5-(3-Benzofuran-2-yl-phenyl)-1,4-dimethyl-1H-pyrazol-3-yl]-[4-(3-hydroxy-propyl)-piperazin-1-yl]-methanone

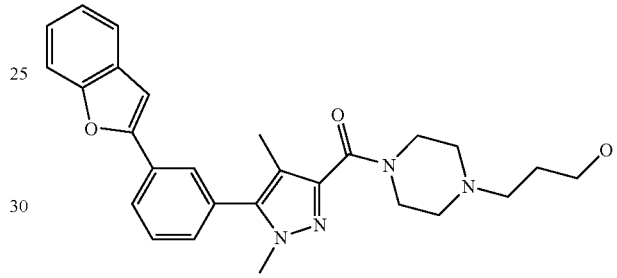

In analogy to the procedure described in Example 181, 5-(3-benzofuran-2-yl-phenyl)-1,4-dimethyl-1H-pyrazole-3-carboxylic acid (Example 16C]) and 1-piperazinepropanol gave after suspending in a small amount of EtOAc and filtration the title compound in 59% yield as light yellow powder. MS: 459.3 (MH⁺).

Example 20

[5-(3-Benzofuran-2-yl-phenyl)-1,4-dimethyl-1H-pyrazol-3-yl]-[4-(2-methoxy-ethyl)-piperazin-1-yl]-methanone

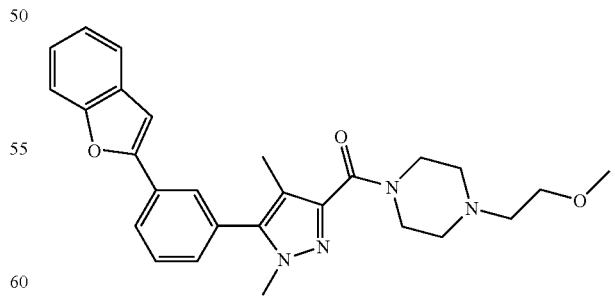

In analogy to the procedure described in Example 18], 5-(3-benzofuran-2-yl-phenyl)-1,4-dimethyl-1H-pyrazole-3-carboxylic acid (Example 16C]) and 1-(2-methoxy-ethyl)-piperazine gave the title compound in quant. yield as light brown foam. MS: 459.3 (MH⁺).

Example 21

[5-(3-Benzofuran-2-yl-phenyl)-1,4-dimethyl-1H-pyrazol-3-yl]-(3-diethylamino-pyrrolidin-1-yl)-methanone

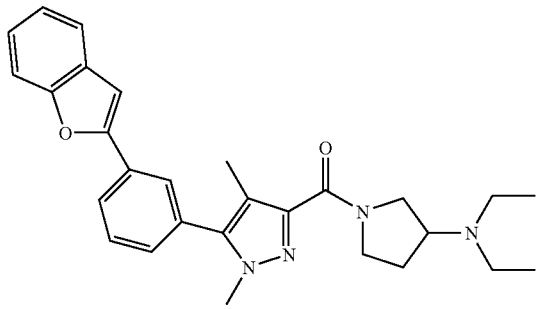

A] 5-(3-bromo-phenyl)-1,4-dimethyl-1H-pyrazole-3-carboxylic acid (7D)

In analogy to the procedure described in Example 12C], 5-(3-bromo-phenyl)-1,4-dimethyl-1H-pyrazole-3-carboxylic acid ethyl ester (Example 16A]) gave 5-(3-bromo-phenyl)-1,4-dimethyl-1H-pyrazole-3-carboxylic acid in 91% yield as light yellow foam. MS: 295.1 (MH$^+$, 1 Br).

B] [5-(3-bromo-phenyl)-1,4-dimethyl-1H-pyrazol-3-yl]-(3-diethylamino-pyrrolidin-1-yl)-methanone In analogy to the procedure described in example 12D], 5-(3-bromo-phenyl)-1,4-dimethyl-1H-pyrazole-3-carboxylic acid and 3-(diethylamino)pyrrolidine gave the title compound in 94% yield as white needles. MS: 419.2 (MH$^+$, 1 Br).

C] [5-(3-Benzofuran-2-yl-phenyl)-1,4-dimethyl-1H-pyrazol-3-yl]-1-(3-diethylamino-pyrrolidin-1-yl)-methanone In analogy to the procedure described in Example 14C], [5-(3-bromo-phenyl)-1,4-dimethyl-1H-pyrazol-3-yl]-(3-diethylamino-pyrrolidin-1-yl)-methanone and benzo[b]furan-2-boronic acid gave the title compound in 39% yield as light brown foam. MS: 457.3 (MH$^+$).

Example 22

(5-biphenyl-3-yl-1,4-dimethyl-1H-pyrazol-3-yl)-(3-diethylamino-pyrrolidin-1-yl)-methanone

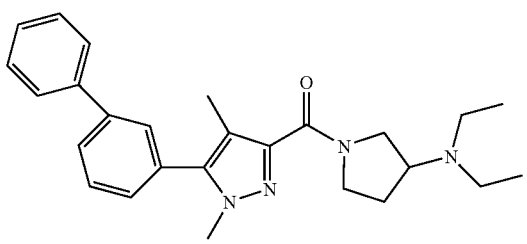

In analogy to the procedure described in example 14C] but with 2.8 eq of K$_3$PO$_4$, [5-(3-bromo-phenyl)-1,4-dimethyl-1H-pyrazol-3-yl]-(3-diethylamino-pyrrolidin-1-yl)-methanone and phenylboronic acid gave (5-biphenyl-3-yl-1,4-dimethyl-1H-pyrazol-3-yl)-(3-diethylamino-pyrrolidin-1-yl)-methanone in 59% yield as yellow oil. MS: 417.1 (MH$^+$).

Example 23

[5-(4'-chloro-biphenyl-3-yl)-1,4-dimethyl-1H-pyrazol-3-yl]-(3-diethylamino-pyrrolidin-1-yl)-methanone

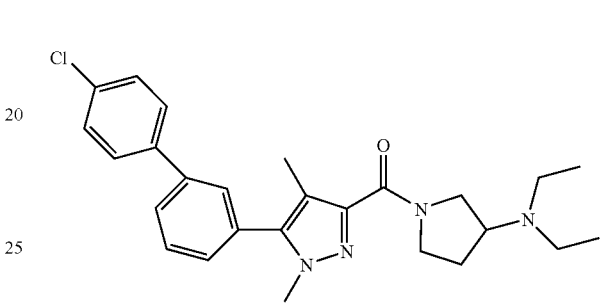

In analogy to the procedure described in example 14C] but with 2.8 eq of K$_3$PO$_4$, [5-(3-bromo-phenyl)-1,4-dimethyl-1H-pyrazol-3-yl]-(3-diethylamino-pyrrolidin-1-yl)-methanone and 4-chlorophenylboronic acid gave [5-(4'-chloro-biphenyl-3-yl)-1,4-dimethyl-1H-pyrazol-3-yl]-(3-diethylamino-pyrrolidin-1-yl)-methanone in 39% yield as light brown foam. MS: 451.3 (MH$^+$, 1 Cl).

Example 24

[5-(3'-Chloro-biphenyl-3-yl)-1,4-dimethyl-1H-pyrazol-3-yl]-(3-diethylamino-pyrrolidin-1-yl)-methanone

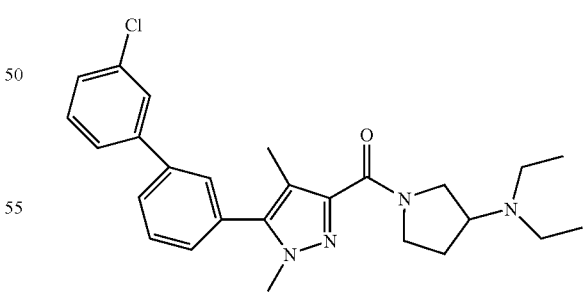

In analogy to the procedure described in example 14C] but with 2.8 eq of K$_3$PO$_4$, [5-(3-bromo-phenyl)-1,4-dimethyl-1H-pyrazol-3-yl]-(3-diethylamino-pyrrolidin-1-yl)-methanone and 3-chlorophenylboronic acid gave [5-(3'-chloro-biphenyl-3-yl)-1,4-dimethyl-1H-pyrazol-3-yl]-(3-diethylamino-pyrrolidin-1-yl)-methanone in 56% yield as light brown oil. MS: 451.0 (MH$^+$, 1 Cl).

Example 25

[5-(3',4'-Dichloro-biphenyl-3-yl)-1,4-dimethyl-1H-pyrazol-3-yl)-(3-diethylamino-pyrrolidin-1-yl)-methanone

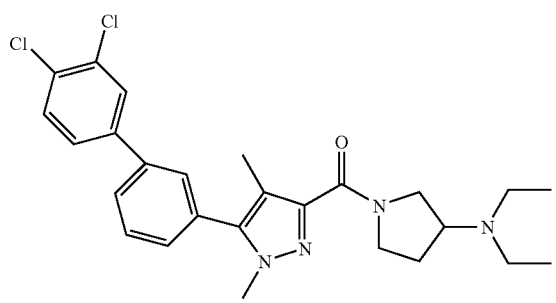

In analogy to the procedure described in example 14C], [5-(3-bromo-phenyl)-1,4-dimethyl-1H-pyrazol-3-yl]-(3-diethylamino-pyrrolidin-1-yl)-methanone and 3,4-dichlorophenylboronic acid gave [5-(3',4'-dichloro-biphenyl-3-yl)-1,4-dimethyl-1H-pyrazol-3-yl]-(3-diethylamino-pyrrolidin-1-yl)-methanone in 55% yield as light brown foam. MS: 485.2 (MH$^+$, 2 Cl).

Example 26

(5-{3-[2-(4-Chloro-phenyl)-vinyl]-phenyl}-1,4-dimethyl-1H-pyrazol-3-yl)-(3-diethylamino-pyrrolidin-1-yl)-methanone

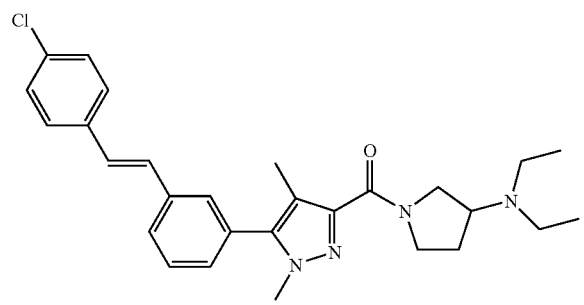

In analogy to the procedure described in example 14C] but with 2.8 eq of K$_3$PO$_4$, [5-(3-bromo-phenyl)-1,4-dimethyl-1H-pyrazol-3-yl]-(3-diethylamino-pyrrolidin-1-yl)-methanone and trans-2-(4-chlorophenyl)vinylboronic acid gave (5-{3-[2-(4-chloro-phenyl)-vinyl]-phenyl}-1,4-dimethyl-1H-pyrazol-3-yl)-(3-diethylamino-pyrrolidin-1-yl)-methanone in 67% yield as light brown oil. MS: 477.0 (MH$^+$, 1 Cl).

Example 27

[5-(3-Benzofuran-2-yl-phenyl)-2,4-dimethyl-2H-pyrazol-3-yl]-(3-diethylamino-pyrrolidin-1-yl)-methanone

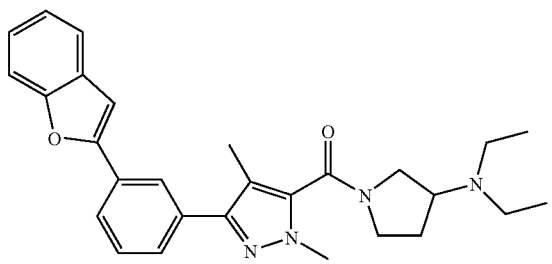

A] 5-(3-Bromo-phenyl)-2,4-dimethyl-2H-pyrazole-3-carboxylic acid

In analogy to the procedure described in Example 12C], 5-(3-bromo-phenyl)-2,4-dimethyl-2H-pyrazole-3-carboxylic acid ethyl ester (Example 16A]) gave the title compound in 97% yield as off-white powder. MS: 293.0 (M−H$^-$, 1 Br).

B] [5-(3-Bromo-phenyl)-2,4-dimethyl-2H-pyrazol-3-yl]-(3-diethylamino-pyrrolidin-1-yl)-methanone In analogy to the procedure described in example 12D), 5-(3-bromo-phenyl)-2,4-dimethyl-2H-pyrazole-3-carboxylic acid and 3-(diethylamino)pyrrolidine gave the title compound in 77% yield as light yellow viscous oil. MS: 419.0 (MH$^+$, 1 Br).

C] [5-(3-Benzofuran-2-yl-phenyl)-2,4-dimethyl-2H-pyrazol-3-yl]-(3-diethylamino-pyrrolidin-1-yl)-methanone In analogy to the procedure described in Example 14C], [5-(3-bromo-phenyl)-2,4-dimethyl-2H-pyrazol-3-yl]-(3-diethylamino-pyrrolidin-1-yl)-methanone and benzo[b]furan-2-boronic acid gave the title compound in 36% yield as yellow foam. MS: 457.4 (MH$^+$).

Example 28

[1-(3-Benzofuran-2-yl-phenyl)-3,5-dimethyl-1H-pyrazol-4-yl]-(3-diethylamino-pyrrolidin-1-yl)-methanone

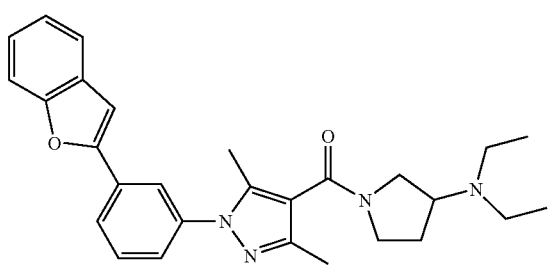

A] [1-(3-Bromo-phenyl)-3,5-dimethyl-1H-pyrazol-4-yl]-(3-diethylamino-pyrrolidin-1-yl)-methanone In analogy to the procedure described in example 12D], 1-(3-bromo-phenyl)-3,5-dimethyl-1H-pyrazole-4-carboxylic acid and 3-(diethylamino)pyrrolidine gave the title compound in 61% yield as brown viscous oil. MS: 419.2 (MH$^+$, 1 Br).

B] [1-(3-Benzofuran-2-yl-phenyl)-3,5-dimethyl-1H-pyrazol-4-yl]-(3-diethylamino-pyrrolidin-1-yl)-methanone In analogy to the procedure described in Example 14C], [1-(3-bromo-phenyl)-3,5-dimethyl-1H-pyrazol-4-yl]-(3-diethylamino-pyrrolidin-1-yl)-methanone and benzo[b]furan-2-boronic acid gave the title compound in 68% yield as light brown foam. MS: 457.3 (MH$^+$).

Example 29

(1-{3-[(E)-2-(4-Chloro-phenyl)-vinyl]-phenyl}-3,5-dimethyl-1H-pyrazol-4-yl)-(3-diethylamino-pyrrolidin-1-yl)-methanone

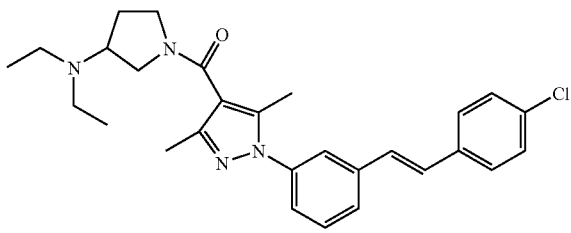

In analogy to the procedure described in Example 14C], [1-(3-bromo-phenyl)-3,5-dimethyl-1H-pyrazol-4-yl]-(3-diethylamino-pyrrolidin-1-yl)-methanone (Example 28A]) and trans-2-(4-chlorophenyl)vinylboronic acid gave the title compound in 67% yield as light brown foam. MS: 477.3 (MH$^+$, 1 Cl).

Example 30

{1-[3-((E)-2-Cyclohexyl-vinyl)-phenyl]-3,5-dimethyl-1H-pyrazol-4-yl}-(3-diethylamino-pyrrolidin-1-yl)-methanone

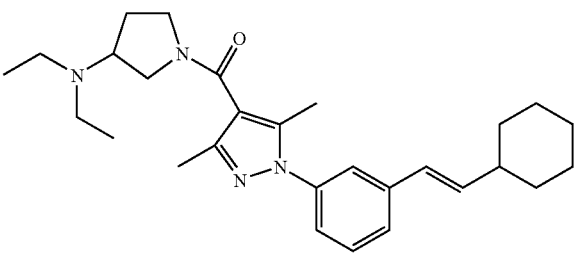

In analogy to the procedure described in Example 14C], [1-(3-bromo-phenyl)-3,5-dimethyl-1H-pyrazol-4-yl]-(3-diethylamino-pyrrolidin-1-yl)-methanone (Example 30A]) and trans-2-cyclohexylvinylboronic acid gave the title compound in 40% yield as brown gum. MS: 449.3 (MH$^+$).

Example 31

{5-[3-(3-Chloro-phenylethynyl)-phenyl]-4-methyl-1H-pyrazol-3-yl}-(3-diethylamino-pyrrolidin-1-yl)-methanone

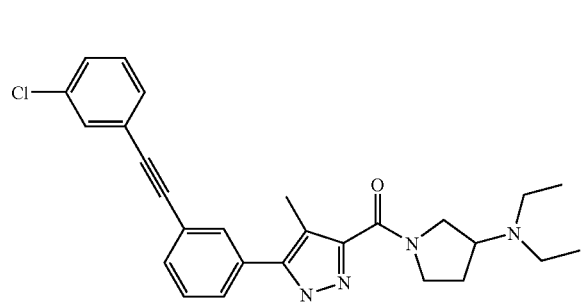

A] 5-(3-Bromo-phenyl)-4-methyl-1H-pyrazole-3-carboxylic acid ethyl ester

In analogy to the procedure described in example 16A], 4-(3-bromo-phenyl)-3-methyl-2,4-dioxo-butyric acid ethyl ester (synthesized from 3'-bromopropiophenone and diethyl oxalate, following a procedure described in Ksander, Gary M.; McMurry, John E.; Johnson, Mark. A method for the synthesis of unsaturated carbonyl compounds. Journal of Organic Chemistry (1977), 42(7), 1180-5) and hydrazine monohydrate were heated at 90° C. in EtOH for 1 h to give after crystallization (Et$_2$O/n-penatane) the title compound in 46% yield as off-white powder. MS: 308.1 (M$^+$, 1 Br).

B] 5-(3-Bromo-phenyl)-4-methyl-1H-pyrazole-3-carboxylic acid

In analogy to the procedure described in Example 12C], 5-(3-bromo-phenyl)-4-methyl-1H-pyrazole-3-carboxylic acid ethyl ester gave the title compound in 99% yield as off-white powder. MS: 279.0 (M–H$^-$, 1 Br).

C] [5-(3-Bromo-phenyl)-4-methyl-1H-pyrazol-3-yl]-(3-diethylamino-pyrrolidin-1-yl)-methanone In analogy to the procedure described in example 12D], 5-(3-bromo-phenyl)-4-methyl-1H-pyrazole-3-carboxylic acid and 3-(diethylamino)pyrrolidine gave the title compound in 91% yield as off-white foam. MS: 405.2 (MH$^+$, 1 Br).

D] (3-Diethylamino-pyrrolidin-1-yl)-[4-methyl-5-(3-trimethylsilanylethynyl-phenyl)-1H-pyrazol-3-yl]-methanone The synthesis was performed following a procedure of Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649-672. A solution of 0.405 g (1.00 mmol) of [5-(3-bromo-phenyl)-4-methyl-1H-pyrazol-3-yl]-(3-diethylamino-pyrrolidin-1-yl)-methanone in 5 ml piperidine was degassed (argon) and treated with 58 mg (0.05 mmol) Pd(PPh$_3$)$_4$ and 10 mg (0.05 mmol) CuI. The reaction mixture was stirred at 50° C. for 10 min and then slowly (60 min) treated with 0.17 ml (1.20 mmol) of ethynyltrimethylsilane in 5 ml piperidine. After 30 min the bath was slowly (30 min) heated to 80° C. The reaction mixture was stirred at this temperature for 2.5 h and then partitioned between chilled water sat. KHCO$_3$/EtOAc (3×). The organic phases were washed with aqueous 10% NaCl, dried (Na$_2$SO$_4$) and evaporated. Purification by flash-chromatography on silica gel (CH$_2$Cl$_2$/MeOH 98:2 to 92:8) yielded 0.27 g (64%) of the title compound as yellow viscous oil. MS: 423.3 (MH$^+$).

E] (3-Diethylamino-pyrrolidin-1-yl)-[5-(3-ethynyl-phenyl)-4-methyl-1H-pyrazol-3-yl]-methanone A solution of 0.101 g (0.24 mmol) of (3-diethylamino-pyrrolidin-1-yl)-[4-methyl-5-(3-trimethylsilanylethynyl-phenyl)-1H-pyrazol-3-yl]-methanone in 2.4 ml THF at 0° C. was treated with 0.26 ml (0.26 mmol) of 1M tetrabutylammonium fluoride in THF. The reaction was stirred at this temperature for 1.5 h and then partitioned between water/Et$_2$O (3×). The organic phases were washed with water, dried (Na$_2$SO$_4$) and evaporated to give 0.084 g (quant) of the title compound as yellow foam. MS: 351.3 (MH$^+$).

F] {5-[3-(3-Chloro-phenylethynyl)-phenyl]-4-methyl-1H-pyrazol-3-yl}-(3-diethylamino-pyrrolidin-1-yl)-methanone A solution of 0.086 g (0.36 mmol) of 1-chloro-3-iodobenzene in 1.5 ml piperidine was degassed (argon) and treated with 17 mg (0.01 mmol) Pd(PPh$_3$)$_4$ and 3 mg (0.01 mmol) CuI. The reaction mixture was stirred at 50° C. for 10 min and then slowly (60 min) treated with 0.105 g (0.30 mmol) of (3-diethylamino-pyrrolidin-1-yl)-[5-(3-ethynyl-phenyl)-4-methyl-1H-pyrazol-3-yl]-methanone in 1.55 ml piperidine. After 30 min the bath was slowly (30 min) heated to 80° C. The reaction mixture was stirred at this temperature for 1 h and then partitioned between chilled water sat. KHCO$_3$/Et$_2$O (3×). The organic phases were washed with aqueous 10% NaCl, dried (Na$_2$SO$_4$) and evaporated. Purification by flash-chromatography on silica gel (CH$_2$Cl$_2$/MeOH 97.5:2.5 to 95:5) yielded 0.090 g (65%) of the title compound as light yellow foam. MS: 461.1 (MH$^+$, 1 Cl).

Example 32

(3-Diethylamino-pyrrolidin-1-yl)-[4-methyl-5-(3-phenylethynyl-phenyl)-1H-pyrazol-3-yl]-methanone

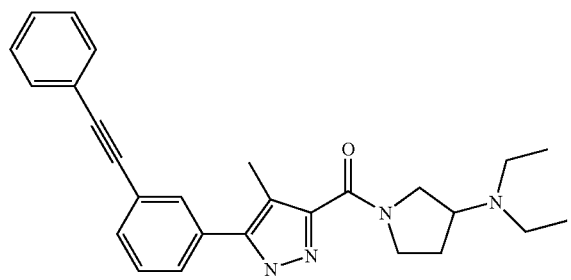

In analogy to the procedure described in Example 31F], iodobenzene and (3-diethylamino-pyrrolidin-1-yl)-[5-(3-ethynyl-phenyl)-4-methyl-1H-pyrazol-3-yl]-methanone (Example 31E]) gave the title compound in 70% yield light yellow semisolid. MS: 427.3 (MH$^+$).

Example 33

{5-[3-(3,4-Dichloro-phenylethynyl)-phenyl]-4-methyl-1H-pyrazol-3-yl}-(3-diethylamino-pyrrolidin-1-yl)-methanone

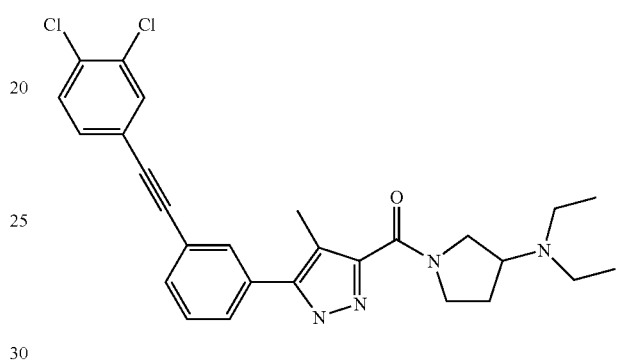

In analogy to the procedure described in Example 31F], 1,2-dichloro-4-iodobenzene and (3-diethylamino-pyrrolidin-1-yl)-[5-(3-ethynyl-phenyl)-4-methyl-1H-pyrazol-3-yl]-methanone (Example 31E]) gave the title compound in 71% yield yellow foam. MS: 495.2 (MH$^+$, 2 Cl).

Example 34

{5-[3-(4-Chloro-phenylethynyl)-phenyl]-4-methyl-1H-pyrazol-3-yl}-(3-diethylamino-pyrrolidin-1-yl)-methanone

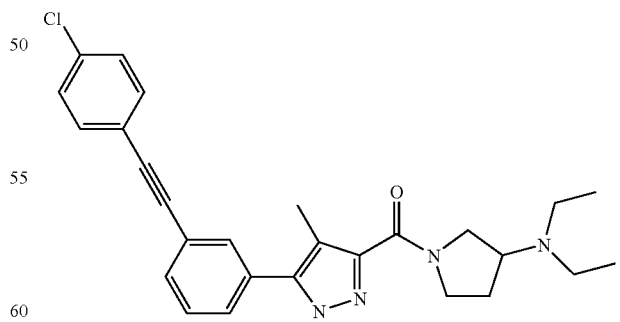

In analogy to the procedure described in Example 31F], 1-chloro-4-iodobenzene and (3-diethylamino-pyrrolidin-1-yl)-[5-(3-ethynyl-phenyl)-4-methyl-1H-pyrazol-3-yl]-methanone (Example 31E]) gave the title compound in 74% yield light yellow powder. MS: 461.1 (MH$^+$, 1 Cl).

Example 35

{5-[3-(3-Chloro-4-fluoro-phenylethynyl)-phenyl]-4-methyl-1H-pyrazol-3-yl}-(3-diethylamino-pyrrolidin-1-yl)-methanone

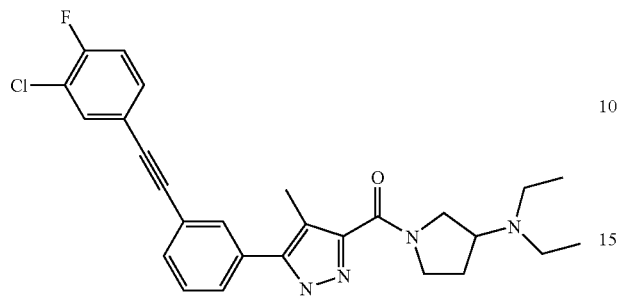

In analogy to the procedure described in Example 31F], 2-chloro-1-fluoro-4-iodobenzene and (3-diethylamino-pyrrolidin-1-yl)-[5-(3-ethynyl-phenyl)-4-methyl-1H-pyrazol-3-yl]-methanone (Example 31E]) gave the title compound in 68% yield light yellow foam. MS: 479.2 (MH+, 1 Cl).

Example 36

(3-Diethylamino-pyrrolidin-1-yl)-{3,5-dimethyl-1-[3-(3-methyl-but-1-ynyl)-phenyl]-1H-pyrazol-4-yl}-methanone

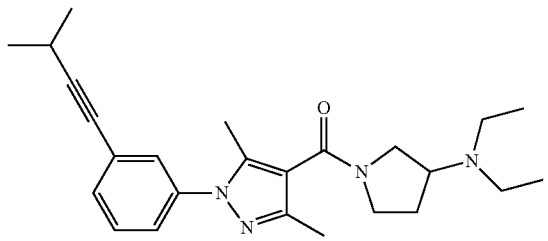

In analogy to the procedure described in Example 31F], [1-(3-bromo-phenyl)-3,5-dimethyl-1H-pyrazol-4-yl]-(3-diethylamino-pyrrolidin-1-yl)-methanone (1 eq) (Example 28A]) and 3-methyl-1-butyne (1.2 eq) gave the title compound in 90% yield yellow viscous oil. MS: 407.4 (MH+).

Example 37

(3-Diethylamino-pyrrolidin-1-yl)-{3,5-dimethyl-1-[3-(3-methyl-butyl)-phenyl]-1H-pyrazol-4-yl}-methanone

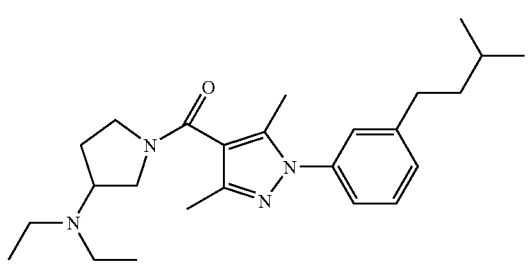

A suspension of 0.041 g (0.10 mmol) of (3-diethylamino-pyrrolidin-1-yl)-{3,5-dimethyl-1-[3-(3-methyl-but-1-ynyl)-phenyl]-1H-pyrazol-4-yl}-methanone (Example 36]) and 6 mg of platinum(IV) oxide hydrate in 0.2 ml of EtOH was stirred under hydrogen atmosphere 17 h at RT and 1 atm. The suspension was filtered and evaporated to give 0.038 g (93%) of the titled compound as colorless viscous oil. MS: 411.2 (MH+).

Example 38

3,4-Dichloro-N-{3-[3,5-dimethyl-4-(4-pyrrolidin-1-yl-piperidine-1-carbonyl)-pyrazol-1-yl]-phenyl}-benzamide

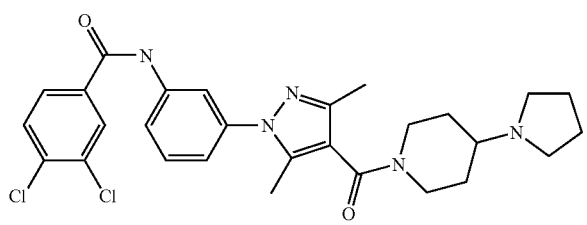

A] 3,5-Dimethyl-1-(3-nitro-phenyl)-1H-pyrazole-4-carboxylic acid ethyl ester Following the procedure described in Helvetica Chimica Acta (1952), 35, 478-85, 5.00 g (26.37 mmmol) of 3-nitrophenylhydrazine hydrochloride suspended in 46 ml of 55% aqueous AcOH were dissolved by careful heating and treated (without further heating) with 4.13 ml (26.37 mmol) of ethyl diacetoacetate. The reaction was immediately cooled and kept 20 h at 0° C. The precipitate was diluted with 28 ml of water and after 6 h filtered and washed with 2×5 ml of water to give after drying under reduced pressure 4.66 g (61%) of the title compound as a light yellow solid. MS: 289.9 (MH+).

B] 3,5-Dimethyl-1-(3-nitro-phenyl)-1H-pyrazole-4-carboxylic acid

In analogy to the procedure described in Example 12C], 3,5-dimethyl-1-(3-nitro-phenyl)-1H-pyrazole-4-carboxylic acid ethyl ester gave after acidification and filtration from the water phase the title compound in 65% yield as light brown solid. MS: 260.0 (M−H−).

C] [3,5-Dimethyl-1-(3-nitro-phenyl)-1H-pyrazol-4-yl]-(4-pyrrolidin-1-yl-piperidin-1-yl)-methanone In analogy to the procedure described in Example 18], 3,5-dimethyl-1-(3-nitro-phenyl)-1H-pyrazole-4-carboxylic acid and 4-pyrrolidine-1-yl-piperidine gave the tide compound in 93% yield as green foam. MS: 398.1 (MH+).

D] [1-(3-Amino-phenyl)-3,5-dimethyl-1H-pyrazol-4-yl]-(4-pyrrolidin-1-yl-piperidin-1-yl)-methanone hydrochloride A suspension of 1.10 g (2.77 mmol) of [3,5-dimethyl-1-(3-nitro-phenyl)-1H-pyrazol-4-yl]-(4-pyrrolidin-1-yl-piperidin-1-yl)-methanone and 0.11 g of 10% Pd/C in 24 ml of EtOH was stirred under hydrogen atmosphere 2 h at RT and 1 atm. The suspension was filtered and evaporated to give 1.07 g (95%) of the titled compound as light yellow solid. MS: 368.1 (MH+).

E] 3,4-Dichloro-N-{3-[3,5-dimethyl-4-(4-pyrrolidin-1-yl-piperidine-1-carbonyl)-pyrazol-1-yl]-phenyl}-benzamide A solution of 0.080 g (0.20 mmol) of [1-(3-amino-phenyl)-3,5-dimethyl-1H-pyrazol-4-yl]-(4-pyrrolidin-1-yl-piperidin-1-yl)-methanone hydrochloride and 0.11 ml (0.79 mmol, 4 eq) of triethylamine in 3 ml of $CH_2Cl_2$ was treated at 0° C. with 0.050 g (0.24 mmol, 1.2 eq) of 3,4-dichlorobenzoyl chloride. The reaction was stirred over night at RT, then partitioned three times between EtOAc and aqueous saturated $NaHCO_3$, dried over $Na_2SO_4$ and evaporated to give 0.115 g (quant.) of the title compound as light yellow solid. MS: 540.4 (MH$^+$, 2 Cl).

Example 39

3-Chloro-N-{3-[3,5-dimethyl-4-(4-pyrrolidin-1-yl-piperidine-1-carbonyl)-pyrazol-1-yl]-phenyl}-benzamide

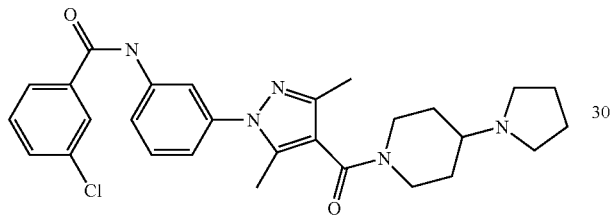

In analogy to the procedure described in Example 38E], [1-(3-amino-phenyl)-3,5-dimethyl-1H-pyrazol-4-yl]-(4-pyrrolidin-1-yl-piperidin-1-yl)-methanone hydrochloride (Example 38D]) and 3-chlorobenzoyl chloride gave the title compound in 91% yield as light yellow solid. MS: 506.2 (MH$^+$, 1 Cl).

Example 40

4-Chloro-N-{3-[3,5-dimethyl-4-(4-pyrrolidin-1-yl-piperidine-1-carbonyl)-pyrazol-1-yl]-phenyl}-benzamide

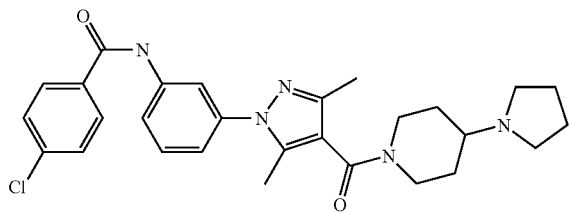

In analogy to the procedure described in Example 38E], [1-(3-amino-phenyl)-3,5-dimethyl-1H-pyrazol-4-yl]-(4-pyrrolidin-1-yl-piperidin-1-yl)-methanone hydrochloride (Example 38D]) and 4-chlorobenzoyl chloride gave the title compound in 62% yield as yellow oil. MS: 506.3 (MH$^+$, 1 Cl).

Example 41

N-{3-[3,5-Dimethyl-4-(4-pyrrolidin-1-yl-piperidine-1-carbonyl)-pyrazol-1-yl]-phenyl}-2,2,2-trifluoro-acetamide

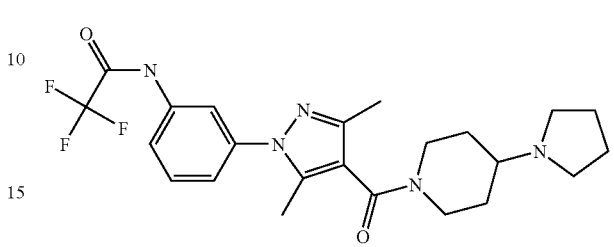

In analogy to the procedure described in Example 38E], [1-(3-amino-phenyl)-3,5-dimethyl-1H-pyrazol-4-yl]-(4-pyrrolidin-1-yl-piperidin-1-yl)-methanone hydrochloride (Example 38D]) and trifluoroacetic acid anhydride gave the title compound in quant yield as light yellow solid. MS: 464.3 (MH$^+$).

Example 42

[1-(3-Methoxy-5-trifluoromethyl-phenyl)-3,5-dimethyl-1H-pyrazol-4-yl]-(4-pyrrolidin-1-yl-piperidin-1-yl)-methanone

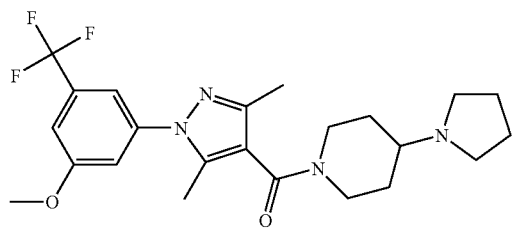

A] (3-Methoxy-5-trifluoromethyl-phenyl)-hydrazine

Following the procedure described in Journal of Organic Chemistry (1972), 37(18), 2849-53, 0.5 g (2.62 mmol) of 3-methoxy-5-trifluoromethyl-phenylamine was suspended in 4.6 ml of 25% aqueous HCl, cooled (0° C.) and carefully treated (without exceeding 10° C.) with 0.189 g (2.75 mmol) of sodium nitrite dissolved in 2.7 ml of water. The solution was stirred for 1 h at this temperature and 30 min at RT. Then, 2.48 g (13.08 mmol) of tin(II) chloride in 2.5 ml of 25% aqueous HCl were dropped carefully to the cooled (0° C.) solution and stirred for 1 h. The reaction was neutralized and basified with 32% aqueous NaOH (pH14), partitioned three times between $CH_2Cl_2$ and water. The organic phase was dried over $Na_2SO_4$ and evaporated to give 0.50 g (93%) of the title compound as a yellow solid. MS: 206.8 (MH$^+$).

B] 1-(3-Methoxy-5-trifluoromethyl-phenyl)-3,5-dimethyl-1H-pyrazole-4-carboxylic acid ethyl ester In analogy to the procedure described in Example 38A], (3-methoxy-5-trifluoroxyethyl-phenyl)-hydrazine and ethyl diacetoacetate gave, after extraction with Et₂O, the title compound in 58% yield as a light yellow oil. MS: 342.9 (MH⁺).

C] 1-(3-Methoxy-5-trifluoromethyl-phenyl)-3,5-dimethyl-1H-pyrazole-4-carboxylic acid In analogy to the procedure described in Example 12C], 1-(3-methoxy-5-trifluoromethyl-phenyl)-3,5-dimethyl-1H-pyrazole-4-carboxylic acid ethyl ester gave the title compound in quant yield as off-white solid. MS: 312.9 (M–H⁻).

D] [1-(3-Methoxy-5-trifluoromethyl-phenyl)-3,5-dimethyl-1H-pyrazol-4-yl]-(4-pyrrolidin-1-yl-piperidin-1-yl)-methanone In analogy to the procedure described in Example 18], 1-(3-methoxy-5-trifluoromethyl-phenyl)-3,5-dimethyl-1H-pyrazole-4-carboxylic acid and 4-pyrrolidine-1-yl-piperidine gave, after purification on a flash isolute NH2-column (EtOAc), the title compound in 63% yield as light brown foam. MS: 451.3 (MH⁺).

Example 43

[1-(2-Methoxy-5-trifluoromethyl-phenyl)-3,5-dimethyl-1H-pyrazol-4-yl]-(4-pyrrolidin-1-yl-piperidin-1-yl)-methanone

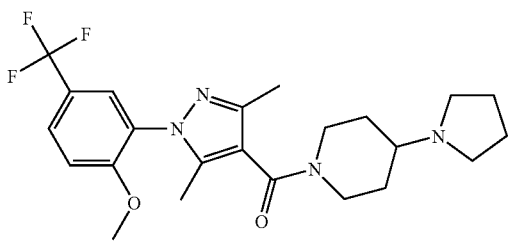

A] (2-Methoxy-5-trifluoromethyl-phenyl)-hydrazine

In analogy to the procedure described in Example 42A], 2-methoxy-5-trifluoromethyl-phenylamine gave the title compound in 80% yield as light brown solid. MS: 206.9 (MH⁺).

B] 1-(2-Methoxy-5-trifluoromethyl-phenyl)-3,5-dimethyl-1H-pyrazole-4-carboxylic acid ethyl ester In analogy to the procedure described in Example 38A], (2-methoxy-5-trifluoromethyl-phenyl)-hydrazine and ethyl diacetoacetate gave, after flash column chromatography (CH₂Cl₂ to CH₂Cl₂:MeOH 99:1), the title compound in 58% yield as a light green solid. MS: 343.1 (MH⁺).

C] 1-(2-Methoxy-5-trifluoromethyl-phenyl)-3,5-dimethyl-1H-pyrazole-4-carboxylic acid In analogy to the procedure described in Example 12C], 1-(2-methoxy-5-trifluoromethyl-phenyl)-3,5-dimethyl-1H-pyrazole-4-carboxylic acid ethyl ester gave the title compound in quant yield as light yellow solid. MS: 313.0 (M–H⁻).

D] [1-(2-Methoxy-5-trifluoromethyl-phenyl)-3,5-dimethyl-1H-pyrazol-4-yl]-(4-pyrrolidin-1-yl-piperidin-1-yl)-methanone In analogy to the procedure described in Example 18], 1-(2-methoxy-5-trifluoromethyl-phenyl)-3,5-dimethyl-1H-pyrazole-4-carboxylic acid and 4-pyrrolidine-1-yl-piperidine gave, after purification on a flash isolute NH2-column (EtOAc:n-heptane 4:1), the title compound in 27% yield as yellow oil. MS: 451.2 (MH⁺).

Example 44

[1-(5-Chloro-2-methoxy-phenyl)-3,5-dimethyl-1H-pyrazol-4-yl]-(4-pyrrolidin-1-yl-piperidin-1-yl)-methanone

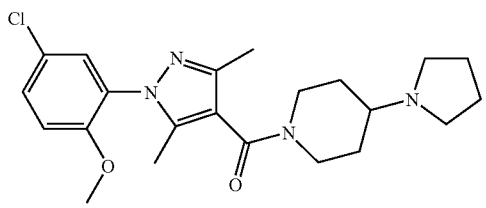

A] 1-(5-Chloro-2-methoxy-phenyl)-3,5-dimethyl-1H-pyrazole-4-carboxylic acid ethyl ester In analogy to the procedure described in Example 38A], (5-chloro-2-methoxy-phenyl)-hydrazine hydrochloride and ethyl diacetoacetate gave, after precipitation (CH₂Cl₂/n-pentane), the title compound in 38% yield as light brown solid. MS: 309.1 (MH⁺, 1 Cl).

B] 1-(5-Chloro-2-methoxy-phenyl)-3,5-dimethyl-1H-pyrazole-4-carboxylic acid

In analogy to the procedure described in Example 12C], 1-(5-chloro-2-methoxy-phenyl)-3,5-dimethyl-1H-pyrazole-4-carboxylic acid ethyl ester gave the title compound in 92% yield as light brown solid. MS: 279.1 (M–H⁻, 1 Cl).

C][1-(5-Chloro-2-methoxy-phenyl)-3,5-dimethyl-1H-pyrazol-4-yl]-(4-pyrrolidin-1-yl-piperidin-1-yl)-methanone In analogy to the procedure described in Example 18], 1-(5-chloro-2-methoxy-phenyl)-3,5-dimethyl-1H-pyrazole-4-carboxylic acid and 4-pyrrolidine-1-yl-piperidine gave the title compound in 99% yield as light yellow foam. MS: 417.0 (MH⁺, 1 Cl).

Example 45

[3,5-Dimethyl-1-(4-trifluoromethoxy-phenyl)-1H-pyrazol-4-yl]-(4-pyrrolidin-1-yl-piperidin-1-yl)-methanone

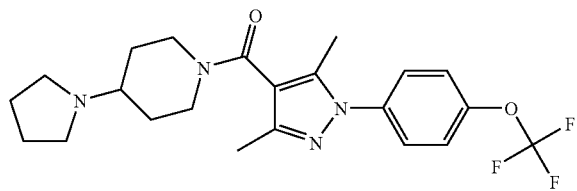

A] 3,5-Dimethyl-1-(4-trifluoromethoxy-phenyl)-1H-pyrazole-4-carboxylic acid ethyl ester In analogy to the procedure described in Example 38A], (4-trifluoromethoxy-phenyl)-hydrazine hydrochloride and ethyl diacetoacetate gave, after extraction (3× Et$_2$O), drying (Na$_2$SO$_4$) and evaporation, the title compound in 72% yield as orange oil. MS: 328.9 (MH$^+$).

B] 3,5-Dimethyl-1-(4-trifluoromethoxy-phenyl)-1H-pyrazole-4-carboxylic acid

In analogy to the procedure described in Example 12C], 3,5-dimethyl-1-(4-trifluoromethoxy-phenyl)-1H-pyrazole-4-carboxylic acid ethyl ester gave, after suspension in Et$_2$O and filtration, the title compound in 18% yield as light brown solid. MS: 299.2 (M–H$^-$).

C] [3,5-Dimethyl-1-(4-trifluoromethoxy-phenyl)-1H-pyrazol-4-yl]-(4-pyrrolidin-1-yl-piperidin-1-yl)-methanone In analogy to the procedure described in Example 18], 3,5-dimethyl-1-(4-trifluoromethoxy-phenyl)-1H-pyrazole-4-carboxylic acid and 4-pyrrolidine-1-yl-piperidine gave the title compound in 95% yield as light brown solid. MS: 437.2 (MH$^+$).

Example 46-52

General Procedure for Examples 46-52

A solution of intermediate 5 (0.05 mol), Et$_3$N (0.3 mmol), HATU (0.06 mmol) and appropriate amine (0.1 mmol) were shaken for 16 h and the products purified directly by preparative HPLC.

TABLE 1

| Example No. | Compound Name | Structure | Amine | MS: (MH$^+$) |
|---|---|---|---|---|
| 46 | [1-(4-Benzofuran-2-yl-pyrimidin-2-yl)-5-cyclopropyl-1H-pyrazol-4-yl]-(4-isopropyl-piperazin-1-yl)-methanone | 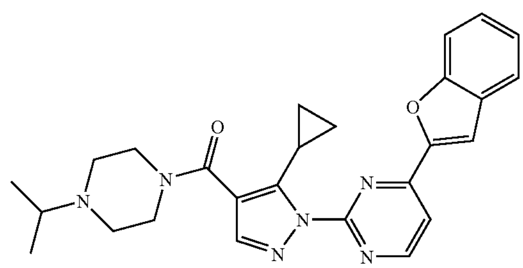 | 1-Isopropyl-piperazine | 457.2 |
| 47 | [1-(4-Benzofuran-2-yl-pyrimidin-2-yl)-5-cyclopropyl-1H-pyrazol-4-yl]-(4-cyclopentyl-piperazin-1-yl)-methanone | 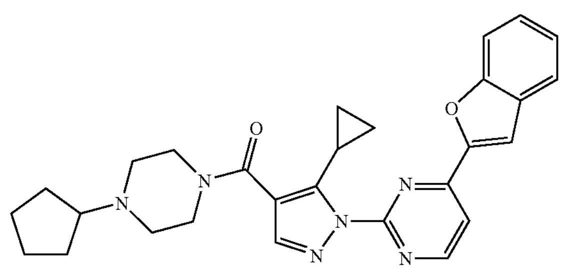 | 1-Cyclopentyl-piperazine | 483.3 |
| 48 | [1-(4-Benzofuran-2-yl-pyrimidin-2-yl)-5-cyclopropyl-1H-pyrazol-4-yl]-(4-morpholin-4-yl-piperazin-1-yl)-methanone | 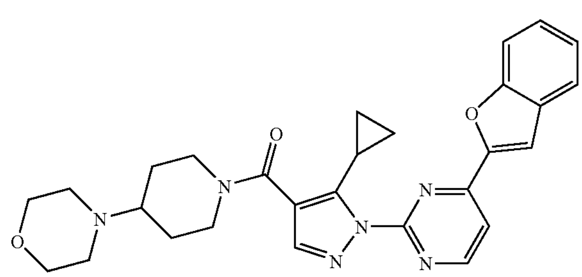 | 4-Piperidin-4-yl-morpholine | 499.3 |

TABLE 1-continued

| Example No. | Compound Name | Structure | Amine | MS: (MH+) |
|---|---|---|---|---|
| 49 | [1-(4-Benzofuran-2-yl-pyrimidin-2-yl)-5-cyclopropyl-1H-pyrazol-4-yl]-(3-diethylamino-pyrrolidin-1-yl)-methanone | 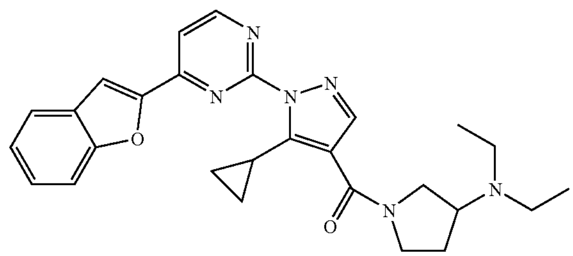 | Diethyl-pyrrolidin-3-yl-amine | 471.2 |
| 50 | [1-(4-Benzofuran-2-yl-pyrimidin-2-yl)-5-cyclopropyl-1H-pyrazol-4-yl]-[(R)-3-(tetrahydro-pyran-4-ylamino)-pyrrolidin-1-yl]-methanone | 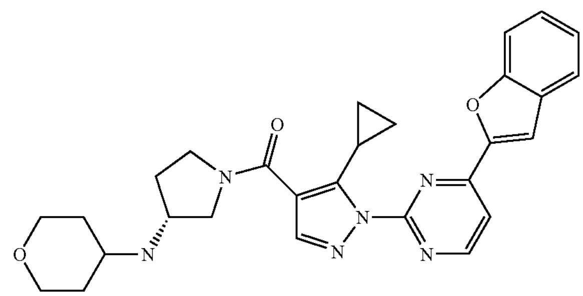 | (R)-Pyrrolidin-3-yl-(tetrahydro-pyran-4-yl)-carbamic acid tert-butyl ester-Boc removal with HCl (Intermediate 37) | 499.3 |
| 51 | [1-(4-Benzofuran-2-yl-pyrimidin-2-yl)-5-cyclopropyl-1H-pyrazol-4-yl]-{(R)-3-[methyl-(tetrahydro-pyran-4-yl)-amino]-pyrrolidin-1-yl}-methanone | 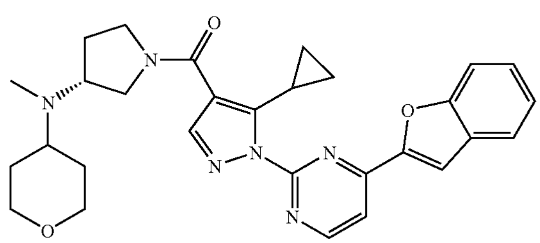 | Methyl-(R)-pyrrolidin-3-yl-(tetrahydro-pyran-4-yl)-amine (Intermediate 18) | 513.3 |
| 52 | [1-(4-Benzofuran-2-yl-pyrimidin-2-yl)-5-cyclopropyl-1H-pyrazol-4-yl]-(4-hydroxy-[1,4']bipiperidinyl-1'-yl)-methanone | 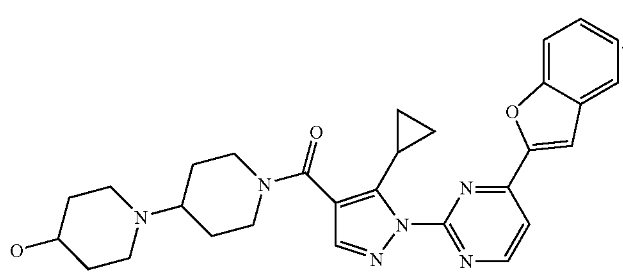 | [1,4']Bipiperidinyl-4-ol | 513.3 |

Examples 53-70

General Procedure for Examples 53-70

A solution of intermediate 4 (0.05 mol), Et$_3$N (0.3 mmol), HATU (0.06 mmol) and appropriate amine (0.1 mmol) were shaken for 16 h and the products purified directly by preparative HPLC.

TABLE 2

| Example No. | Compound Name | Structure | Amine | MS: (MH+) |
|---|---|---|---|---|
| 53 | (1-{3-[(E)-2-(4-Chloro-phenyl)-vinyl]-phenyl}-3,5-dimethyl-1H-pyrazol-4-yl)-(4-dimethylamino-piperidin-1-yl)-methanone | 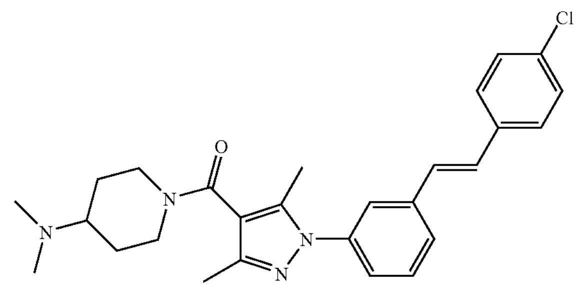 | Dimethyl-piperidin-4-yl-amine | 463.4 |
| 54 | (1-{3-[(E)-2-(4-Chloro-phenyl)-vinyl]-phenyl}-3,5-dimethyl-1H-pyrazol-4-yl)-(4-pyrrolidin-1-yl-piperidin-1-yl)-methanone | 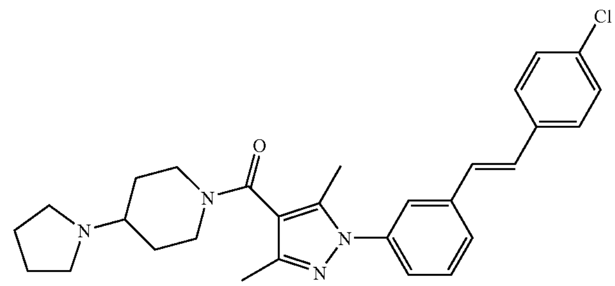 | 4-Pyrrolidin-1-yl-piperidine | 489.4 |
| 55 | (1-{3-[(E)-2-(4-Chloro-phenyl)-vinyl]-phenyl}-3,5-dimethyl-1H-pyrazol-4-yl)-(3-hydroxy-[1,4']bipiperdinyl-1'-yl)-methanone | 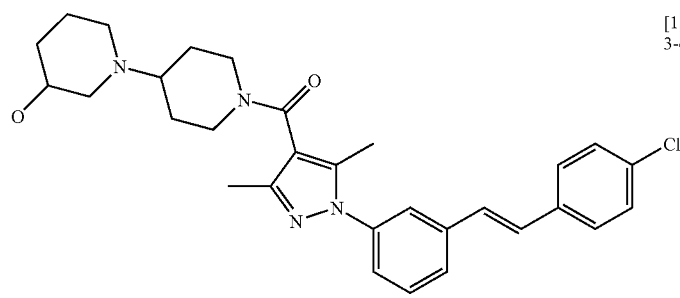 | [1,4']Bipiperidinyl-3-ol | 519.4 |
| 56 | (1-{3-[(E)-2-(4-Chloro-phenyl)-vinyl]-phenyl}-3,5-dimethyl-1H-pyrazol-4-yl)-(4-methyl-piperazin-1-yl)-methanone | 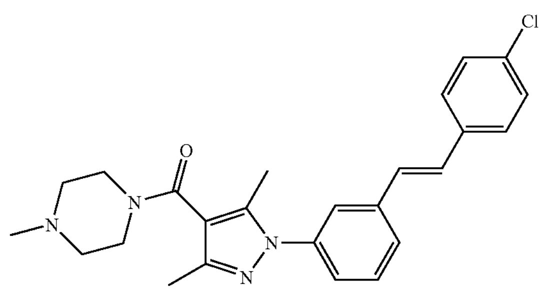 | 1-Methyl-piperazine | 435.3 |
| 57 | (1-{3-[(E)-2-(4-Chloro-phenyl)-vinyl]-phenyl}-3,5-dimethyl-1H-pyrazol-4-yl)-(4-morpholin-4-yl-piperidin-1-yl)-methanone | 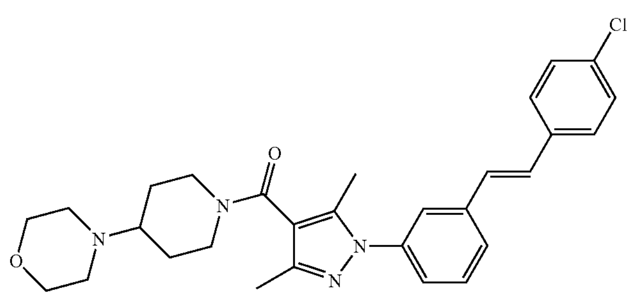 | 4-Piperidin-4-yl-morpholine | 505.4 |

TABLE 2-continued

| Example No. | Compound Name | Structure | Amine | MS: (MH+) |
|---|---|---|---|---|
| 58 | (1-{3-[(E)-2-(4-Chloro-phenyl)-vinyl]-phenyl}-3,5-dimethyl-1H-pyrazol-4-yl)-[4-(2-hydroxy-ethyl)-piperazin-1-yl]-methanone | 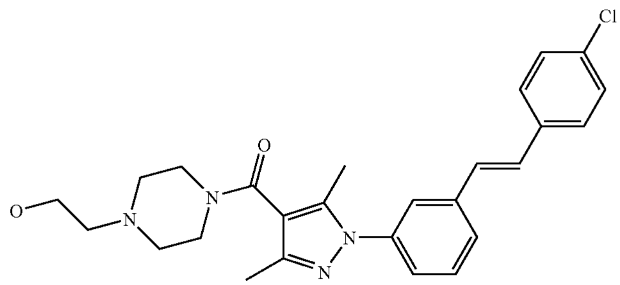 | 2-Piperazin-1-yl-ethanol | 465.3 |
| 59 | (1-{3-[(E)-2-(4-Chloro-phenyl)-vinyl]-phenyl}-3,5-dimethyl-1H-pyrazol-4-yl)-(4-isopropyl-piperazin-1-yl)-methanone | 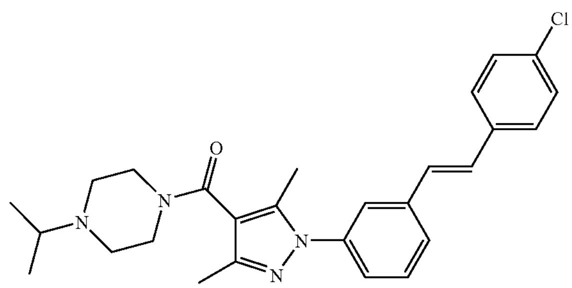 | 1-Isopropyl-piperazine | 463.4 |
| 60 | (1-{3-[(E)-2-(4-Chloro-phenyl)-vinyl]-phenyl}-3,5-dimethyl-1H-pyrazol-4-yl)-((R)-3-morpholin-4-yl-pyrrolidin-1-yl)-methanone | 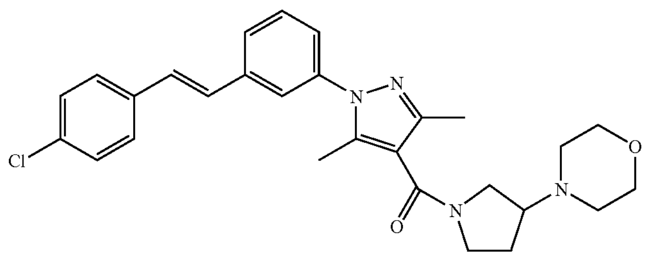 | (R)-4-Pyrrolidin-3-yl-morpholine (Intermediate 20) | 491.4 |
| 61 | (1-{3-[(E)-2-(4-Chloro-phenyl)-vinyl]-phenyl}-3,5-dimethyl-1H-pyrazol-4-yl)-{(R)-3-[methyl-(tetrahydro-pyran-4-yl)-amino]-pyrrolidin-1-yl}-methanone | 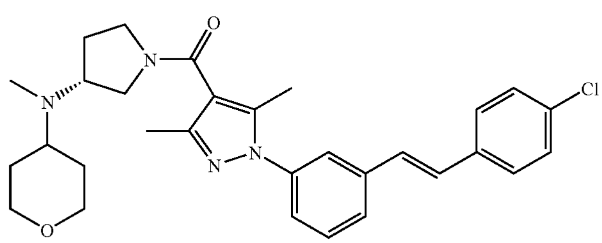 | Methyl-(R)-pyrrolidin-3-yl-(tetrahydro-pyran-4-yl)-amine (Intermediate 18) | 519.4 |
| 62 | (1-{3-[(E)-2-(4-Chloro-phenyl)-vinyl]-phenyl}-3,5-dimethyl-1H-pyrazol-4-yl)-(3-dimethylamino-pyrrolidin-1-yl)-methanone | 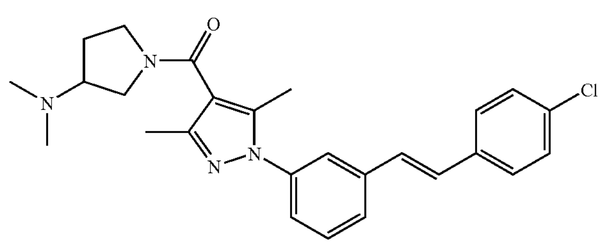 | Dimethyl-pyrrolidin-3-yl-amine | 449.4 |
| 63 | (1-{3-[(E)-2-(4-Chloro-phenyl)-vinyl]-phenyl}-3,5-dimethyl-1H-pyrazol-4-yl)-{(S)-3-[methyl-(tetrahydro-pyran-4-yl)-amino]-pyrrolidin-1-yl}-methanone | 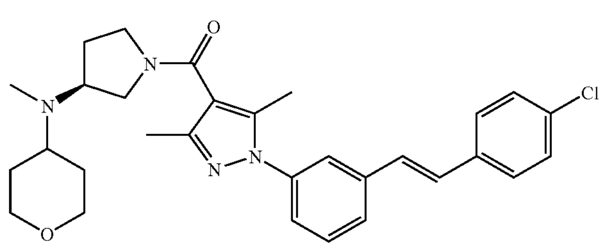 | Methyl-(S)-pyrrolidin-3-yl-(tetrahydro-pyran-4-yl)-amine (Intermediate 19) | 519.4 |

TABLE 2-continued

| Example No. | Compound Name | Structure | Amine | MS: (MH+) |
|---|---|---|---|---|
| 64 | (1-{3-[(E)-2-(4-Chloro-phenyl)-vinyl]-phenyl}-3,5-dimethyl-1H-pyrazol-4-yl)-[4-(2-hydroxy-ethyl)-[1,4]diazepan-1-yl]-methanone | 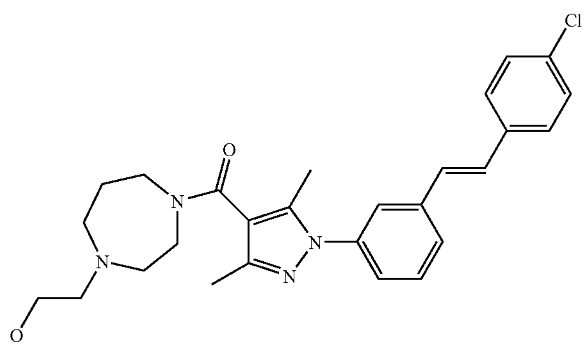 | 2-[1,4]Diazepan-1-yl-ethanol | 479.3 |
| 65 | (1-{3-[(E)-2-(4-Chloro-phenyl)-vinyl]-phenyl}-3,5-dimethyl-1H-pyrazol-4-yl)-(4-cyclopentyl-piperazin-1-yl)-methanone | 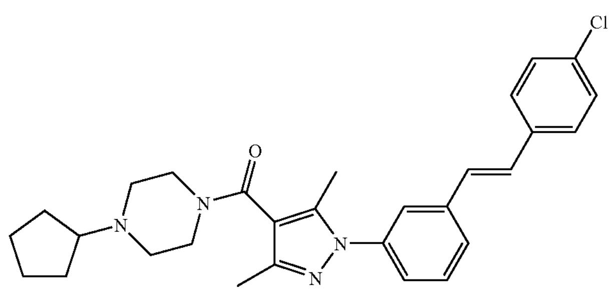 | 1-Cyclopentyl-piperazine | 489.4 |
| 66 | [1,4']Bipiperidinyl-1'-yl-(1-{3-[(E)-2-(4-chloro-phenyl)-vinyl]-phenyl}-3,5-dimethyl-1H-pyrazol-4-yl)-methanone | 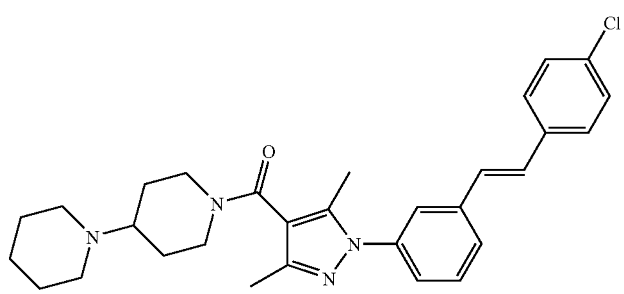 | [1,4']Bipiperidinyl | 503.4 |
| 67 | 8-(1-{3-[(E)-2-(4-Chloro-phenyl)-vinyl]-phenyl]-3,5-dimethyl-1H-pyrazole-4-carbonyl)-1,3,8-triaza-spiro[4.5]decane-2,4-dione | 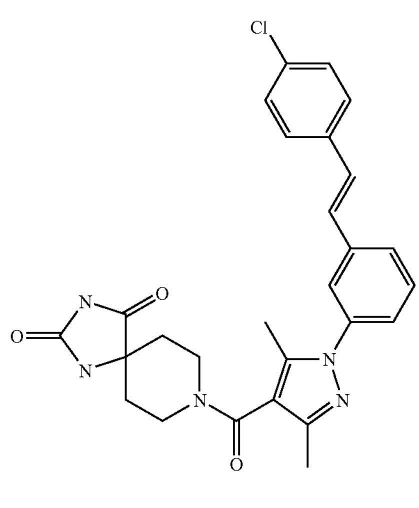 | 1,3,8-Triaza-spiro[4.5]decane-2,4-dione (Intermediate 33) | 504.3 |

TABLE 2-continued

| Example No. | Compound Name | Structure | Amine | MS: (MH+) |
|---|---|---|---|---|
| 68 | 8-(1-{3-[(E)-2-(4-Chloro-phenyl)-vinyl]-phenyl}-3,5-dimethyl-1H-pyrazole-4-carbonyl)-1-oxa-3,8-diaza-spiro[4.5]decan-2-one | 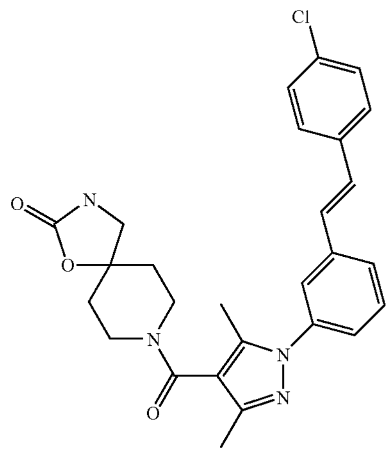 | 1-Oxa-3,8-diaza-spiro[4.5]decane-2-one (Intermediate 34) | 491.3 |
| 69 | 1-[1-(1-{3-[(E)-2-(4-Chloro-phenyl)-vinyl]-phenyl}-3,5-dimethyl-1H-pyrazole-4-carbonyl)-piperidin-4-yl]-imidazolidin-2-one | 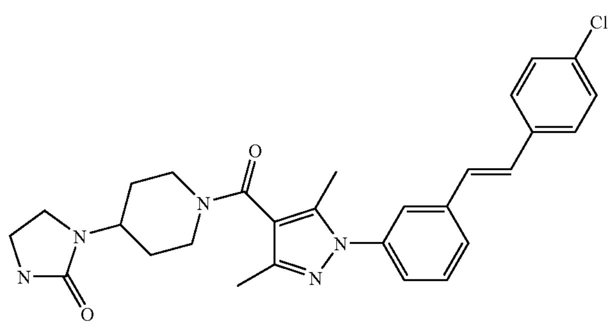 | 1-Piperidin-4-yl-imidazolidin-2-one (Intermediate 32) | 504.4 |
| 70 | 8-(1-{3-[(E)-2-(4-Chloro-phenyl)-vinyl]-phenyl}-3,5-dimethyl-1H-pyrazole-4-carbonyl)-2,8-diaza-spiro[4.5]decan-1,3-dione | 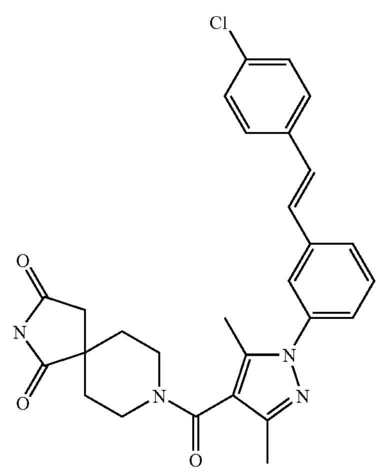 | 2,8-Diaza-spiro[4.5]decane-1,3-dione (Intermediate 35) | 503.3 |

Example 71-76

General Procedure for Examples 71-76

A solution of 4-pyrrolidin-1-yl-piperidine (0.1 mol), Et$_3$N (0.3 mmol), HATU (0.06 mmol) and appropriate acid (0.05 mmol) in DMF (0.5 ml) were shaken for 16 h and the products purified directly by preparative HPLC.

TABLE 3

| Example No. | Compound Name | Structure | Acid | MS: (MH+) |
|---|---|---|---|---|
| 71 | [3,5-Dimethyl-1-(5-trifluoromethyl-pyridin-3-yl)-1H-pyrazol-4-yl]-(4-pyrrolidin-1-yl-piperidin-1-yl)-methanone | 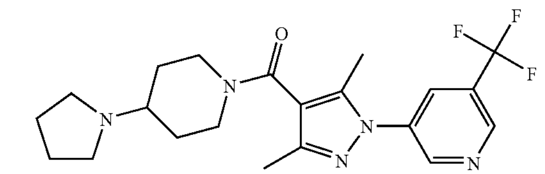 | 3,5-Dimethyl-1-(5-trifluoromethyl-pyridin-3-yl)-1H-pyrazole-4-carboxylic acid (Intermediate 6) | 422.3 |
| 72 | [3-Cyclopropyl-5-methyl-1-(3-trifluoromethoxy-phenyl)-1H-pyrazol-4-yl]-(4-pyrrolidin-1-yl-piperidin-1-yl)-methanone | 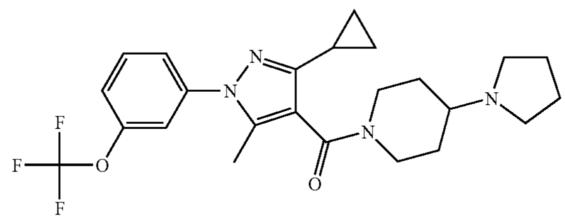 | 3-Cyclopropyl-5-methyl-1-(3-trifluoromethoxy-phenyl)-1H-pyrazole-4-carboxylic acid (Intermediate 13) | 463.2 |
| 73 | [5-Cyclopropyl-3-methyl-1-(3-trifluoromethoxy-phenyl)-1H-pyrazol-4-yl]-(4-pyrrolidin-1-yl-piperidin-1-yl)-methanone | 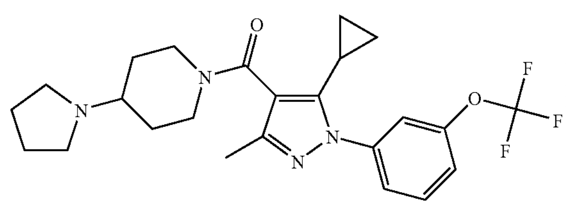 | 5-Cyclopropyl-3-methyl-1-(3-trifluoromethoxy-phenyl)-1H-pyrazole-4-carboxylic acid (Intermediate 14) | 463.2 |
| 74 | [5-Cyclopropyl-3-methyl-1-(3-trifluoromethyl-phenyl)-1H-pyrazol-4-yl]-(4-pyrrolidin-1-yl-piperidin-1-yl)-methanone | 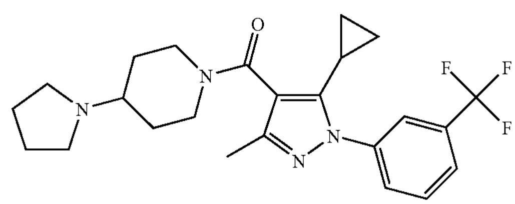 | 5-Cyclopropyl-3-methyl-1-(3-trifluoromethyl-phenyl)-1H-pyrazole-4-carboxylic acid (Intermediate 12) | 447.3 |
| 75 | [3-Cyclopropyl-5-methyl-1-(3-trifluoromethyl-phenyl)-1H-pyrazol-4-yl]-(4-pyrrolidin-1-yl-piperidin-1-yl)-methanone | 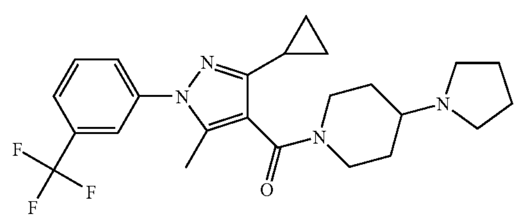 | 3-Cyclopropyl-5-methyl-1-(3-trifluoromethyl-phenyl)-1H-pyrazole-4-carboxylic acid (Intermediate 11) | 447.3 |
| 76 | [3,5-Dicyclopropyl-1-(3-trifluoromethoxy-phenyl)-1H-pyrazol-4-yl]-(4-pyrrolidin-1-yl-piperidin-1-yl)-methanone | 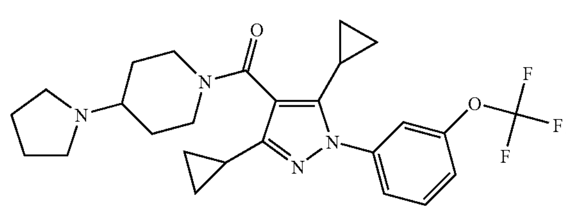 | 3,5-Dicyclopropyl-1-(3-trifluoromethoxy-phenyl)-1H-pyrazole-4-carboxylic acid (Intermediate 17) | 489.3 |

Example 77-86

General Procedure for Examples 77-86

A solution of intermediate 7 (0.05 mol), $Et_3N$ (0.3 mmol), HATU (0.06 mmol) and appropriate amine (0.1 mmol) in DMF (0.5 ml) were shaken for 16 h and the products purified directly by preparative HPLC.

TABLE 4

| Example No. | Compound Name | Structure | Amine | MS: (MH+) |
|---|---|---|---|---|
| 77 | [3,5-Dimethyl-1-(3-trifluoromethyl-phenyl)-1H-pyrazol-4-yl]-(4-isopropyl-piperazin-1-yl)-methanone | 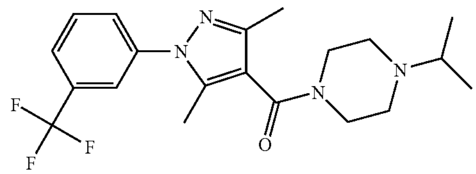 | 1-Isopropyl-piperazine | 395.3 |
| 78 | (4-Cyclopentyl-piperazin-1-yl)-[3,5-dimethyl-1-(3-trifluoromethyl-phenyl)-1H-pyrazol-4-yl]-methanone | 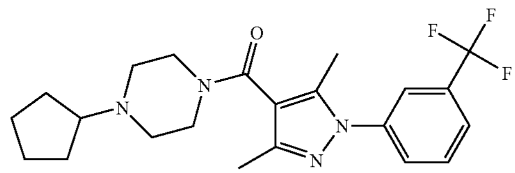 | 1-Cyclopentyl-piperazine | 421.3 |
| 79 | [3,5-Dimethyl-1-(3-trifluoromethyl-phenyl)-1H-pyrazol-4-yl]-(4-hydroxy-[1,4']bipiperidinyl-1'-yl)-methanone | 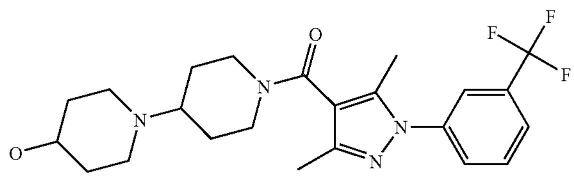 | [1,4']Bipiperidinyl-4-ol | 451.3 |
| 80 | (3-Diethylamino-pyrrolidin-1-yl)-[3,5-dimethyl-1-(3-trifluoromethyl-phenyl)-1H-pyrazol-4-yl]-methanone | 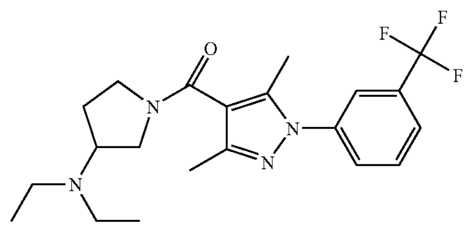 | Diethyl-pyrrolidin-3-yl-amine | 409.3 |
| 81 | (4-Dimethylamino-piperidin-1-yl)-[3,5-dimethyl-1-(3-trifluoromethyl-phenyl)-1H-pyrazol-4-yl]-methanone | 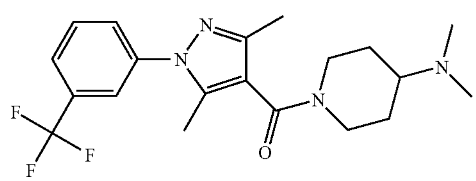 | Dimethyl-piperdin-4-yl-amine | 395.3 |
| 82 | [3,5-Dimethyl-1-(3-trifluoromethyl-phenyl)-1H-pyrazol-4-yl]-(4-pyrrolidin-1-yl-piperidin-1-yl)-methanone | 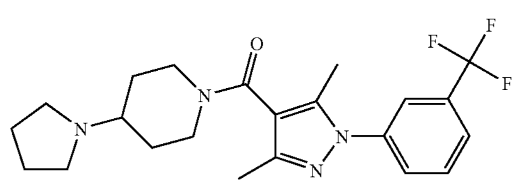 | 4-Pyrrolidin-1-yl-piperidine | 421.3 |
| 83 | [3,5-Dimethyl-1-(3-trifluoromethyl-phenyl)-1H-pyrazol-4-yl]-(4-morpholin-4-yl-piperidin-1-yl)-methanone | 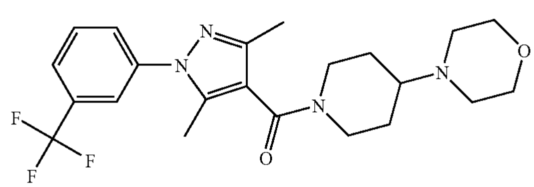 | 4-Piperidin-4-yl-morpholine | 437.3 |

TABLE 4-continued

| Example No. | Compound Name | Structure | Amine | MS: (MH+) |
|---|---|---|---|---|
| 84 | 8-[3,5-Dimethyl-1-(3-trifluoromethyl-phenyl)-1H-pyrazol-4-carbonyl]-1-oxa-3,8-diaza-spiro[4.5]decan-2-one | 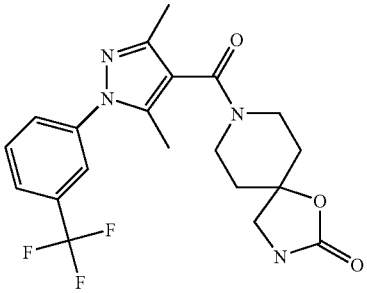 | 1-Oxa-3,8-diaza-spiro[4.5]decan-2-one (Intermediate 34) | 423.2 |
| 85 | [1,4']Bipiperidinyl-1'-yl-[3,5-dimethyl-1-(3-trifluoromethyl-phenyl)-1H-pyrazol-4-yl]-methanone | 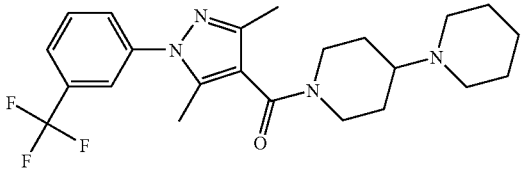 | [1,4']Bipiperidinyl | 435.3 |
| 86 | [3,5-Dimethyl-1-(3-trifluoromethyl-phenyl)-1H-pyrazol-4-yl]-{(R)-3-[methyl-(tetrahydro-pyran-4-yl)-amino]-pyrrolidin-1-yl}-methanone | 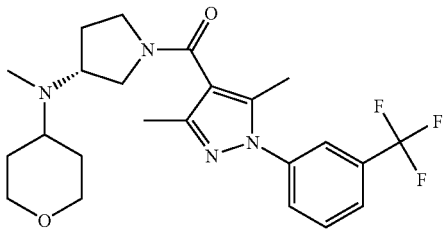 | Methyl-(R)-pyrrolidin-3-yl-(tetrahydro-pyran-4-yl)-amine (Intermediate 18) | 451.3 |

Example 87-97

General Procedure for Examples 87-97

A solution of intermediate 8 (0.05 mol), Et$_3$N (0.3 mmol), HATU (0.06 mmol) and appropriate amine (0.1 mmol) in DMF (0.5 ml) were shaken for 16 h and the products purified directly by preparative HPLC.

TABLE 5

| Example No. | Compound Name | Structure | Amine | MS: (MH+) |
|---|---|---|---|---|
| 87 | [3,5-Dimethyl-1-(3-trifluoromethoxy-phenyl)-1H-pyrazol-4-yl]-(4-isopropyl-piperazin-1-yl)-methanone | 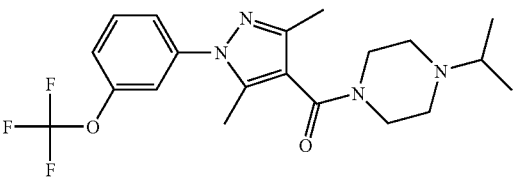 | 1-Isopropyl-piperazine | 411.2 |
| 88 | [3,5-Dimethyl-1-(3-trifluoromethoxy-phenyl)-1H-pyrazol-4-yl]-(3-hydroxy-[1,4']bipiperidinyl-1'-yl)-methanone | 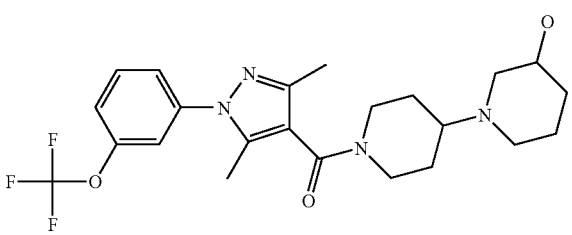 | [1,4']Bipiperidinyl-3-ol | 467.3 |

TABLE 5-continued

| Example No. | Compound Name | Structure | Amine | MS: (MH⁺) |
|---|---|---|---|---|
| 89 | (4-Cyclopentyl-piperazin-1-yl)-[3,5-dimethyl-1-(3-trifluoromethoxy-phenyl)-1H-pyrazol-4-yl]-methanone | 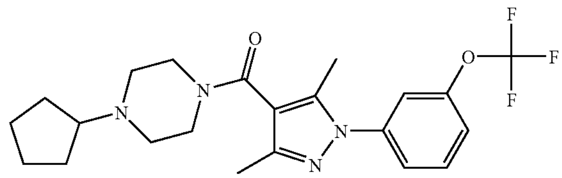 | 1-Cyclopentyl-piperazine | 437.3 |
| 90 | [3,5-Dimethyl-1-(3-trifluoromethoxy-phenyl)-1H-pyrazol-4-yl]-(4-hydroxy-[1,4']bipiperidinyl-1'-yl)-methanone | 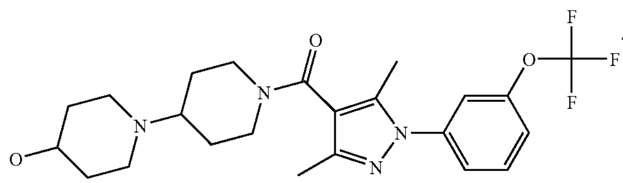 | [1,4']Bipiperidinyl-4-ol | 467.3 |
| 91 | (3-Diethylamino-pyrrolidin-1-yl)-[3,5-dimethyl-1-(3-trifluoromethoxy-phenyl)-1H-pyrazol-4-yl]-methanone | 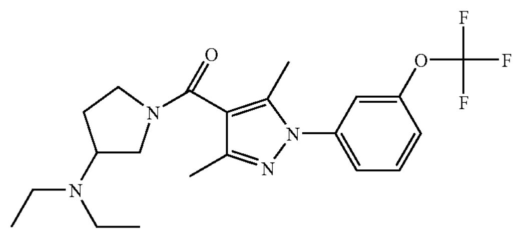 | Diethyl-pyrrolidin-3-yl-amine | 425.3 |
| 92 | (4-Dimethylamino-piperidin-1-yl)-[3,5-dimethyl-1-(3-trifluoromethoxy-phenyl)-1H-pyrazol-4-yl]-methanone | 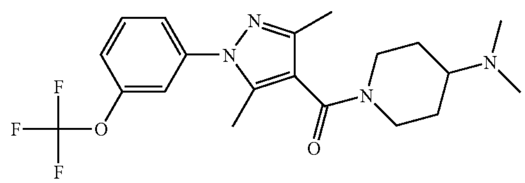 | Dimethyl-piperidin-4-yl-amine | 411.3 |
| 93 | [3,5-Dimethyl-1-(3-trifluoromethoxy-phenyl)-1H-pyrazol-4-yl]-(4-pyrrolidin-1-yl-piperidin-1-yl)-methanone | 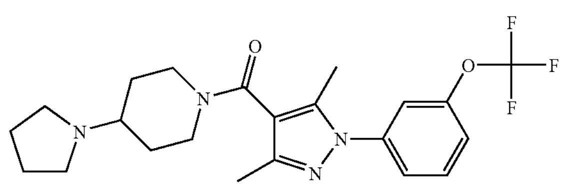 | 4-Pyrrolidin-1-yl-piperidine | 437.3 |
| 94 | [3,5-Dimethyl-1-(3-trifluoromethoxy-phenyl)-1H-pyrazol-4-yl]-(4-morpholin-4-yl-piperidin-1-yl)-methanone | 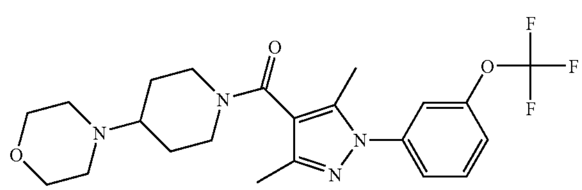 | 4-Piperidin-4-yl-morpholine | 453.2 |
| 95 | 8-[3,5-Dimethyl-1-(3-trifluoromethoxy-phenyl)-1H-pyrazole-4-carbonyl]-1-oxa-3,8-diaza-spiro[4.5]decan-2-one | 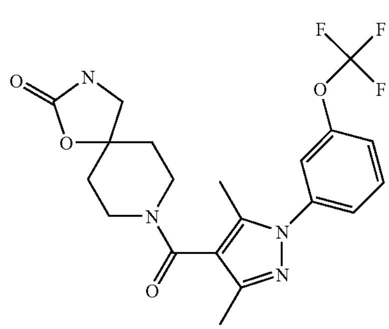 | 1-Oxa-3,8-diaza-spiro[4.5]decan-2-one (Intermediate 34) | 439.2 |

TABLE 5-continued

| Example No. | Compound Name | Structure | Amine | MS: (MH+) |
|---|---|---|---|---|
| 96 | [1,4']Bipiperidinyl-1'-yl-[3,5-dimethyl-1-(3-trifluoromethoxy-phenyl)-1H-pyrazol-4-yl]-methanone | 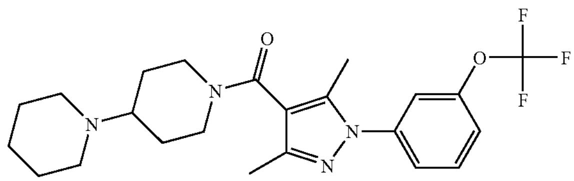 | [1,4']Bipiperidinyl | 451.3 |
| 97 | [3,5-Dimethyl-1-(3-trifluoromethoxy-phenyl)-1H-pyrazol-4-yl]-{(R)-3-[methyl-(tetrahydro-pyran-4-yl)-amino]-pyrrolidin-1-yl}-methanone | 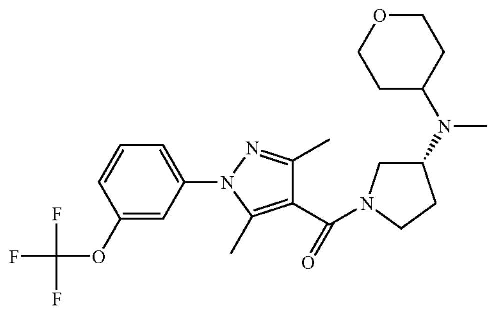 | Methyl-(R)-pyrrolidin-3-yl-(tetrahydro-pyran-4-yl)-amine (Intermediate 18) | 467.3 |

Example 98-104

General Procedure for Examples 98-104

A solution of intermediate 16 (0.05 mol), Et₃N (0.3 mmol), HATU (0.06 mmol) and appropriate amine (0.1 mmol) in DMF (0.5 ml) were shaken for 16 h and the products purified directly by preparative HPLC.

TABLE 6

| Example No. | Compound Name | Structure | Amine | MS: (MH+) |
|---|---|---|---|---|
| 98 | [3,5-Dicyclopropyl-1-(3-trifluoromethyl-phenyl)-1H-pyrazol-4-yl]-(3-hydroxy-[1,4']bipiperidinyl-1'-yl)-methanone | 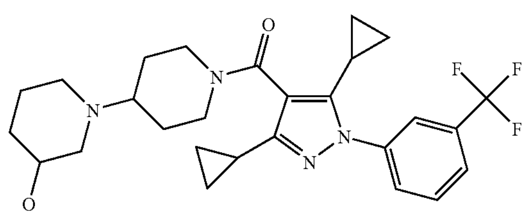 | [1,4']Bipiperidinyl-3-ol | 503.3 |
| 99 | (4-Cyclopentyl-piperazin-1-yl)-[3,5-dicyclopropyl-1-(3-trifluoromethyl-phenyl)-1H-pyrazol-4-yl]-methanone | 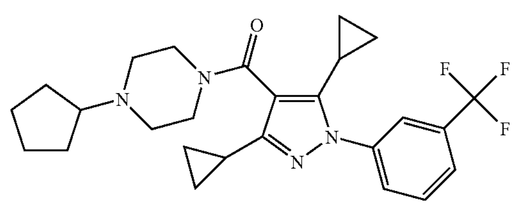 | 1-Cyclopentyl-piperazine | 473.3 |
| 100 | [3,5-Dicyclopropyl-1-(3-trifluoromethyl-phenyl)-1H-pyrazol-4-yl]-(4-hydroxy-[1,4']bipiperidinyl-1'-yl)-methanone | 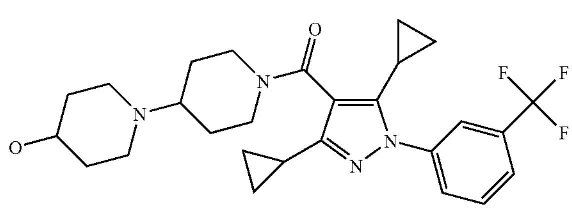 | [1,4']Bipiperidinyl-4-ol | 503.3 |

TABLE 6-continued

| Example No. | Compound Name | Structure | Amine | MS: (MH+) |
|---|---|---|---|---|
| 101 | [3,5-Dicyclopropyl-1-(3-trifluoromethyl-phenyl)-1H-pyrazol-4-yl]-(4-dimethylamino-piperidin-1-yl)-methanone | 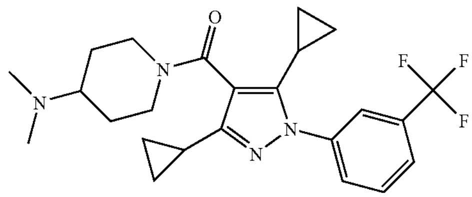 | Dimethyl-piperidin-4-yl-amine | 447.3 |
| 102 | [3,5-Dicyclopropyl-1-(3-trifluoromethyl-phenyl)-1H-pyrazol-4-yl]-(4-pyrrolidin-1-yl-piperidin-1-yl)-methanone | 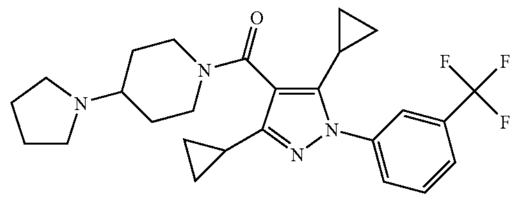 | 4-Pyrrolidin-1-yl-piperidine | 473.3 |
| 103 | [3,5-Dicyclopropyl-1-(3-trifluoromethyl-phenyl)-1H-pyrazol-4-yl]-(4-morpholin-4-yl-piperidin-1-yl)-methanone | 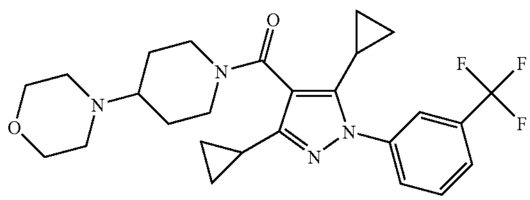 | 4-Piperidin-4-yl-morpholine | 489.3 |
| 104 | [1,4']Bipiperidinyl-1'-yl-[3,5-dicyclopropyl-1-(3-trifluoromethyl-phenyl)-1H-pyrazol-4-yl]-methanone | 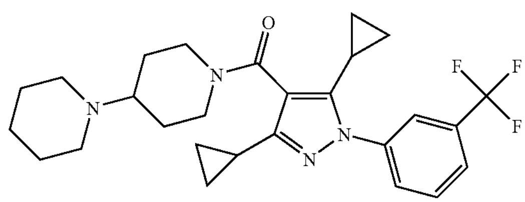 | [1,4']Bipiperidinyl | 487.3 |

Example 105-119

General Procedure for Examples 105-119

To a solution of intermediate 9 (0.05 mol) and appropriate amine (0.1 mmol) in DCE/EtOH (1:1 0.5 ml) was added acetic acid (15 ul) and pyridineborane complex (15 ul, 8 M in pyridine) and the mixture shaken for 16 h. The solutions were evaporated, the residue redissolved in DMSO and the products purified directly by preparative HPLC.

TABLE 7

| Example No. | Compound Name | Structure | Amine | MS: (MH+) |
|---|---|---|---|---|
| 105 | [3,5-Dimethyl-1-(3-trifluoromethoxy-phenyl)-1H-pyrazol-4-yl]-[4-((S)-2-hydroxymethyl-pyrrolidin-1-yl)-piperidin-1-yl]-methanone | 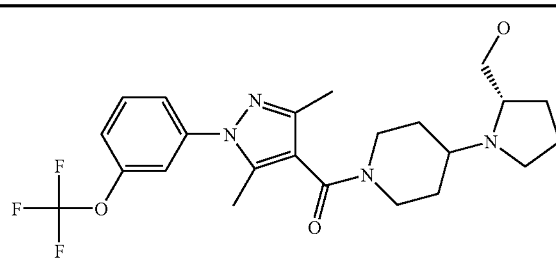 | (S)-1-Pyrrolidin-2-yl-methanol | 467.3 |

TABLE 7-continued

| Example No. | Compound Name | Structure | Amine | MS: (MH+) |
|---|---|---|---|---|
| 106 | [3,5-Dimethyl-1-(3-trifluoromethoxy-phenyl)-1H-pyrazol-4-yl]-[4-((S)-2-methoxymethyl-pyrrolidin-1-yl)-piperidin-1-yl]-methanone | 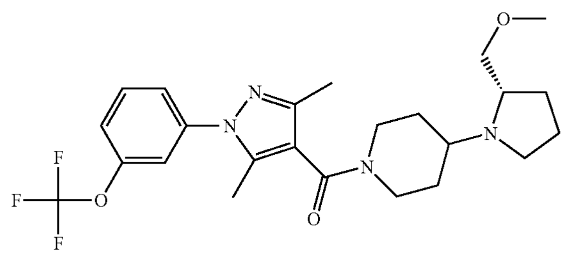 | (S)-2-Methoxymethyl-pyrrolidine | 481.3 |
| 107 | [3,5-Dimethyl-1-(3-trifluoromethoxy-phenyl)-1H-pyrazol-4-yl]-[4-((R)-2-hydroxymethyl-pyrrolidin-1-yl)-piperidin-1-yl]-methanone | 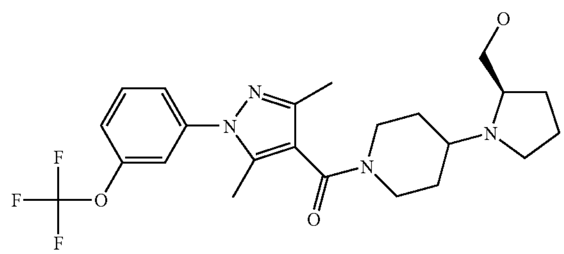 | (R)-1-Pyrrolidin-2-yl-methanol | 467.3 |
| 108 | N-(1-{1-[3,5-Dimethyl-1-(3-trifluoromethoxy-phenyl)-1H-pyrazole-4-carbonyl]-piperidin-4-yl}-pyrrolidin-3-yl)-acetamide | 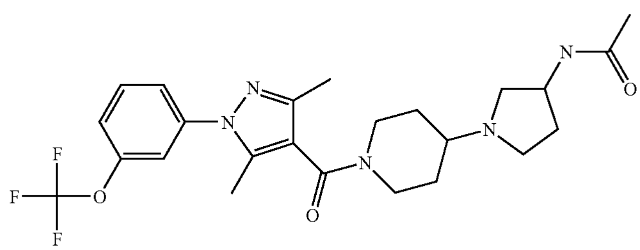 | N-Pyrrolidin-3-yl-acetamide | 494.3 |
| 109 | [3,5-Dimethyl-1-(3-trifluoromethoxy-phenyl)-1H-pyrazol-4-yl]-[4-(2-methyl-pyrrolidin-1-yl)-piperidin-1-yl]-methanone | 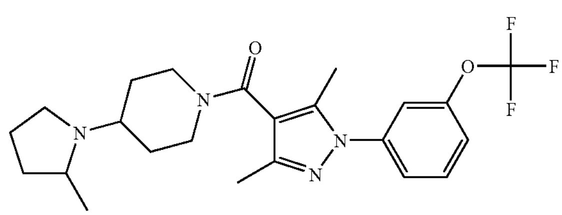 | 2-Methyl-pyrrolidine | 451.3 |
| 110 | [3,5-Dimethyl-1-(3-trifluoromethoxy-phenyl)-1H-pyrazol-4-yl]-[4-((R)-3-hydroxy-pyrrolidin-1-yl)-piperidin-1-yl]-methanone | 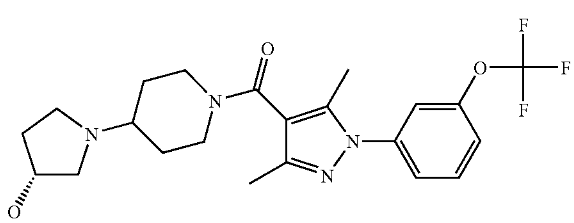 | (R)-Pyrrolidin-3-ol | 453.3 |
| 111 | [3,5-Dimethyl-1-(3-trifluoromethoxy-phenyl)-1H-pyrazol-4-yl]-[4-((S)-3-hydroxy-pyrrolidin-1-yl)-piperidin-1-yl]-methanone | 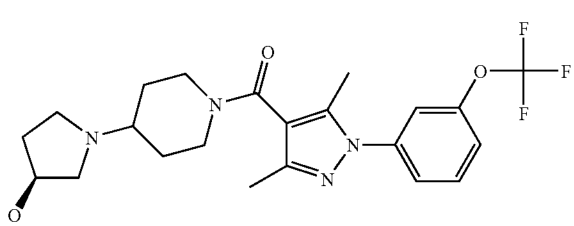 | (S)-Pyrrolidin-3-ol | 453.3 |

TABLE 7-continued

| Example No. | Compound Name | Structure | Amine | MS: (MH+) |
|---|---|---|---|---|
| 112 | [3,5-Dimethyl-1-(3-trifluoromethoxy-phenyl)-1H-pyrazol-4-yl]-(4-hydroxy-[1,4']bipiperidinyl-1'-yl)-methanone | 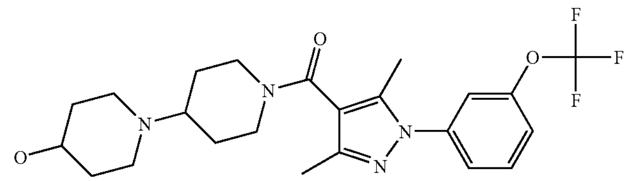 | 4-Methoxzy-piperidine | 481.3 |
| 113 | [3,5-Dimethyl-1-(3-trifluoromethoxy-phenyl)-1H-pyrazol-4-yl]-[4-(tetrahydro-pyran-4-ylamino)-piperidin-1-yl]-methanone | 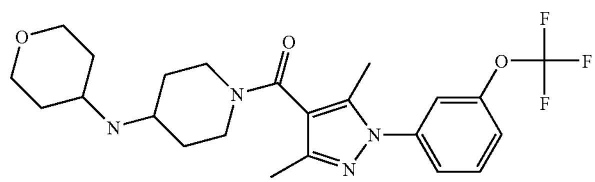 | Tetrahydro-pyran-4-ylamine | 467.3 |
| 114 | (4-Cyclopentylamino-piperidin-1-yl)-(3,5-dimethyl-1-(3-trifluoromethoxy-phenyl)-1H-pyrazol-4-yl]-methanone | 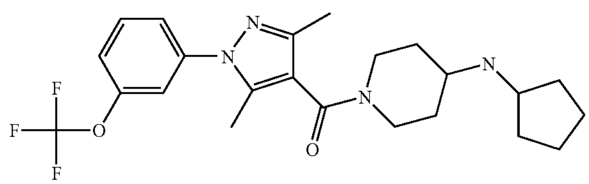 | Cyclopentylamine | 451.3 |
| 115 | [3,5-Dimethyl-1-(3-trifluoromethoxy-phenyl)-1H-pyrazol-4-yl]-[4-((cis)-3-methoxy-tetrahydro-pyran-4-ylamino)-piperidin-1-yl]-methanone | 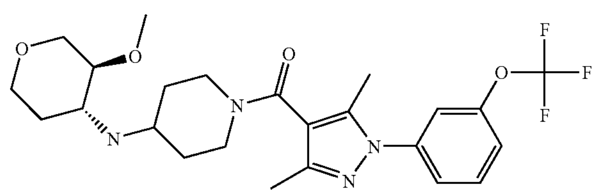 | (cis)-3-Methoxy-tetrahydro-pyran-4-ylamine (Intermediate 36) | 497.3 |
| 116 | [3,5-Dimethyl-1-(3-trifluoromethoxy-phenyl)-1H-pyrazol-4-yl]-[4-(3-methyl-pyrrolidin-1-yl)-piperidin-1-yl]-methanone | 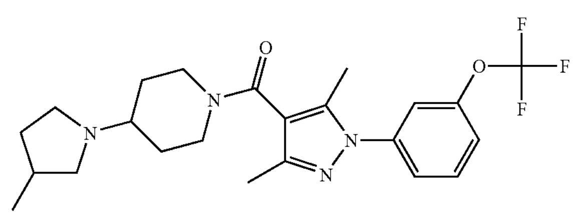 | 3-Methyl-pyrrolidine (Intermediate 22) | 451.3 |
| 117 | [3,5-Dimethyl-1-(3-trifluoromethoxy-phenyl)-1H-pyrazol-4-yl]-[4-((trans)-3-hydroxy-4-methyl-pyrrolidin-1-yl)-piperidin-1-yl]-methanone | 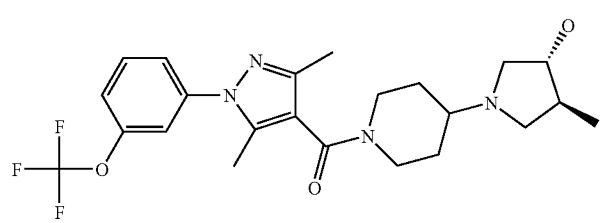 | (trans)-4-Methyl-pyrrolidin-3-ol (Intermediate 23) | 467.3 |
| 118 | N-((S)-1-{1-[3,5-Dimethyl-1-(3-trifluoromethoxy-phenyl)-1H-pyrazole-4-carbonyl]-piperidin-4-yl}-pyrrolidin-3-yl)-acetamide | 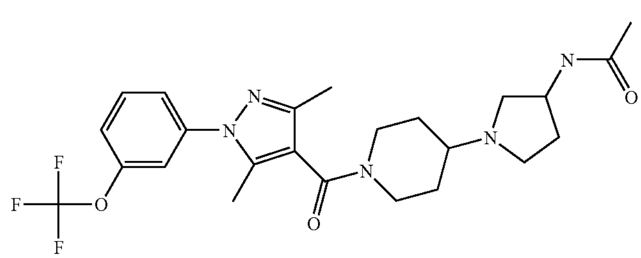 | (S)-N-Pyrrolidin-3-yl-acetamide | 494.3 |

TABLE 7-continued

| Example No. | Compound Name | Structure | Amine | MS: (MH+) |
|---|---|---|---|---|
| 119 | N-((R)-1-{1-[3,5-Dimethyl-1-(3-trifluoromethoxy-phenyl)-1H-pyrazole-4-carbonyl]-piperidin-4-yl}-pyrrolidin-3-yl)-acetamide | 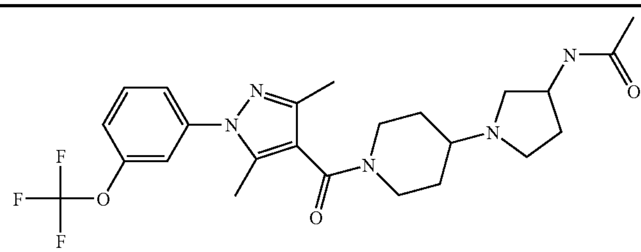 | (R)-N-Pyrrolidin-3-yl-acetamide | 494.3 |

Example 120-128

General Procedure for Examples 120-128

To a solution of intermediate 10 (0.05 mol) and appropriate amine (0.1 mmol) in DCE/EtOH (1:1 0.5 ml) was added acetic acid (15 ul) and pyridineborane complex (15 ul, 8 M in pyridine) and the mixture shaken for 16 h. The solutions were evaporated, the residue redissolved in DMSO and the products purified directly by preparative HPLC.

TABLE 8

| Example No. | Compound Name | Structure | Amine | MS: (MH+) |
|---|---|---|---|---|
| 120 | [3,5-Dimethyl-1-(3-trifluoromethoxy-phenyl)-1H-pyrazol-4-yl]-((S)-2-hydroxymethyl-[1,3']bipyrrolidinyl-1'-yl)-methanone | 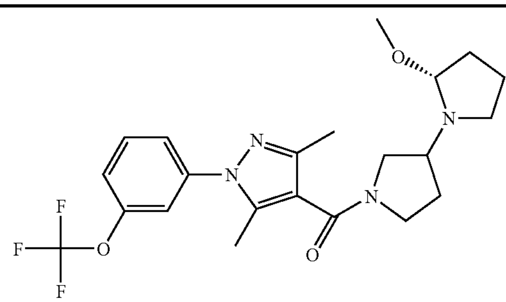 | (S)-1-Pyrrolidin-2-yl-methanol | 453.3 |
| 121 | N-{1'-[3,5-Dimethyl-1-(3-trifluoromethoxy-phenyl)-1H-pyrazol-4-carbonyl]-[1,3']bipyrrolidinyl-3-yl}-acetamide | 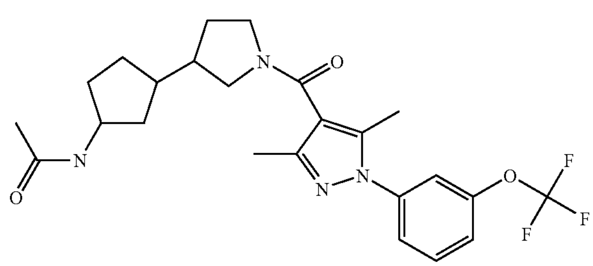 | N-Pyrrolidin-3-yl-acetamide | 480.3 |
| 122 | [3,5-Dimethyl-1-(3-trifluoromethoxy-phenyl)-1H-pyrazol-4-yl]-(2-methyl-[1,3']bipyrrolidinyl-1'-yl)-methanone | 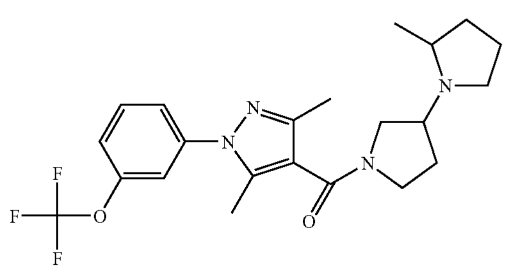 | 2-Methyl-pyrrolidine | 437.3 |

TABLE 8-continued

| Example No. | Compound Name | Structure | Amine | MS: (MH+) |
|---|---|---|---|---|
| 123 | [3,5-Dimethyl-1-(3-trifluoromethoxy-phenyl)-1H-pyrazol-4-yl]-((R)-3-hydroxy-[1,3']bipyrrolidinyl-1'-yl)-methanone | 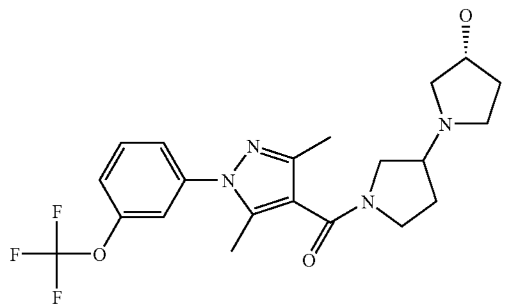 | (R)-Pyrrolidin-3-ol | 439.3 |
| 124 | [3,5-Dimethyl-1-(3-trifluoromethoxy-phenyl)-1H-pyrazol-4-yl]-(2-hydroxymethyl-2-[1,3']bipyrrolidinyl-1'-yl)-methanone | 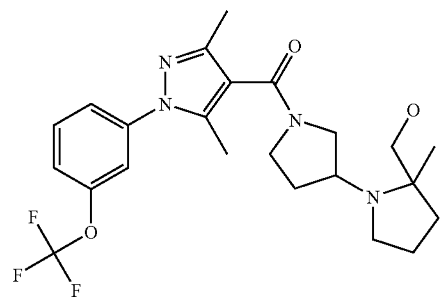 | (2-Methyl-pyrrolidin-2-yl)-methanol | 467.3 |
| 125 | [3,5-Dimethyl-1-(3-trifluoromethoxy-phenyl)-1H-pyrazol-4-yl]-[3-(tetrahydro-pyran-4-ylamino)-pyrrolidinyl-1-yl]-methanone | 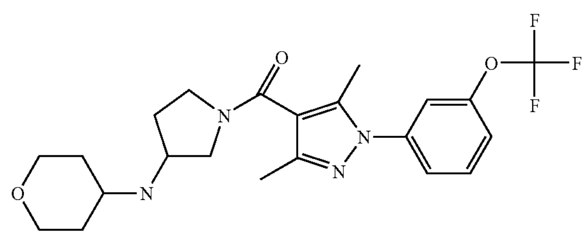 | Tetrahydro-pyran-4-ylamine | 453.1 |
| 126 | (3-Cyclopentylamino-pyrrolidin-1-yl)-[3,5-dimethyl-1-(3-trifluoromethoxy-phenyl)-1H-pyrazol-4-yl]-methanone | 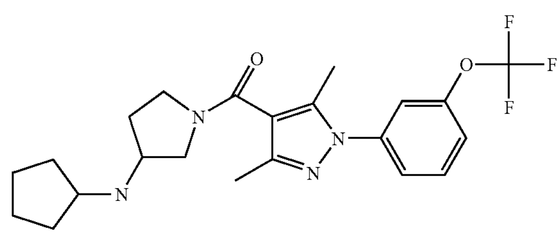 | Cyclopentylamine | 437.3 |
| 127 | [3,5-Dimethyl-1-(3-trifluoromethoxy-phenyl)-1H-pyrazol-4-yl]-((R)-2-hydroxymethyl-[1,3']bipyrrolidinyl-1'-yl)-methanone | 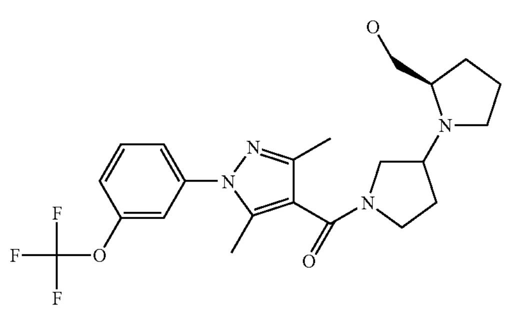 | (R)-1-Pyrrolidin-2-yl-methanol | 453.3 |

TABLE 8-continued

| Example No. | Compound Name | Structure | Amine | MS: (MH+) |
|---|---|---|---|---|
| 128 | [3,5-Dimethyl-1-(3-trifluoromethoxy-phenyl)-1H-pyrazol-4-yl]-((S)-3-hydroxy-[1,3']bipyrrolidinyl-1'-yl)-methanone | 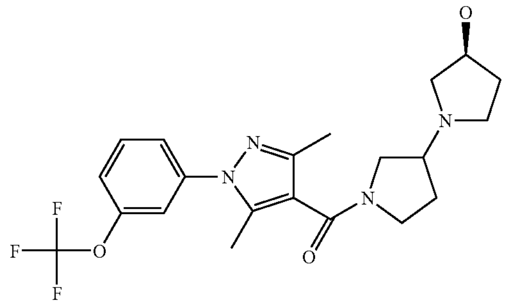 | (S)-Pyrrolidin-3-ol | 439.3 |

Example 129-149

General Procedure for Examples 129-149

To a solution of intermediate 15 (0.05 mol) and appropriate amine (0.1 mmol) in DCE/EtOH (1:1 0.5 ml) was added acetic acid (15 ul) and pyridineborane complex (15 ul, 8 M in pyridine) and the mixture shaken for 16 h. The solutions were evaporated, the residue redissolved in DMSO and the products purified directly by preparative HPLC.

TABLE 9

| Example No. | Compound Name | Structure | Amine | MS: (MH+) |
|---|---|---|---|---|
| 129 | [5-Cyclopropyl-3-methyl-1-(3-trifluoromethoxy-phenyl)-1H-pyrazol-4-yl]-[4-(3-methyl-pyrrolidin-1-yl)-piperidin-1-yl]-methanone | 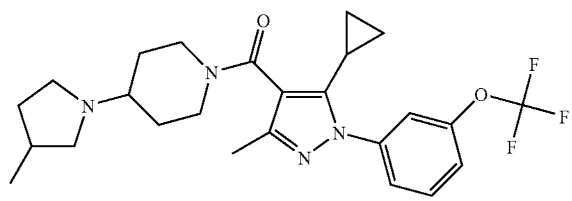 | 3-Methyl-pyrrolidine (Intermediate 22) | 477.2 |
| 130 | [5-Cyclopropyl-3-methyl-1-(3-trifluoromethoxy-phenyl)-1H-pyrazol-4-yl]-[4-(2-methyl-pyrrolidin-1-yl)-piperidin-1-yl]-methanone | 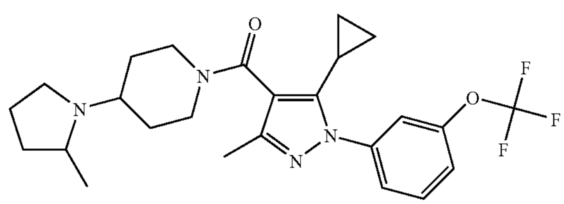 | 2-Methyl-pyrrolidine | 477.2 |
| 131 | [5-Cyclopropyl-3-methyl-1-(3-trifluoromethoxy-phenyl)-1H-pyrazol-4-yl]-[4-((S)-2-hydroxymethyl-pyrrolidin-1-yl)-piperidin-1-yl]-methanone | 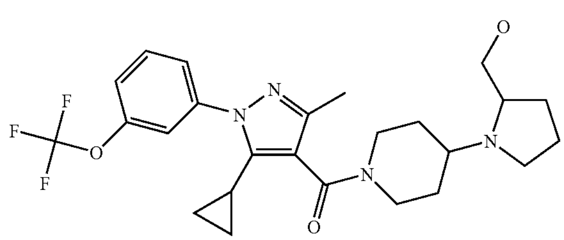 | (S)-1-Pyrrolidin-2-yl-methanol | 493.2 |
| 132 | [5-Cyclopropyl-3-methyl-1-(3-trifluoromethoxy-phenyl)-1H-pyrazol-4-yl]-[4-((S)-3-hydroxy-pyrrolidin-1-yl)-piperidin-1-yl]-methanone | 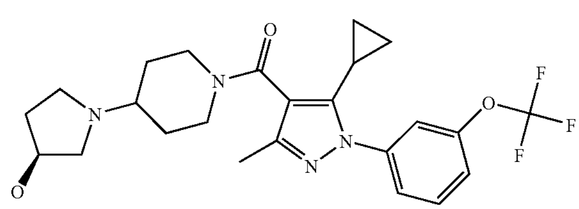 | (S)-Pyrrolidin-3-ol | 479.3 |

TABLE 9-continued

| Example No. | Compound Name | Structure | Amine | MS: (MH+) |
|---|---|---|---|---|
| 133 | [5-Cyclopropyl-3-methyl-1-(3-trifluoromethoxyphenyl)-1H-pyrazol-4-yl]-[4-((trans)-3-hydroxy-4-methyl-pyrrolidin-1-yl)-piperidin-1-yl]-methanone | 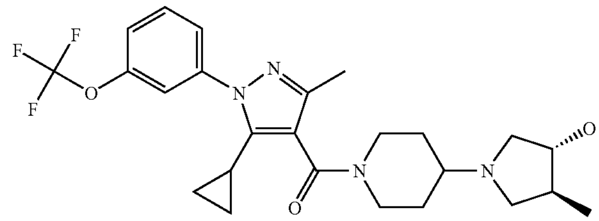 | (trans)-4-Methyl-pyrrolidin-3-ol (Intermediate 23) | 493.5 |
| 134 | [5-Cyclopropyl-3-methyl-1-(3-trifluoromethoxyphenyl)-1H-pyrazol-4-yl]-[4-((cis)-3-hydroxy-4-methyl-pyrrolidin-1-yl)-piperidin-1-yl]-methanone | 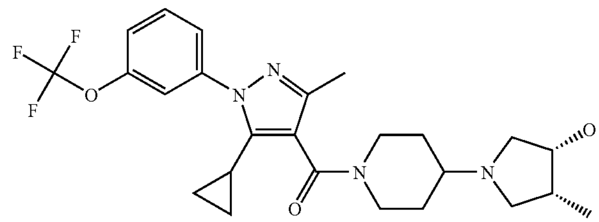 | (cis)-4-Methyl-pyrrolidin-3-ol (Intermediate 24) | 493.5 |
| 135 | [5-Cyclopropyl-3-methyl-1-(3-trifluoromethoxyphenyl)-1H-pyrazol-4-yl]-[4-((2S,4R)-4-hydroxy-2-methyl-pyrrolidin-1-yl)-piperidin-1-yl]-methanone | 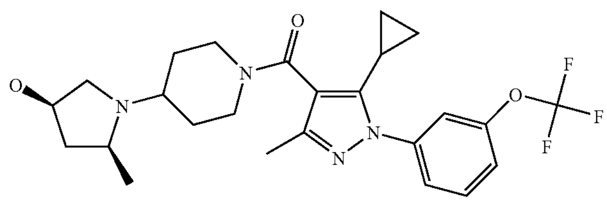 | (3R,5S)-5-Methyl-pyrrolidin-3-ol (Intermediate 26) | 493.5 |
| 136 | [5-Cyclopropyl-3-methyl-1-(3-trifluoromethoxyphenyl)-1H-pyrazol-4-yl]-[4-((2S,4S)-4-hydroxy-2-methyl-pyrrolidin-1-yl)-piperidin-1-yl]-methanone | 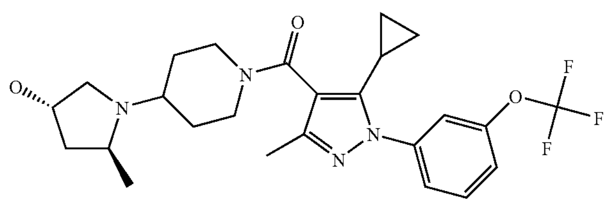 | (3S,5S)-5-Methyl-pyrrolidin-3-ol (Intermediate 28) | 493.2 |
| 137 | [5-Cyclopropyl-3-methyl-1-(3-trifluoromethoxyphenyl)-1H-pyrazol-4-yl]-[4-((2R,4R)-4-hydroxy-2-methyl-pyrrolidin-1-yl)-piperidin-1-yl]-methanone | 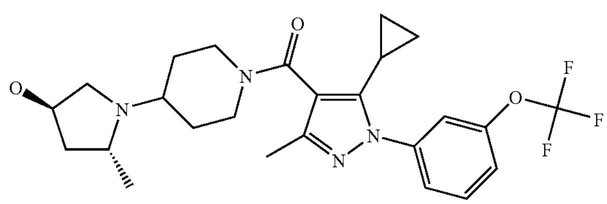 | (3R,5R)-5-Methyl-pyrrolidin-3-ol (Intermediate 27) | 493.2 |
| 138 | [5-Cyclopropyl-3-methyl-1-(3-trifluoromethoxyphenyl)-1H-pyrazol-4-yl]-[4-((2R,4S)-4-hydroxy-2-methyl-pyrrolidin-1-yl)-piperidin-1-yl]-methanone | 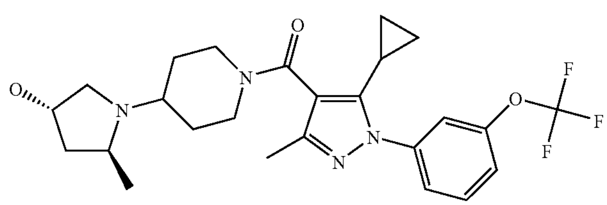 | (3R,5R)-5-Methyl-pyrrolidin-3-ol (Intermediate 29) | 493.2 |

TABLE 9-continued

| Example No. | Compound Name | Structure | Amine | MS: (MH+) |
|---|---|---|---|---|
| 139 | 7-{1-[5-Cyclopropyl-3-methyl-1-(3-trifluoromethoxy-phenyl)-1H-pyrazole-4-carbonyl]-piperidin-4-yl}-1,3,7-triaza-spiro[4.4]nonane-2,4-dione | 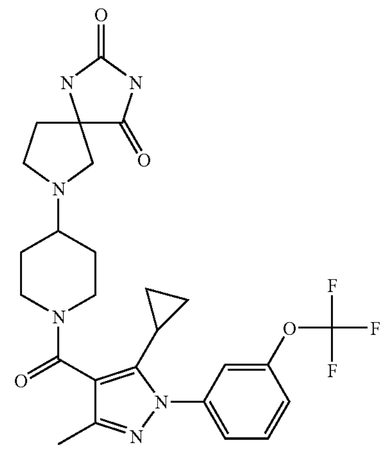 | 1,3,7-Triaza spiro[4.4]nonane-2,4-dione (Intermediate 33) | 547.2 |
| 140 | N-((trans)-1-{1-[5-Cyclopropyl-3-methyl-1-(3-trifluoromethoxy-phenyl)-1H-pyrazole-4-carbonyl]-piperidin-4-yl}-4-hydroxy-pyrrolidin-3-yl)-acetamide | 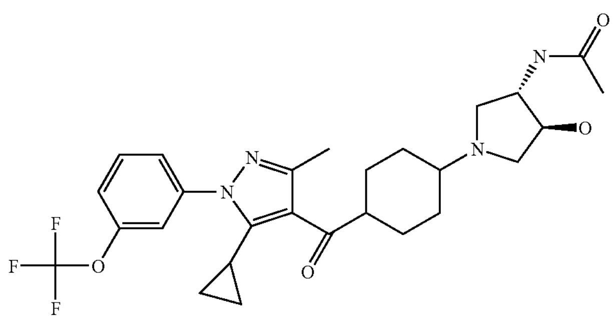 | N-((trans)-4-Hydroxy-pyrrolidin-3-yl)-acetamide (Intermediate 21) | 536.3 |
| 141 | [5-Cyclopropyl-3-methyl-1-(3-trifluoromethoxy-phenyl)-1H-pyrazol-4-yl]-[4-(2S,3R)-3-hydroxy-2-methyl-pyrrolidin-1-yl]-piperidin-1-yl]-methanone | 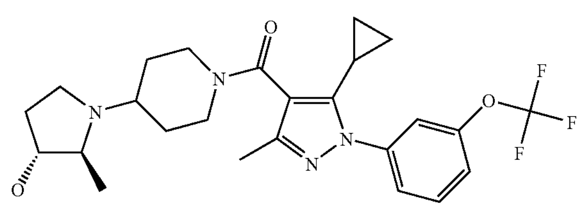 | (2S,3R)-2-Methyl-pyrrolidin-3-ol (Intermediate 30) | 493.2 |
| 142 | [5-Cyclopropyl-3-methyl-1-(3-trifluoromethoxy-phenyl)-1H-pyrazol-4-yl]-[4-(3-hydroxy-3-methyl-pyrrolidin-1-yl)-piperidin-1-yl]-methanone | 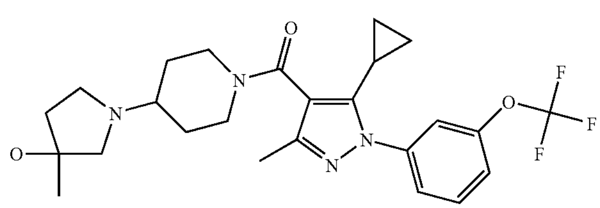 | 3-Methyl-pyrrolidin-3-ol (Intermediate 25) | 493.5 |
| 143 | [5-Cyclopropyl-3-methyl-1-(3-trifluoromethoxy-phenyl)-1H-pyrazol-4-yl]-[4-((R)-2-hydroxymethyl-pyrrolidin-1-yl)-piperidin-1-yl]-methanone | 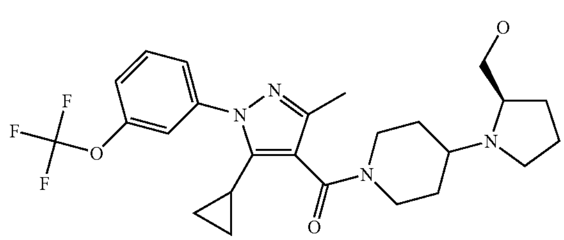 | (R)-1-Pyrrolidin-2-yl-methanol | 493.2 |

TABLE 9-continued

| Example No. | Compound Name | Structure | Amine | MS: (MH+) |
|---|---|---|---|---|
| 144 | [5-Cyclopropyl-3-methyl-1-(3-trifluoromethoxy-phenyl)-1H-pyrazol-4-yl]-[4-((R)-3-hydroxy-pyrrolidin-1-yl)-piperidin-1-yl]-methanone | 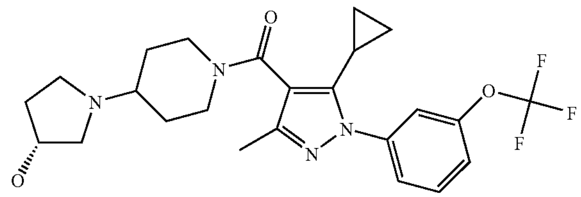 | (R)-Pyrrolidin-3-ol | 479.2 |
| 145 | N-((R)-1-{1-[5-Cyclopropyl-3-methyl-1-(3-trifluoromethoxy-phenyl)-1H-pyrazole-4-carbonyl]-piperidin-4-yl}-pyrrolidin-3-yl)-acetamide | 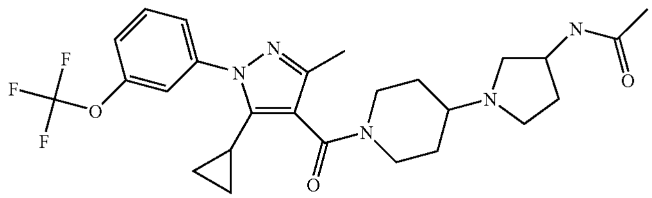 | (R)-N-Pyrrolidin-3-yl)-acetamide | 520.2 |
| 146 | N-((S)-1-{1-[5-Cyclopropyl-3-methyl-1-(3-trifluoromethoxy-phenyl)-1H-pyrazole-4-carbonyl]-piperidin-4-yl}-pyrrolidin-3-yl)-acetamide | 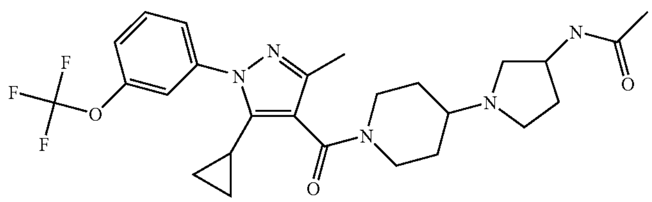 | (S)-N-Pyrrolidin-3-yl)-acetamide | 520.2 |
| 147 | (4-Azetidin-1-yl-piperidin-1-yl)-[5-cyclopropyl-3-methyl-1-(3-trifluoromethoxy-phenyl)-1H-pyrazol-4-yl]-methanone | 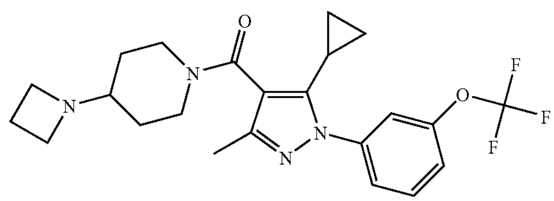 | Azetidine | 449.2 |
| 148 | [5-Cyclopropyl-3-methyl-1-(3-trifluoromethoxy-phenyl)-1H-pyrazol-4-yl]-[4-(3-hydroxy-azetidin-1-yl)-piperidin-1-yl]-methanone | 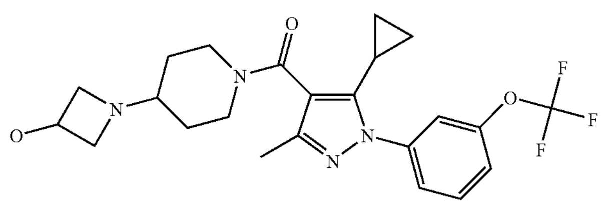 | Azetidin-3-ol | 465.2 |
| 149 | [5-Cyclopropyl-3-methyl-1-(3-trifluoromethoxy-phenyl)-1H-pyrazol-4-yl]-{4-[(2-hydroxy-ethyl)-methyl-amino]-piperidin-1-yl}-methanone | 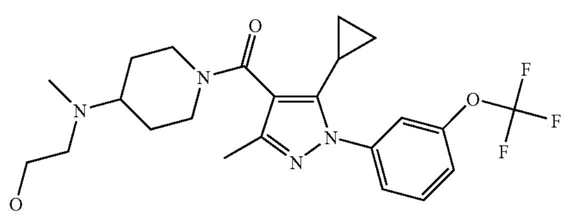 | 2-Methylamino-ethanol | 467.4 |

Example 150-151

General Procedure for Examples 150-151

A solution of intermediate 14 (0.05 mol), Et$_3$N (0.3 mmol), HATU (0.06 mmol) and appropriate amine (0.1 mmol) in DMF (0.5 ml) were shaken for 16 h and the products purified directly by preparative HPLC.

TABLE 10

| Example No. | Compound Name | Structure | Amine | MS: (MH+) |
|---|---|---|---|---|
| 150 | [5-Cyclopropyl-3-methyl-1-(3-trifluoromethoxy-phenyl)-1H-pyrazol-4-yl]-((trans)-4-hydroxy-3-pyrrolidin-1-yl-piperidin-1-yl)-methanone | 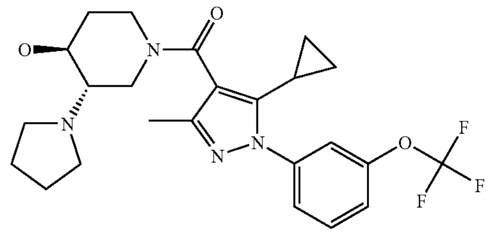 | (trans)-3-Pyrrolidin-1-yl-piperidin-4-ol (Intermediate 31) | 479.2 |
| 151 | [5-Cyclopropyl-3-methyl-1-(3-trifluoromethoxy-phenyl)-1H-pyrazol-4-yl]-[4-(2-hydroxymethyl-2-methyl-pyrrolidin-1-yl)-piperidin-1-yl]-methanone | 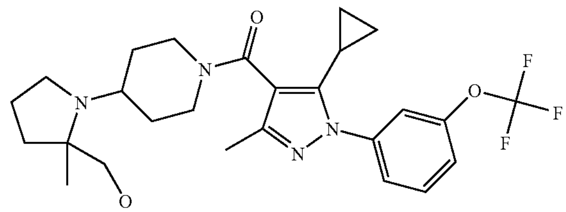 | (2-Methyl-1-piperidin-4-yl-pyrrolidin-2-yl)-methanol (Intermediate 38) | 507.3 |

Example 152

[1-(3,4-Dichloro-phenyl)-3,5-dimethyl-1H-pyrazol-4-yl]-(4-pyrrolidin-1-yl-piperidin-1-yl)-methanone

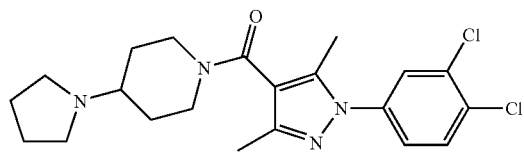

A] 1-(3,4-Dichloro-phenyl)-3,5-dimethyl-1H-pyrazole-4-carboxylic acid ethyl ester In analogy to the procedure described in Example 38A], 3,4-dichlorophenylhydrazine hydrochloride and ethyl diacetoacetate gave the title compound in 32% yield as yellow solid. MS: 313.0 (MH+, 2 Cl).

B] 1-(3,4-Dichloro-phenyl)-3,5-dimethyl-1H-pyrazole-4-carboxylic acid

In analogy to the procedure described in Example 12C], 1-(3,4-dichloro-phenyl)-3,5-dimethyl-1-pyrazole-4-carboxylic acid ethyl ester gave after acidification and extraction (CH$_2$Cl$_2$) from the water phase the title compound in 64% yield as off-white solid. MS: 282.9 (M–H⁻, 2 Cl.

C] [1-(3,4-Dichloro-phenyl)-3,5-dimethyl-1H-pyrazol-4-yl]-(4-pyrrolidin-1-yl-piperidin-1-yl)-methanone In analogy to the procedure described in Example 181, 1-(3,4-Dichloro-phenyl)-3,5-dimethyl-1H-pyrazole-4-carboxylic acid and 4-pyrrolidine-1-yl-piperidine gave the title compound in 87% yield as white foam. MS: 421.2 (MH+, 2 Cl).

Example 153

[1-(3-Chloro-phenyl)-3,5-dimethyl-1H-pyrazol-4-yl]-(4-pyrrolidin-1-yl-piperidin-1-yl)-methanone

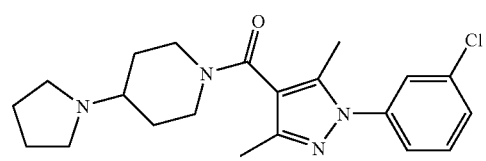

A] 1-(3-Chloro-phenyl)-3,5-dimethyl-1H-pyrazole-4-carboxylic acid ethyl ester

In analogy to the procedure described in Example 38A], 3-chlorophenylhydrazine hydrochloride and ethyl diacetoacetate gave the title compound after purification by flash column chromatography (n-heptane:EtOAc 9:1-1:1) in 58% yield as light yellow solid. MS: 279.0 (MH+, 1 Cl).

B] 1-(3-Chloro-phenyl)-3,5-dimethyl-1H-pyrazole-4-carboxylic acid

In analogy to the procedure described in Example 12C], 1-(3-chloro-phenyl)-3,5-dimethyl-1H-pyrazole-4-carboxylic acid ethyl ester gave after acidification and extraction (Et$_2$O) from the water phase the title compound in 71% yield as off-white solid. MS: 249.1 (M–H¹, Cl).

C][[1-(3-Chloro-phenyl)-3,5-dimethyl-1H-pyrazol-4-yl]]-(4-pyrrolidin-1-yl-piperidin-1-yl)-methanone In analogy to the procedure described in Example 18], 1-(3-chloro-phenyl)-3,5-dimethyl-1H-pyrazole-4-carboxylic acid and 4-pyrrolidine-1-yl-piperidine gave the title compound in 98% yield as light brown solid. MS: 387.3 (MH+, Cl).

Example 154

[3,5-Dimethyl-1-(4-methyl-3-trifluoromethyl-phenyl)-1H-pyrazol-4-yl]-(4-pyrrolidin-1-yl-piperidin-1-yl)-methanone

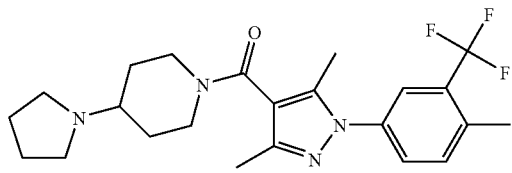

A] (4-Methyl-3-trifluoromethyl-phenyl)-hydrazine

In analogy to the procedure described in Example 42A], 4-methyl-3-(trifluoromethyl)aniline gave the title compound in 93% yield as orange liquid. MS: 191.2 (MH$^+$).

B] 3,5-Dimethyl-1-(4-methyl-3-trifluoromethyl-phenyl)-1H-pyrazole-4-carboxylic acid ethyl ester In analogy to the procedure described in Example 38A], (4-methyl-3-trifluoromethyl-phenyl)-hydrazine and ethyl diacetoacetate gave the title compound after crystallisation (EtOAc) in 96% yield as red oil. MS: 327.3 (MH$^+$).

C] 3,5-Dimethyl-1-(4-methyl-3-trifluoromethyl-phenyl)-1H-pyrazole-4-carboxylic acid In analogy to the procedure described in Example 12C], 3,5-dimethyl-1-(4-methyl-3-trifluoromethyl-phenyl)-1H-pyrazole-4-carboxylic acid ethyl ester gave after acidification and extraction (Et$_2$O) from the water phase the title compound in 89% yield as light brown solid. MS: 299.1 (M+H$^+$).

D] [3,5-Dimethyl-1-(4-methyl-3-trifluoromethyl-phenyl)-1H-pyrazol-4-yl]-(4-pyrrolidin-1-yl-piperidin-1-yl)-methanone In analogy to the procedure described in Example 18], 3,5-dimethyl-1-(4-methyl-3-trifluoromethyl-phenyl)-1H-pyrazole-4-carboxylic acid and 4-pyrrolidine-1-yl-piperidine gave the title compound in 77% yield as orange foam. MS: 435.5 (MH$^+$).

Example 155

[3-Methoxymethyl-5-methyl-1-(3-trifluoromethyl-phenyl)-1H-pyrazol-4-yl]-(4-pyrrolidin-1-yl-piperidin-1-yl)-methanone

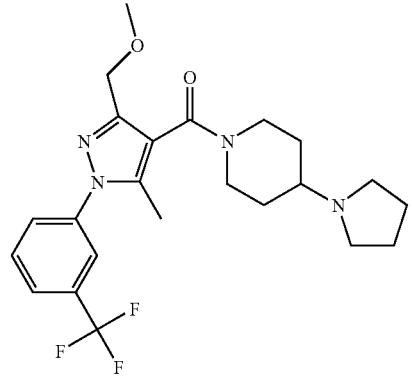

A] rac-2-Acetyl-4-methoxy-3-oxo-butyric acid ethyl ester

In analogy to the procedure described in Intermediate 11A], ethyl acetoacetate and methoxyacetylchloride gave the crude title compound in quantitative yield as yellow oil. MS: 202.9 (MH$^+$).

B] 5-Methoxymethyl-3-methyl-1-(3-trifluoromethyl-phenyl)-1H-pyrazole-4-carboxylic acid ethyl ester and 3-Methoxymethyl-5-methyl-1-(3-trifluoromethyl-phenyl)-1H-pyrazole-4-carboxylic acid ethyl ester In analogy to the procedure described in Example 38A], 3-(trifluoromethyl)phenylhydrazine and rac-2-acetyl-4-methoxy-3-oxo-butyric acid ethyl ester gave after purification by flash column chromatography (CH$_2$Cl$_2$ to 5% Et$_2$O/CH$_2$Cl$_2$) 5-methoxymethyl-3-methyl-1-(3-trifluoromethyl-phenyl)-1H-pyrazole-4-carboxylic acid ethyl ester and in 25% yield as light brown solid. MS: 343.0 (MH$^+$) and 3-methoxymethyl-5-methyl-1-(3-trifluoromethyl-phenyl)-1H-pyrazole-4-carboxylic acid ethyl ester and in 36% yield as orange oil. MS: 343.0 (MH$^+$).

C] 3-Methoxymethyl-5-methyl-1-(3-trifluoromethyl-phenyl)-1H-pyrazole-4-carboxylic acid In analogy to the procedure described in Example 12C], 3-methoxymethyl-5-methyl-1-(3-trifluoromethyl-phenyl)-1H-pyrazole-4-carboxylic acid ethyl ester gave after acidification and filtration the title compound in 89% yield as off-white powder. MS: 313.0 (M−H$^-$).

D] [3-Methoxymethyl-5-methyl-1-(3-trifluoromethyl-phenyl)-1H-pyrazol-4-yl]-(4-pyrrolidin-1-yl-piperidin-1-yl)-methanone In analogy to the procedure described in Example 18], 3-methoxymethyl-5-methyl-1-(3-trifluoromethyl-phenyl)-1H-pyrazole-4-carboxylic acid and 4-pyrrolidine-1-yl-piperidine gave the title compound in 94% yield as light yellow viscous oil. MS: 451.2 (MH$^+$).

Example 156

[3-Hydroxymethyl-5-methyl-1-(3-trifluoromethyl-phenyl)-1H-pyrazol-4-yl]-(4-pyrrolidin-1-yl-piperidin-1-yl)-methanone

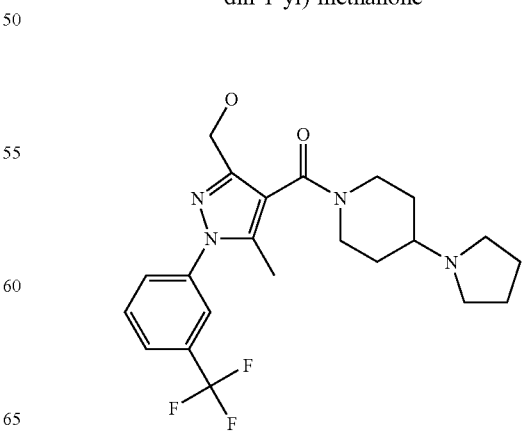

To a solution of 99 mg (0.22 mmol) [3-methoxymethyl-5-methyl-1-(3-trifluoromethyl-phenyl)-1H-pyrazol-4-yl]-(4-pyrrolidin-1-yl-piperidin-1-yl)-methanone (Example 155D]) in 1.8 ml of CH$_2$Cl$_2$ was treated at −30° C. with 0.28 ml BBr$_3$ (1M in dichloromethane, 0.28 mmol). The reaction was warmed up (0° C. for 1 h) and stirred 1.5 h at 0° C. The reaction was treated with saturated NaHCO$_3$-solution. The mixture was extracted with EtOAc (3×), the organic phase was washed with a NaCl solution (10%), dried (Na2SO4) and evaporated. The crude product was purified by flash chromatography over silica gel with CH$_2$Cl$_2$/MeOH 2.5% to 10%, to give 18 mg (19%) of the title compound as light yellow foam. MS: 437.3 (MH$^+$).

Example 157

[5-Hydroxymethyl-3-methyl-1-(3-trifluoromethyl-phenyl)-1H-pyrazol-4-yl-(4-pyrrolidin-1-yl-piperidin-1-yl)-methanone

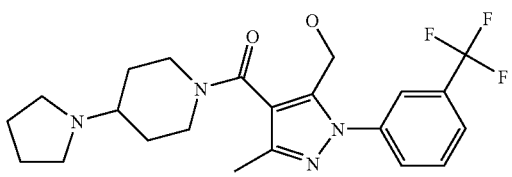

A] 5-Methoxymethyl-3-methyl-1-(3-trifluoromethyl-phenyl)-1H-pyrazole-4-carboxylic acid In analogy to the procedure described in Example 12C], 5-methoxymethyl-3-methyl-1-(3-trifluoromethyl-phenyl)-1H-pyrazole-4-carboxylic acid ethyl ester (Example 155B]) gave after acidification and filtration the title compound in 89% yield as light brown powder. MS: 313.0 (M−H$^−$).

B] [5-Methoxymethyl-3-methyl-1-(3-trifluoromethyl-phenyl)-1H-pyrazol-4-yl]-(4-pyrrolidin-1-yl-piperidin-1-yl)-methanone In analogy to the procedure described in Example 18], 5-methoxymethyl-3-methyl-1-(3-trifluoromethyl-phenyl)-1H-pyrazole-4-carboxylic acid and 4-pyrrolidine-1-yl-piperidine gave the title compound in 95% yield as light brown viscous oil. MS: 451.2 (MH$^+$).

C] [5-Hydroxymethyl-3-methyl-1-(3-trifluoromethyl-phenyl)-1H-pyrazol-4-yl]-(4-pyrrolidin-1-yl-piperidin-1-yl)-methanone In analogy to the procedure described in Example 156, [5-methoxymethyl-3-methyl-1-(3-trifluoromethyl-phenyl)-1H-pyrazol-4-yl]-(4-pyrrolidin-1-yl-piperidin-1-yl)-methanone gave the title compound in 15% yield as off-white amorphous material. MS: 437.3 (MH$^+$).

Example 158

[5-Isopropyl-3-methyl-1-(3-trifluoromethyl-phenyl)-1H-pyrazol-4-yl]-(4-pyrrolidin-1-yl-piperidin-1-yl)-methanone

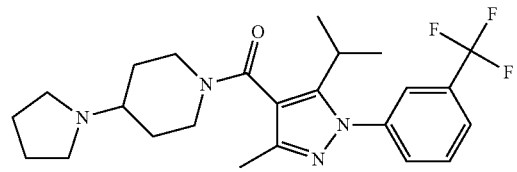

A] 5-Isopropyl-3-methyl-1-(3-trifluoromethyl-phenyl)-1H-pyrazole-4-carboxylic acid methyl ester In analogy to the procedure described in Example 38A], 3-(trifluoromethyl)phenylhydrazine and rac-2-acetyl-4-methoxy-3-oxo-pentanoic acid methyl ester gave after purification by flash column chromatography (n-heptane/AcOEt 9:1) the title compound in 65% yield as yellow oil. MS: 327.1 (MH$^+$).

B) 5-Isopropyl-3-methyl-1-(3-trifluoromethyl-phenyl)-1H-pyrazole-4-carboxylic acid In analogy to the procedure described in Example 12C], 5-isopropyl-3-methyl-1-(3-trifluoromethyl-phenyl)-1H-pyrazole-4-carboxylic acid methyl ester gave after acidification and extraction (3× Et$_2$O) the title compound in 96% yield as yellow solid. MS: 311.2 (M−H$^−$).

C] [5-Isopropyl-3-methyl-1-(3-trifluoromethyl-phenyl)-1H-pyrazol-4-yl-(4-pyrrolidin-1-yl-piperidin-1-yl)-methanone In analogy to the procedure described in Example 18], 5-isopropyl-3-methyl-1-(3-trifluoromethyl-phenyl)-1H-pyrazole-4-carboxylic acid and 4-pyrrolidine-1-yl-piperidine gave the title compound in 64% yield as light yellow oil. MS: 449.3 (MH$^+$).

Example 159

[1,4-Dimethyl-5-(3-trifluoromethyl-phenyl)-1H-pyrazol-3-yl]-(4-pyrrolidin-1-yl-piperidin-1-yl)-methanone

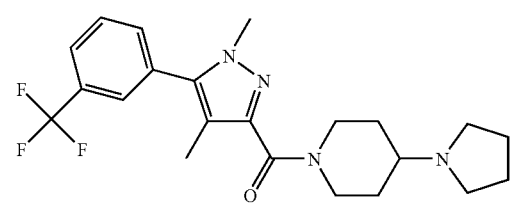

A] 1,4-Dimethyl-5-(3-trifluoromethyl-phenyl)-1H-pyrazole-3-carboxylic acid methyl ester A solution of 500 mg (2.47 mmol) of trifluoromethylpropiophenone and 0.335 mL (2.47 mmol) of diethyloxalate in 10 mL of MeOH was treated with 133 mg (2.47 mmol) of sodium methylate and stirred at room temperature for 3 hrs. The reaction was quenched by the addition of 10% aqueous $KHSO_4$ and extracted with EtOAc (3x). The organic phases were washed with 10% aqueous $KHSO_4$ and brine, dried over magnesium sulfate and evaporated to give crude 3-methyl-2,4-dioxo-4-(3-trifluoromethyl-phenyl)-butyric acid methyl ester. In analogy to the procedure described in Example 16A], crude 3-methyl-2,4-dioxo-4-(3-trifluoromethyl-phenyl)-butyric acid methyl ester and methylhydrazine gave after purification by flash column chromatography (n-heptane/AcOEt 2:1) 79.2 mg (3%) of the title compound as a rose powder. MS: 299.1 ($MH^+$).

B) 1,4-Dimethyl-5-(3-trifluoromethyl-phenyl)-1H-pyrazole-3-carboxylic acid

In analogy to the procedure described for intermediate 1E, 1,4-dimethyl-5-(3-trifluoromethyl-phenyl)-1H-pyrazole-3-carboxylic acid methyl ester has been saponified after 2 h at 60° C. to give the title compound as orange powder. MS: 285.0 ($MH^+$).

C) [1,4-Dimethyl-5-(3-trifluoromethyl-phenyl)-1H-pyrazol-3-yl]-(4-pyrrolidin-1-yl-piperidin-1-yl)-methanone In analogy to the procedure described for Example 1, 1,4-dimethyl-5-(3-trifluoromethyl-phenyl)-1H-pyrazole-3-carboxylic acid and 4-pyrrolidine-1-yl-piperidine with HATU/$iPr_2Net$ gave the title compound as yellow oil. MS: 421.1 ($MH^+$).

Example 160

[5-Methyl-3-pyridin-4-yl-1-(3-trifluoromethoxy-phenyl)-1H-pyrazol-4-yl]-(4-pyrrolidin-1-yl-piperidin-1-yl)-methanone

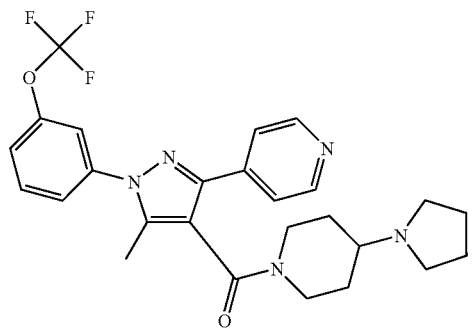

A] 3-Oxo-2-(pyridine-4-carbonyl)-butyric acid ethyl ester 8 g (61.5 mmol) of ethyl acetoacetate were dissolved in 280 ml of $CH_2Cl_2$, the solution was cooled at 0° C. and successively were added 6.00 g (63.3 mmol) of anhydrous magnesium chloride, 10 ml (124 mmol) of pyridine and 13.4 g (94.73 mmol) of isonicotinoyl chloride. The yellow suspension was stirred 1 h under ice cooling and 18 h at room temperature. The reaction mixture was poured into crashed ice and extracted twice with $CH_2Cl_2$. The organic phases were washed with brine, dried over magnesium sulfate, and evaporated. The residue was purified by column chromatography (n-heptane:EtOAc 1:4) to afford the title compound as light yellow oil (6.75 g, 47%). MS: 236.0 ($MH^+$).

B] 5-Methyl-3-pyridin-4-yl-1H-pyrazole-4-carboxylic acid ethyl ester

To a solution of 3-oxo-2-(pyridine-4-carbonyl)-butyric acid ethyl ester (1 g, 4.25 mmol) in 10 ml ethanol, were added a solution of hydrazine hydrochloride (291 mg, 4.25 mmol) in 4 ml water and, then 0.1 ml of 4M HCl in dioxane. The yellow solution was stirred 1 h at room temperature, poured on a saturated solution of $NaHCO_3$ and extracted twice with EtOAc. The organic phases were washed with brine, dried over magnesium sulfate, and evaporated to afford the title compound as light yellow solid (815 mg, 83%). MS: 232.1 ($MH^+$).

C] 5-Methyl-3-pyridin-4-yl-1-(3-trifluoromethoxy-phenyl)-1H-pyrazole-4-carboxylic acid ethyl ester A blue-green suspension of 5-methyl-3-pyridin-4-yl-1H-pyrazole-4-carboxylic acid ethyl ester (700 mg, 3.03 mmol), molecular sieves 4A, 3-(trifluoromethoxy)benzeneboronic acid (1.25 g, 6.05 mmol), copper (II) acetate (824 mg, 4.54 mmol) and pyridine (0.48 ml, 6.05 mmol) in 14 ml $CH_2Cl_2$ was stirred under argon atmosphere and at room temperature for 5 days. The reaction mixture was diluted with $CH_2Cl_2$ and washed with a saturated solution of $NaHCO_3$ and brine. The aqueous phases were extracted twice with $CH_2Cl_2$, the combined organic layers dried over magnesium sulfate, and evaporated. The residue was treated with EtOAc:toluene, 1:9, filtered off. The filtrate was evaporated and chromatographed twice (amino-phase silica gel, toluene:EtOAc 9:1) to afford the title compound as a colorless oil (638 mg, 54%). MS: 392.1 ($MH^+$).

D] 5-Methyl-3-pyridin-4-yl-1-(3-trifluoromethoxy-phenyl)-1H-pyrazole-4-carboxylic acid To a solution of 5-methyl-3-pyridin-4-yl-1-(3-trifluoromethoxy-phenyl)-1H-pyrazole-4-carboxylic acid ethyl ester (605 mg, 1.55 mmol) in 5 ml THF, 2.5 ml methanol and 2.5 ml water, was added lithium hydroxide monohydrate (111 mg, 4.63 mmol). The solution was heated at 80° C. for 2 h. The reaction mixture was cooled, diluted with EtOAc and washed twice with 10% $KHSO_4$ and brine. The aqueous phases were extracted with EtOAc and with three portions of $CH_2Cl_2$. The combined organic layers were dried over magnesium sulfate, and evaporated. The residue was precipitated from tBuOMe to give a white solid (436 mg, 76%) of the title compound. MS: 364.1 ($MH^+$).

E] [5-Methyl-3-pyridin-4-yl-1-(3-trifluoromethoxy-phenyl)-1H-pyrazol-4-yl]-(4-pyrrolidin-1-yl-piperidin-1-yl)-methanone 5-Methyl-3-pyridin-4-yl-1-(3-trifluoromethoxy-phenyl)-1H-pyrazole-4-carboxylic acid (76 mg, 0.21 mmol) in 2.5 ml DMF was treated with $iPr_2NEt$ (0.11 ml, 0.63 mmol) and

Example 161

[4-((S)-2-Hydroxymethyl-pyrrolidin-1-yl)-piperidin-1-yl]-[5-methyl-3-pyridin-4-yl-1-(3-trifluoromethoxy-phenyl)-1H-pyrazol-4-yl]-methanone

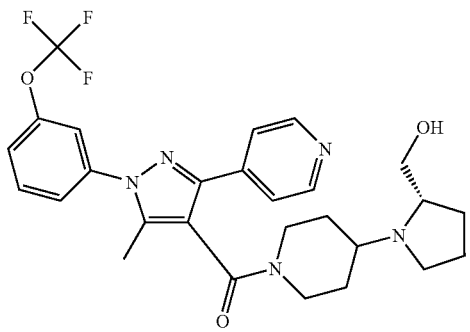

A) ((S)-1-Piperidin-4-yl-pyrrolidin-2-yl)-methanol di-hydrochloride

To a solution of 4-oxo-piperidine-1-carboxylic acid tert-butyl ester (1.0 g, 5 mmol), S)-1-pyrrolidin-2-yl-methanol (0.6 g, 6 mmol), acetic acid (0.3 ml, 6 mmol) in CH$_2$Cl$_2$ (10 ml) was added sodium triacetoxyborohydride (1.2 g, 6 mmol). The reaction was stirred for 1 h after which time it was washed with saturated sodium hydrogen carbonate, dried with sodium sulphate and concentrated. The residue (1.1 g, 4 mmol) was redissolved in 4M hydrochloric acid in dioxane (6 ml) and stirred for 1 h. Concentration afforded the title compound (1.0 g, quant) as a light orange foam. MS: 185.1 (MH$^+$).

B] [4-((S)-2-Hydroxymethyl-pyrrolidin-1-yl)-piperidin-1-yl]-[5-methyl-3-pyridin-4-yl-1-(3-trifluoromethoxy-phenyl)-1H-pyrazol-4-yl]-methanone In analogy to the procedure described in Example 160E], 5-methyl-3-pyridin-4-yl-1-(3-trifluoromethoxy-phenyl)-1H-pyrazole-4-carboxylic acid (Example 160D]) and ((S)-1-piperidin-4-yl-pyrrolidin-2-yl)-methanol dihydrochloride gave the title compound in 78% yield as a light yellow foam. MS: 530.0 (MH$^+$).

Example 162

[5-Cyclopropyl-3-pyridin-4-yl-1-(3-trifluoromethoxy-phenyl)-1H-pyrazol-4-yl]-(4-pyrrolidin-1-yl-piperidin-1-yl)-methanone

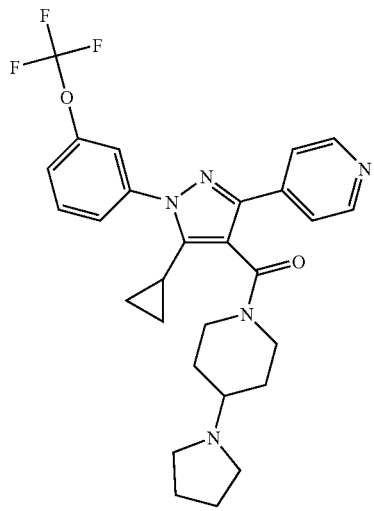

A] 3-Cyclopropyl-3-oxo-2-(pyridine-4-carbonyl)-propionic acid ethyl ester 7.5 g (48 mmol) of 3-cyclopropyl-3-oxo-propionic acid ethyl ester were dissolved in 250 ml of CH$_2$Cl$_2$, the solution was cooled at 0° C. and successively were added 4.71 g (49.5 mmol) of anhydrous magnesium chloride, 8.1 ml (100 mmol) of pyridine and 12.8 g (72 mmol) of isonicotinoyl chloride-.hydrochloride. The yellow suspension was stirred 1 h under ice cooling and 18 h at room temperature. The reaction mixture was poured into crashed ice and extracted twice with CH$_2$Cl$_2$. The organic phases were washed with brine, dried over magnesium sulfate, and evaporated. The residual product was purified by column chromatography (n-heptane:EtOAc 1:1) to afford the title compound as light yellow oil (10 g, 79%). MS: 262.1 (MH$^+$).

B] 5-Cyclopropyl-3-pyridin-4-yl-1H-pyrazole-4-carboxylic acid ethyl ester 220 mg (0.84 mmol) of 3-cyclopropyl-3-oxo-2-(pyridine-4-carbonyl)-propionic acid ethyl ester and 57 mg (0.84 mmol) hydrazine.hydrochloride were dissolved in 3 ml ethanol, 1.5 ml water and 0.2 ml 4M HCl dioxane. The yellow solution was stirred 1 h at room temperature. The reaction mixture was evaporated, the residue taken in EtOAc and washed with brine, the aqueous layers were extracted with EtOAc. The combined organic phases were dried over magnesium sulfate and evaporated. The title compound was received as yellow gum (148 mg, 68%). MS: 258.0 (MH$^+$).

C] 5-Cyclopropyl-3-pyridin-4-yl-1-(3-trifluoromethoxy-phenyl)-1H-pyrazole-4-carboxylic acid ethyl ester In analogy to the procedure described in Example 160C], 5-cyclopropyl-3-pyridin-4-yl-1H-pyrazole-4-carboxylic acid ethyl ester and 3-(trifluoromethoxy)benzeneboronic acid gave the title compound as a colorless oil (23%). MS: 418.3 (MH$^+$).

D] 5-Cyclopropyl-3-pyridin-4-yl-1-(3-trifluoromethoxy-phenyl)-1H-pyrazole-4-carboxylic acid To a solution of 5-cyclopropyl-3-pyridin-4-yl-1-(3-trifluoromethoxy-phenyl)-1H-pyrazole-4-carboxylic acid ethyl ester (154 mg, 0.37 mmol) in 2 ml THF, 1 ml methanol and 1 ml water, was added lithium hydroxide monohydrate (26 mg, 1.11 mmol). The solution was heated at 80° C. for 2 h. The reaction mixture was cooled, diluted with CH$_2$Cl$_2$ and washed with water. The aqueous phases were extracted with three portions of CH$_2$Cl$_2$. The combined organic layers were dried over magnesium sulfate, and evaporated to deliver a white solid (128 mg, 89%) of the tide compound. MS: 388.2 (M–H$^-$).

E] [5-Cyclopropyl-3-pyridin-4-yl-1-(3-trifluoromethoxy-phenyl)-1H-pyrazol-4-yl]-(4-pyrrolidin-1-yl-piperidin-1-yl)-methanone In analogy to the procedure described in Example 160E], 5-cyclopropyl-3-pyridin-4-yl-1-(3-trifluoromethoxy-phenyl)-1H-pyrazole-4-carboxylic acid and 4-(1-pyrrolidinyl)piperidine gave the title compound as a light yellow gum (91%). MS: 526.0 (MH$^+$).

Example 163

[5-Cyclopropyl-3-pyridin-4-yl-1-(3-trifluoromethoxy-phenyl)-1H-pyrazol-4-yl]-[4-((S)-2-hydroxymethyl-pyrrolidin-1-yl)-piperidin-1-yl]-methanone

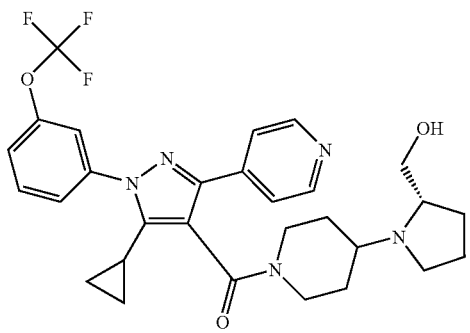

In analogy to the procedure described in Example 160E, 5-cyclopropyl-3-pyridin-4-yl-1-(3-trifluoromethoxy-phenyl)-1H-pyrazole-4-carboxylic acid (Example 162D]) and ((S)-1-piperidin-4-yl-pyrrolidin-2-yl)-methanol dihydrochloride (Example 161A]) gave the title compound as a light brown oil (56%). MS: 556.2 (MH$^+$).

Example 164

[5-Cyclopropyl-3-pyridin-3-yl-1-(3-trifluoromethyl-phenyl)-1H-pyrazol-4-yl]-(4-pyrrolidin-1-yl-piperidin-1-yl)-methanone

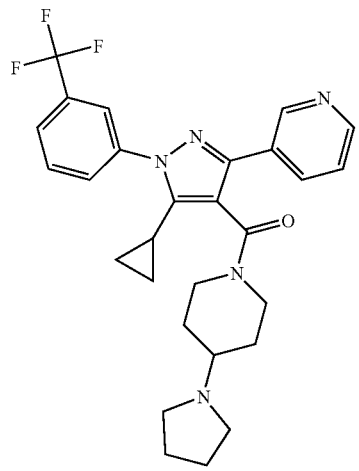

A] 3-cyclopropyl-3-oxo-2-(pyridine-3-carbonyl)-propionic acid methyl ester

In analogy to the procedure described in Example 160A], 3-cyclopropyl-3-oxo-propionic acid methyl ester and 3-pyridinecarboxylique acid chloride hydrochloride gave 3-cyclopropyl-3-oxo-2-(pyridine-3-carbonyl)-propionic acid methyl ester as a light yellow oil (18%).

B] 5-Cyclopropyl-3-pyridin-3-yl-1-(3-trifluoromethyl-phenyl)-1H-pyrazole-4-carboxylic acid methyl ester A solution of gave 3-cyclopropyl-3-oxo-2-(pyridine-3-carbonyl)-propionic acid methyl ester (326 mg, 1.25 mmol) and 3-(trifluoromethyl)phenylhydrazine (220 mg, 1.12 mmol) in 2 ml acetic acid was stirred 20 h at room temperature. The reaction mixture was evaporated, the residue treated with EtOAc:n-heptane 1:1 and filtered off. The filtrate was concentrated in vacuo and chromatographed (amino-phase silica gel, EtOAc:n-heptane 1:1) to yield the title compound as a light yellow gum (37 mg, 8%). MS: 388.3 (MH$^+$).

C] 5-Cyclopropyl-3-pyridin-3-yl-1-(3-trifluoromethyl-phenyl)-1H-pyrazole-4-carboxylic acid In analogy to the procedure described in Example 160D], 5-cyclopropyl-3-pyridin-3-yl-1-(3-trifluoromethyl-phenyl)-1H-pyrazole-4-carboxylic acid methyl ester gave the title compound as yellow solid (77%). MS: 374.0 (MH$^+$).

D] [5-Cyclopropyl-3-pyridin-3-yl-1-(3-trifluoromethyl-phenyl)-1H-pyrazol-4-yl]-(4-pyrrolidin-1-yl-piperidin-1-yl)-methanone In analogy to the procedure described in Example 160E], 5-cyclopropyl-3-pyridin-3-yl-1-(3-trifluoromethyl-phenyl)-

1H-pyrazole-4-carboxylic acid and 4-(1-pyrrolidinyl)piperidine gave the title compound as a light yellow solid (70%). MS: 510.4 (MH+).

Example 165

[1,4-Dimethyl-5-(3-trifluoromethyl-phenyl)-1H-pyrazol-3-yl]-(4-pyrrolidin-1-yl-piperidin-1-yl)-methanone

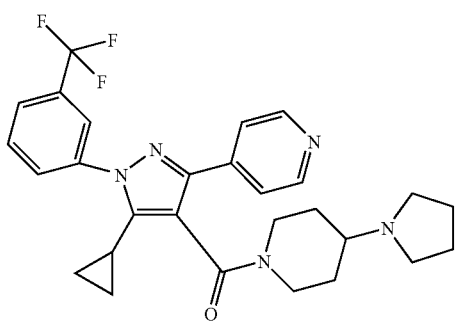

A] 5-Cyclopropyl-3-pyridin-4-yl-1-(3-trifluoromethyl-phenyl)-1H-pyrazole-4-carboxylic acid ethyl ester In analogy to the procedure described in Example 164B], 3-cyclopropyl-3-oxo-2-(pyridine-4-carbonyl)-propionic acid ethyl ester (Example 162 A]) and 3-(trifluoromethyl) phenylhydrazine gave the title compound as a white solid (12%). MS: 402.4 (MH+).

B] 5-Cyclopropyl-3-pyridin-4-yl-1-(3-trifluoromethyl-phenyl)-1H-pyrazole-4-carboxylic acid In analogy to the procedure described in Example 160D], 5-cyclopropyl-3-pyridin-4-yl-1-(3-trifluoromethyl-phenyl)-1H-pyrazole-4-carboxylic acid ethyl ester gave the title compound as a white solid (54%). MS: 374.1 (MH+).

C] [1,4-Dimethyl-5-(3-trifluoromethyl-phenyl)-1H-pyrazol-3-yl]-(4-pyrrolidin-1-yl-piperidin-1-yl)-methanone In analogy to the procedure described in Example 160E], 5-cyclopropyl-3-pyridin-4-yl-1-(3-trifluoromethyl-phenyl)-1H-pyrazole-4-carboxylic acid and 4-(1-pyrrolidinyl)piperidine gave the title compound as a light yellow solid (52%). MS: 510.5 (MH+).

Example 166

[5-Cyclopropyl-3-pyridin-4-yl-1-(3-trifluoromethyl-phenyl)-1H-pyrazol-4-yl]-[4-((S)-2-hydroxymethyl-pyrrolidin-1-yl)-piperidin-1-yl]-methanone

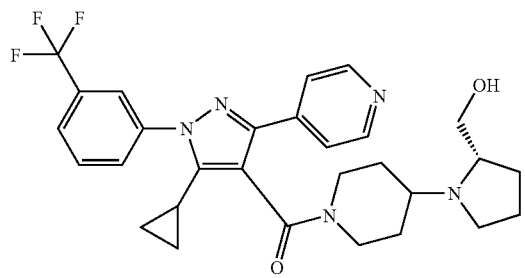

In analogy to the procedure described in Example 160E), 5-cyclopropyl-3-pyridin-4-yl-1-(3-trifluoromethyl-phenyl)-1H-pyrazole-4-carboxylic acid (Example 165B]) and ((S)-1-piperidin-4-yl-pyrrolidin-2-yl)-methanol dihydrochloride (Example 161A]) gave the title compound as a light yellow solid (54%). MS: 539.8 (MH+).

Example 167

[5-Methyl-3-pyridin-4-yl-1-(3-trifluoromethyl-phenyl)-1H-pyrazol-4-yl]-(4-pyrrolidin-1-yl-piperidin-1-yl)-methanone

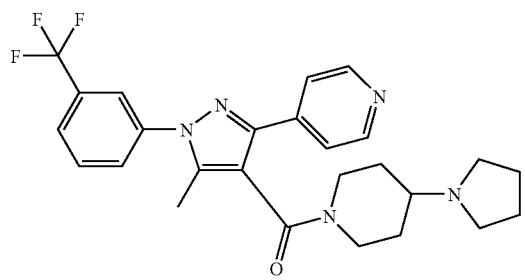

A] N-[1-Pyridin-4-yl-meth-(E)-ylidene]-N'-(3-trifluoromethyl-phenyl)-hydrazine 3-(Trifluoromethyl)phenylhydrazine (176 mg, 1 mmol) in 5 ml of acetic acid were treated with sodium acetate (164 mg, 2 mmol) and pyridine-4-carbaldehyde (0.11 ml, 1 mmol) during 1 h at 50° C. The yellow solution was cooled and ammonium hydroxide 25% was added, the solid was collected, washed with water and recrystallized from EtOAc:n-heptane. The title compound was obtained as a yellow solid (195 mg, 74%). MS: 266.1 (MH+).

B] N-[3-(Trifluoromethyl)phenyl]pyridine-4-carbohydrazonoyl bromide

Brom (0.037 ml, 0.72 mmol) was added to a solution of N-[1-pyridin-4-yl-meth-(E)-ylidene]-N'-(3-trifluoromethyl-phenyl)-hydrazine (190 mg, 0.72 mmol) in 2 ml of acetic acid. The reaction was stirred 10 min at room temperature and the orange solid was filtered. The residue was suspended in 10 ml acetone and heated under reflux for 30 min. The reaction mixture was cooled and filtered to get the title compound as a yellow solid (171 mg, 69%). MS: 343.0 (1 Br, MH⁺).

C] 5-Methyl-3-pyridin-4-yl-1-(3-trifluoromethyl-phenyl)-1H-pyrazole-4-carboxylic acid ethyl ester An ice cooled solution of ethyl acetoacetate (0.21 ml, 1.63 mmol) in 10 ml ethanol was treated with a solution of sodium ethanolate 21% (in ethanol, 0.6 ml, 1.63 mmol). The reaction mixture was stirred 1 h at 0° C., then N-[3-(trifluoromethyl)phenyl]pyridine-4-carbohydrazonoyl bromide (562 mg, 1.63 mmol) in 5 ml ethanol was added drop wise. The yellow suspension was stirred 1 h at room temperature and 2 days at 50° C. The reaction mixture was concentrated in vacuo and the residual product partitioned between EtOAc and water. The aqueous layer was extracted with EtOAc. The organic phases were dried over magnesium sulfate and evaporated. Column chromatography (EtOAc:n-heptane 1:1) gave the title compound as a light brown oil (130 mg, 21%). MS: 376.5 (MH⁺).

D] 5-Methyl-3-pyridin-4-yl-1-(3-trifluoromethyl-phenyl)-1H-pyrazole-4-carboxylic acid In analogy to the procedure described in Example 160D], 5-methyl-3-pyridin-4-yl-1-(3-trifluoromethyl-phenyl)-1H-pyrazole-4-carboxylic acid ethyl ester gave the title compound as a white solid (75%). MS: 348.1 (MH⁺).

E) [5-Methyl-3-pyridin-4-yl-1-(3-trifluoromethyl-phenyl)-1H-pyrazol-4-yl]-(4-pyrrolidin-1-yl-piperidin-1-yl)-methanone In analogy to the procedure described in Example 160E], 5-methyl-3-pyridin-4-yl-1-(3-trifluoromethyl-phenyl)-1H-pyrazole-4-carboxylic acid and 4-(1-pyrrolidinyl)piperidine gave the title compound as a light yellow oil (12%). MS: 484.1 (MH⁺).

Example 168

[4-((S)-2-Hydroxymethyl-pyrrolidin-1-yl)-piperidin-1-yl]-[5-methyl-3-pyridin-4-yl-1-(3-trifluoromethyl-phenyl)-1H-pyrazol-4-yl]-methanone

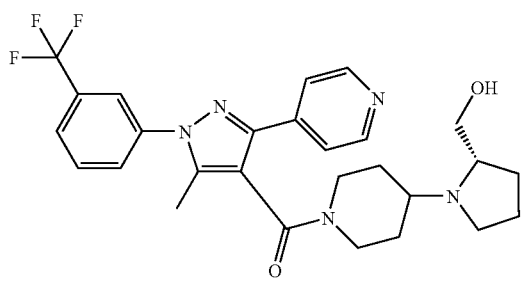

In analogy to the procedure described in Example 160E], 5-methyl-3-pyridin-4-yl-1-(3-trifluoromethyl-phenyl)-1H-pyrazole-4-carboxylic acid (Example 160D]) and ((S)-1-piperidin-4-yl-pyrrolidin-2-yl)-methanoldihydrochloride (Example 161A]) gave the title compound as a light yellow oil (14%). MS: 514.0 (MH⁺).

Example 169

[1-(4-Bromo-3-trifluoromethoxy-phenyl)-5-methyl-3-pyridin-4-yl-1H-pyrazol-4-yl]-(4-pyrrolidin-1-yl-piperidin-1-yl)-methanone

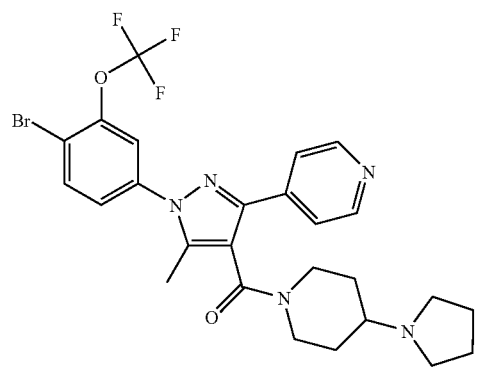

A] N-[1-Pyridin-4-yl-meth-(E)-ylidene]-N'-(3-trifluoromethoxy-phenyl)-hydrazine

In analogy to the procedure described in Example 167A], 3-(trifluoromethoxy)phenylhydrazine and pyridine-4-carbaldehyde gave the title compound as a light yellow solid (40%). MS: 282.0 (MH⁺).

B] N-[(4-Bromo-3-(trifluoromethyl))phenyl]pyridine-4-carbohydrazonoyl bromide

In analogy to the procedure described in Example 167B], 3-N-[1-pyridin-4-yl-meth-(E)-ylidene]-N'-(3-trifluoromethoxy-phenyl)-hydrazine gave the title compound as a yellow solid (63%). MS: 437.0 (2 Br, MH⁺).

C] [1-(4-Bromo-3-trifluoromethoxy-phenyl)-5-methyl-3-pyridin-4-yl-1H-1-pyrazol-4-yl]-(4-pyrrolidin-1-yl-piperidin-1-yl)-methanone In analogy to the procedure described in Example 167C] to 167E], N-[(4-bromo-3-(trifluoromethyl))phenyl]pyridine-4-carbohydrazonoyl bromide gave [1-(4-bromo-3-trifluoromethoxy-phenyl)-5-methyl-3-pyridin-4-yl-1H-pyrazol-4-yl-]-(4-pyrrolidin-1-yl-piperidin-1-yl)-methanone as a light red solid. MS: 579.6 (1 Br, MH⁺).

Example 170

[5-Methyl-3-trifluoromethyl-1-(3-trifluoromethyl-phenyl)-1H-pyrazol-4-yl]-(4-pyrrolidin-1-yl-piperidin-1-yl)-methanone

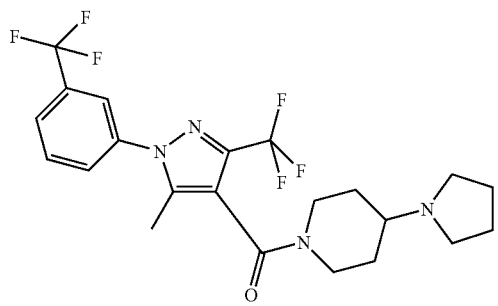

A] Trifluoro-acetic acid N'-(3-trifluoromethyl-phenyl)-hydrazide

A solution of 3-(trifluoromethyl)phenylhydrazine (500 mg, 2.84 mmol) in 10 ml THF was added drop wise (20 min) to an ice cooled solution of trifluoroacetic acid anhydride (0.4 ml, 2.84 mmol) in 5 ml THF. The reaction mixture was stirred 1 h at 0° C., 1 h at room temperature and evaporated. The residue was precipitated from n-heptane to give the title compound as a white solid (385 mg, 50%). MS: 271.2 (M−H⁻).

B] 5-Methyl-3-trifluoromethyl-1-(3-trifluoromethyl-phenyl)-1H-pyrazole-4-carboxylic acid ethyl ester A solution of trifluoro-acetic acid N'-(3-trifluoromethyl-phenyl)-hydrazide (164 mg, 0.60 mmol) and 4-toluenesulfonyl chloride (115 mg, 0.60 mmol) in 2 ml ethyl acetate was added drop wise to a solution of 4-methylmorpholine (0.067 ml, 0.60 mmol) in 1 ml of EtOAc at 0° C. The reaction of mixture was stirred 1 h at 0° C. and 2 h at room temperature, diluted with EtOAc and washed with water and brine. The combined organic layers were dried over magnesium sulfate and evaporated. The crude product of (2Z or E)-1-[3-(trifluoromethyl)phenyl]-2-(2,2,2-trifluoro-1-{[(4-methylphenyl)sulfonyl]oxy}ethylidene)hydrazine (270 mg) was taken for the next reaction without purification. MS: 425.3 (M−H⁻).

A solution of sodium ethanolate 21% (in ethanol, 0.75 ml, 2 mmol) was added to ethyl acetoacetate (0.25 ml, 1.97 mmol) in 3 ml ethanol at 0° C. After 1 h at 0° C., a solution of (2Z or E)-1-[3-(trifluoromethyl)phenyl]-2-(2,2,2-trifluoro-1-{[(4-methylphenyl)sulfonyl]-oxy}ethylidene)hydrazine (254 mg, 0.60 mmol) in 5 ml ethanol was added. Stirring was continued for 18 h at room temperature and then the yellow solution was diluted with EtOAc washed with water and brine. The combined organic layers were dried over magnesium sulfate and evaporated. Column chromatography (EtOAc:n-heptane 1:3) delivered the title compound as light yellow solid (107 mg, 48%). MS: 367.3 (MH⁺).

C] 5-Methyl-3-trifluoromethyl-1-(3-trifluoromethyl-phenyl)-1H-pyrazole-4-carboxylic acid In analogy to the procedure described in Example 160D], 5-methyl-3-trifluoromethyl-1-(3-trifluoromethyl-phenyl)-1H-pyrazole-4-carboxylic acid ethyl ester gave the title compound as a yellow oil (90%). MS: 337.3 (M−H⁻).

D] [5-Methyl-3-trifluoromethyl-1-(3-trifluoromethyl-phenyl)-1H-pyrazol-4-yl]-(4-pyrrolidin-1-yl-piperidin-1-yl)-methanone In analogy to the procedure described in Example 160E), 5-methyl-3-trifluoromethyl-1-(3-trifluoromethyl-phenyl)-1H-pyrazole-4-carboxylic acid and 4-(1-pyrrolidinyl)piperidine gave the title compound as a yellow foam (88%). MS: 475.2 (MH⁺).

Example 171

N-[5-Cyclopropyl-4-(4-pyrrolidin-1-yl-piperidine-1-carbonyl)-1-(3trifluoromethoxy-phenyl)-1H-pyrazol-3-ylmethyl]-acetamide

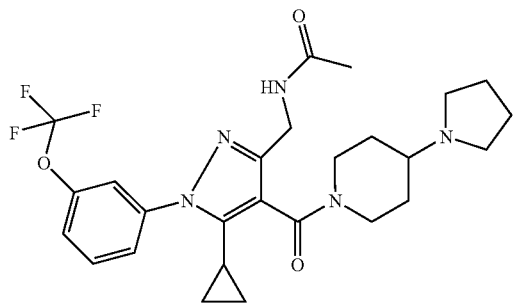

A] 2-Cyclopropanecarbonyl-4-(1,3-dioxo-1,3-dihydro-isoindol-2-yl)-3-oxo-butyric acid ethyl ester In analogy to the procedure described in Example 160A], 3-cyclopropyl-3-oxo-propionic acid ethyl ester and (1,3-dioxo-1,3-dihydro-isoindol-2-yl)-acetyl chloride gave the title compound as a white solid (60%). MS: 342.1 (M−H⁻).

B] 5-Cyclopropyl-3-(1,3-dioxo-1,3-dihydro-isoindol-2-ylmethyl)-1H-pyrazole-4-carboxylic acid ethyl ester In analogy to the procedure described in Example 160B]), 2-cyclopropanecarbonyl-4-(1,3-dioxo-1,3-dihydro-isoindol-2-yl)-3-oxo-butyric acid ethyl ester and hydrazine.hydrochloride gave the title compound as a light yellow solid (36%). MS: 338.5 (M−H⁻).

C] 5-Cyclopropyl-3-(1,3-dioxo-1,3-dihydro-isoindol-2-ylmethyl)-1-(3-trifluoromethoxy-phenyl)-1H-pyrazole-4-carboxylic acid ethyl ester In analogy to the procedure described in Example 160C], 5-cyclopropyl-3-(1,3-dioxo-1,3-dihydro-isoindol-2-ylmethyl)-1H-pyrazole-4-carboxylic acid ethyl ester and 3-(trifluoromethoxy)benzeneboronic acid gave the title compound as a white solid (54%). MS: 500.0 (MH⁺).

D] 3-Aminomethyl-5-cyclopropyl-1-(3-trifluoromethoxy-phenyl)-1H-pyrazole-4-carboxylic acid ethyl ester 5-Cyclopropyl-3-(1,3-dioxo-1,3-dihydro-isoindol-2-ylmethyl)-1-(3-trifluoromethoxy-phenyl)-1H-pyrazole-4-carboxylic acid ethyl aster (330 mg, 0.66 mmol) and 1 ml (20 mmol) hydrazine monohydrate in 20 ml ethanol and 20 ml was stirred 20 h at room temperature. The white precipitate was filtered off. The filtrate was concentrated in vacuo, the residue partitioned between CH$_2$Cl$_2$ and water. The aqueous phase was extracted with CH$_2$Cl$_2$. The organic layers were dried over magnesium sulfate and evaporated to give the title compound as colorless oil (230 mg, 94%). MS: 370.1 (MH$^+$).

E] 3-(Acetylamino-methyl)-5-cyclopropyl-1-(3-trifluoromethoxy-phenyl)-1H-pyrazole-4-carboxylic acid ethyl ester A solution of 3-aminomethyl-5-cyclopropyl-1-(3-trifluoromethoxy-phenyl)-1H-pyrazole-4-carboxylic acid ethyl ester (46 mg, 0.12 mmol) and iPr$_2$NEt (0.06 ml, 0.37 mmol) in 0.5 ml THF under ice cooling was treated with acetylchloride (0.011 ml, 0.15 mmol). The yellow suspension was stirred 2 h at 0° C., then diluted with EtOAc and washed with water and brine. The aqueous phases were extracted with EtOAc. The organic layers were dried over magnesium sulfate, evaporated and chromatographed (amino-phase silica gel, EtOAc) to give the title compound as a yellow oil (37 mg, 72%). MS: 412.3 (MH$^+$).

F] N-[5-Cyclopropyl-4-(4-pyrrolidin-1-yl-piperidine-1-carbonyl)-1-(3-trifluoromethoxy-phenyl)-1H-pyrazol-3-yl-methyl]-acetamide In analogy to the procedure described in Example 160D] and 160E], 3-(acetylamino-methyl)-5-cyclopropyl-1-(3-trifluoromethoxy-phenyl)-1H-pyrazole-4-carboxylic acid ethyl ester gave in two steps, the title compound as a white foam (29%). MS: 520.2 (MH$^+$).

Example 172

[5-Methyl-3-pyrimidin-5-yl-1-(3-trifluoromethoxy-phenyl)-1H-pyrazol-4-yl]-(4-pyrrolidin-1-yl-piperidin-1-yl)-methanone

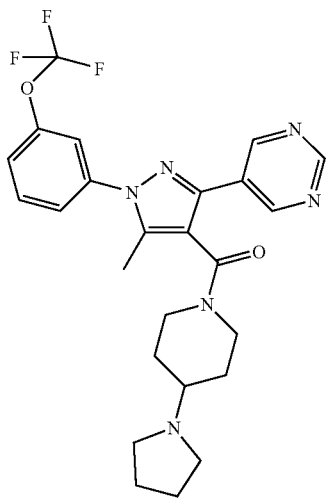

A] N-[1-Pyrimidin-5-yl-meth-(E)-ylidene]-N'-(3-trifluoromethoxy-phenyl)-hydrazine In analogy to the procedure described in Example 167A], pyrimidine-5-carbaldehyde and (3-trifluoromethoxy-phenyl)-hydrazine gave the title compound as an orange solid (12%). MS: 281.5 (M–H$^-$).

B] 5-Methyl-3-pyrimidin-5-yl-1-(3-trifluoromethoxy-phenyl)-1H-pyrazole-4-carboxylic acid ethyl ester A mixture of N-[1-pyrimidin-5-yl-meth-(E)-ylidene]-N'-(3-trifluoromethoxy-phenyl)-hydrazine (215 mg, 0.76 mmol) and zinc chloride (208 mg, 1.52 mmol) in 2 ml ethyl acetoacetate was heated at 170° C. for 3 h and stirring was continued for 20 h at room temperature. Ethyl acetoacetate was distilled (Kugelrohr distillation, 90° C., 10-40 mbar) and the residue was purified by column chromatography (EtOAc:n-heptane 4:1) to afford the title compound as a yellow oil (89 mg, 30%). MS: 393.0 (MH$^+$).

C] 5-Methyl-3-pyrimidin-5-yl-1-(3-trifluoromethoxy-phenyl)-1H-pyrazole-4-carboxylic acid In analogy to the procedure described in Example 162D], 5-methyl-3-pyrimidin-5-yl-1-(3-trifluoromethoxy-phenyl)-1H-pyrazole-4-carboxylic acid ethyl ester gave the title compound as a light yellow solid (81%). MS: 363.3 (M–H$^-$).

D] [5-Methyl-3-pyrimidin-5-yl-1-(3-trifluoromethoxy-phenyl)-1H-pyrazol-4-yl]-(4-pyrrolidin-1-yl-piperidin-1-yl)-methanone In analogy to the procedure described in Example 160E], 5-methyl-3-pyrimidin-5-yl-1-(3-trifluoromethoxy-phenyl)-1H-pyrazole-4-carboxylic acid and 4-(1-pyrrolidinyl)piperidine gave the title compound as a yellow oil (32%). MS: 501.0 (MH$^+$).

Example 173

[5-Methyl-3-pyrimidin-5-yl-1-(3-trifluoromethyl-phenyl)-1H-pyrazol-4-yl]-(4-pyrrolidin-1-yl-piperidin-1-yl)-methanone

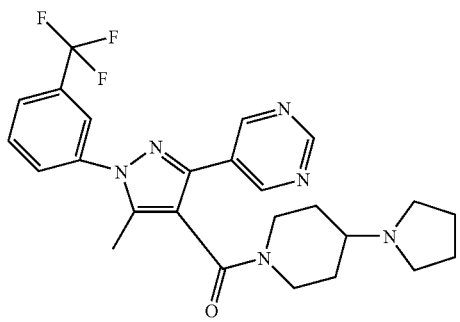

A] 1N-[1-Pyrimidin-5-yl-meth-(E)-ylidene]-N'-(3-trifluoromethyl-phenyl)-hydrazine In analogy to the procedure described in Example 167A], 3-(trifluoromethyl)phenylhydrazine and pyrimidine-5-carbaldehyde gave the title compound as a yellow solid (87%). MS: 267.1 (MH$^+$).

B] N-[3-(Trifluoromethyl)phenyl]-pyrimidine-5-carbohydrazonoyl bromide and N-[(4-bromo-3-(trifluoromethyl))phenyl]-pyrimidine-5-carbohydrazonoyl bromide In analogy to the procedure described in Example 167B], N-[1-pyrimidin-5-yl-meth-(E)-ylidene]-N'-(3-trifluoromethyl-phenyl)-hydrazine gave a 1:3 mixture of N-[3-(trifluoromethyl)phenyl]-pyrimidine-5-carbohydrazonoyl bromide and N-[(4-bromo-3-(trifluoromethyl))phenyl]-pyrimidine-5-carbohydrazonoyl bromide as an orange solid (73%). MS: 344 (1 Br, MH$^+$) and 422 (2 Br, MH$^+$).

C] 5-Methyl-3-pyrimidin-5-yl-1-(3-trifluoromethyl-phenyl)-1H-pyrazole-4-carboxylic acid ethyl ester and 1-(4-Bromo-3-trifluoromethyl-phenyl)-5-methyl-3-pyrimidin-5-yl-1H-pyrazole-4-carboxylic acid ethyl ester In analogy to the procedure described in Example 167C], N-[3-(trifluoromethyl)phenyl]-pyrimidine-5-carbohydrazonoyl bromide and N-[(4-bromo-3-(trifluoromethyl))phenyl]-pyrimidine-5-carbohydrazonoyl bromide gave, after a column chromatography (EtOAc:n-heptane 1:1), a 1:1 mixture of 5-methyl-3-pyrimidin-5-yl-1-(3-trifluoromethyl-phenyl)-1H-pyrazole-4-carboxylic acid ethyl ester and 1-(4-bromo-3-trifluoromethyl-phenyl)-5-methyl-3-pyrimidin-5-yl-1H-pyrazole-4-carboxylic acid ethyl ester as a yellow solid (58%). MS: 376 (MH$^+$) and 454 (1 Br, MH$^+$).

D] 5-Methyl-3-pyrimidin-5-yl-1-(3-trifluoromethyl-phenyl)-1H-pyrazole-4-carboxylic acid and 1-(4-Bromo-3-trifluoromethyl-phenyl)-5-methyl-3-pyrimidin-5-yl-1H-pyrazole-4-carboxylic acid In analogy to the procedure described in Example 160D], a mixture of 5-methyl-3-pyrimidin-5-yl-1-(3-trifluoromethyl-phenyl)-1H-pyrazole-4-carboxylic acid ethyl ester and 1-(4-bromo-3-trifluoromethyl-phenyl)-5-methyl-3-pyrimidin-5-yl-1H-pyrazole-4-carboxylic acid ethyl ester gave the title compounds. MS: 349.1 (MH$^+$) and 429.1 (1 Br, MH$^+$).

E] [5-Methyl-3-pyrimidin-5-yl-1-(3-trifluoromethyl-phenyl)-1H-pyrazol-4-yl]-(4-pyrrolidin-1-yl-piperidin-1-yl)-methanone and [1-(4-Bromo-3-trifluoromethyl-phenyl)-5-methyl-3-pyrimidin-5-yl-1H-pyrazol-4-yl]-(4-pyrrolidin-1-yl-piperidin-1-yl)-methanone In analogy to the procedure described in Example 160E], a mixture of 5-methyl-3-pyrimidin-5-yl-1-(3-trifluoromethyl-phenyl)-1H-pyrazole-4-carboxylic acid and 1-(4-bromo-3-trifluoromethyl-phenyl)-5-methyl-3-pyrimidin-5-yl-1H-pyrazole-4-carboxylic acid and 4-(1-pyrrolidinyl)piperidine gave a mixture of the title compounds. Purification by reversed phase HPLC (MeCN:H$_2$O) afforded [1-(4-bromo-3-trifluoromethyl-phenyl)-5-methyl-3-pyrimidin-5-yl-1H-pyrazol-4-yl]-(4-pyrrolidin-1-yl-piperidin-1-yl)-methanone (Example 174) and [5-methyl-3-pyrimidin-5-yl-1-(3-trifluoromethyl-phenyl)-1H-pyrazol-4-yl]-(4-pyrrolidin-1-yl-piperidin-1-yl)-methanone as a white solid (20%). MS: 485.4 (MH$^+$).

Example 174

[1-(4-Bromo-3-trifluoromethyl-phenyl)-5-methyl-3-pyrimidin-5-yl-1H-pyrazol-4-yl]-(4-pyrrolidin-1-yl-piperidin-1-yl)-methanone

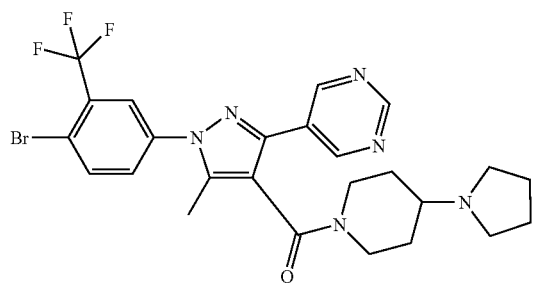

In analogy to the procedure described in Example 160E], 5-methyl-3-pyrimidin-5-yl-1-(3-trifluoromethyl-phenyl)-1H-pyrazole-4-carboxylic acid and 1-(4-bromo-3-trifluoromethyl-phenyl)-5-methyl-3-pyrimidin-5-yl-1H-pyrazole-4-carboxylic acid (example 173D]) gave a mixture of the title compound and example 173E]. Purification by reversed phase HPLC (MeCN:H$_2$O) afforded [5-methyl-3-pyrimidin-5-yl-1-(3-trifluoromethyl-phenyl)-1H-pyrazol-4-yl]-(4-pyrrolidin-1-yl-piperidin-1-yl)-methanone (Example 173E]) and [1-(4-bromo-3-trifluoromethyl-phenyl)-5-methyl-3-pyrimidin-5-yl-1H-pyrazol-4-yl]-(4-pyrrolidin-1-yl-piperidin-1-yl)-methanone and as a white solid (25%). MS: 563.2 (1 Br, MH$^+$).

Example 175

[4-((S)-2-Hydroxymethyl-pyrrolidin-1-yl)-piperidin-1-yl]-[5-methyl-3-pyrimidin-5-yl-1-(3-trifluoromethyl-phenyl)-1H-pyrazol-4-yl]-methanone

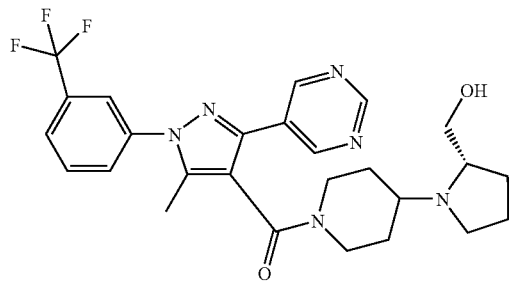

In analogy to the procedure described in Example 160E], a mixture of 5-methyl-3-pyrimidin-5-yl-1-(3-trifluoromethyl-phenyl)-1H-pyrazole-4-carboxylic acid and 1-(4-bromo-3-trifluoromethyl-phenyl)-5-methyl-3-pyrimidin-5-yl-1H-pyrazole-4-carboxylic acid (example 173D]) and ((S)-1-piperidin-4-yl-pyrrolidin-2-yl)-methanoldihydrochloride (Example 161A]) gave a mixture of the title compound and example 176. Purification by reversed phase HPLC (MeCN:H$_2$O) afforded [1-(4-bromo-3-trifluoromethyl-phenyl)-5-methyl-3-pyrimidin-5-yl-1H-pyrazol-4-yl]-[4-((S)-2-hydroxymethyl-pyrrolidin-1-yl)-piperidin-1-yl]-methanone (Example 176) and [4-((S)-2-hydroxymethyl-pyrrolidin-1-yl)-piperidin-1-yl]-[5-methyl-3-pyrimidin-5-yl-1-(3-trifluoromethyl-phenyl)-1H-pyrazol-4-yl]-methanone as a white solid (32%). MS: 515.5 (MH⁺).

Example 176

[1-(4-Bromo-3-trifluoromethyl-phenyl)-5-methyl-3-pyrimidin-5-yl-1H-pyrazol-4-yl]-[4-((S)-2-hydroxymethyl-pyrrolidin-1-yl)-piperidin-1-yl]-methanone

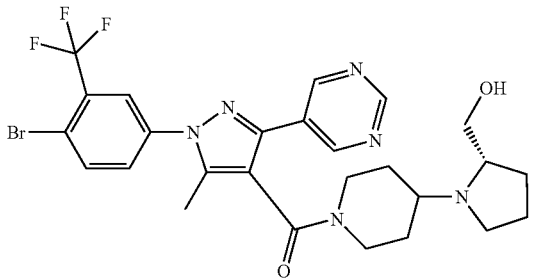

In analogy to the procedure described in Example 160E], a mixture of 5-methyl-3-pyrimidin-5-yl-1-(3-trifluoromethyl-phenyl)-1H-pyrazole-4-carboxylic acid and 1-(4-bromo-3-trifluoromethyl-phenyl)-5-methyl-3-pyrimidin-5-yl-1H-pyrazole-4-carboxylic acid (example 173D]) and ((S)-1-piperidin-4-yl-pyrrolidin-2-yl)-methanoldihydrochloride (Example 161A]) gave a mixture of the title compound and example 175. Purification by reversed phase HPLC (MeCN: H₂O) afforded [4-((S)-2-hydroxymethyl-pyrrolidin-1-yl)-piperidin-1-yl]-[5-methyl-3-pyrimidin-5-yl-1-(3-trifluoromethyl-phenyl)-1H-pyrazol-4-yl]-methanone (Example 175) and [1-(4-bromo-3-trifluoromethyl-phenyl)-5-methyl-3-pyrimidin-5-yl-1H-pyrazol-4-yl]-[4-((S)-2-hydroxymethyl-pyrrolidin-1-yl)-piperidin-1-yl]-methanone) as a white solid (31%). MS: 593.4 (1 Br, MH⁺).

Example 177

[5-Cyclopropyl-3-pyrimidin-5-yl-1-(3-trifluoromethyl-phenyl)-1H-pyrazol-4-yl]-(4-pyrrolidin-1-yl-piperidin-1-yl)-methanone

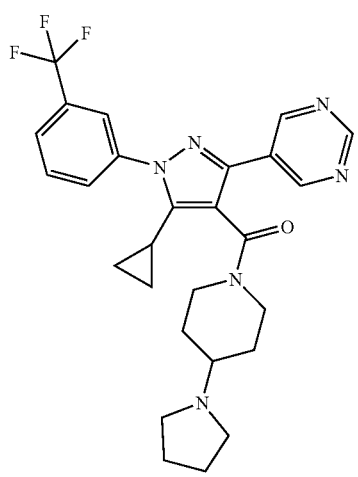

A] 2-Cyclopropanecarbonyl-3-oxo-3-pyrimidin-5-yl-propionic acid ethyl ester

In analogy to the procedure described in Example 162A], 3-cyclopropyl-3-oxo-propionic acid ethyl ester and pyrimidine-5-carbonyl chloride gave the title compound as a yellow oil (40%). MS: 261.3 (M−H⁻).

B] 5-Cyclopropyl-3-pyrimidin-5-yl-1H-pyrazole-4-carboxylic acid ethyl ester

In analogy to the procedure described in Example 162B], 2-cyclopropanecarbonyl-3-oxo-3-pyrimidin-5-yl-propionic acid ethyl ester and hydrazine.hydrochloride gave the title compound as white solid (39%). MS: 259.1 (MH⁺).

C] 5-Cyclopropyl-3-pyrimidin-5-yl-1-(3-trifluoromethyl-phenyl)-1H-pyrazole-4-carboxylic acid ethyl ester In analogy to the procedure described in Example 162C], 5-cyclopropyl-3-pyrimidin-5-yl-1H-pyrazole-4-carboxylic acid ethyl ester and 3-(trifluoromethyl)benzeneboronic acid gave the title compound as a yellow oil (34%). MS: 403.2 (MH⁺).

D] [5-Cyclopropyl-3-pyrimidin-5-yl-1-(3-trifluoromethyl-phenyl)-1H-pyrazol-4-yl]-(4-pyrrolidin-1-yl-piperidin-1-yl)-methanone Following the sequence described in Example 162D] to 162E], 5-cyclopropyl-3-pyrimidin-5-yl-1-(3-trifluoromethyl-phenyl)-1H-pyrazole-4-carboxylic acid ethyl ester gave the title compound as a white solid (38%). MS: 511.3 (MH⁺).

Example 178

[5-Cyclopropyl-3-pyrimidin-5-yl-1-(3-trifluoromethoxy-phenyl)-1H-pyrazol-4-yl]-(4-pyrrolidin-1-yl-piperidin-1-yl)-methanone

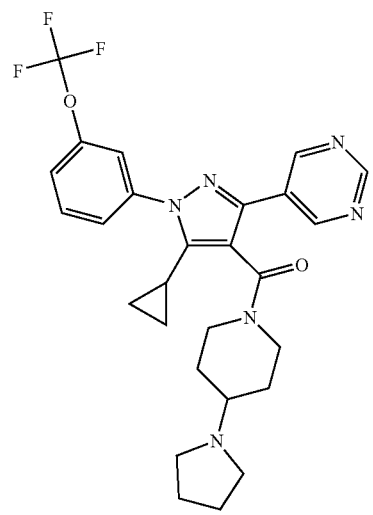

A] 5-Cyclopropyl-3-pyrimidin-5-yl-1-(3-trifluoromethoxy-phenyl)-1H-pyrazole-4-carboxylic acid ethyl ester In analogy to the procedure described in Example 162C], 5-cyclopropyl-3-pyrimidin-5-yl-1H-pyrazole-4-carboxylic acid ethyl ester (Example 177B]) and 3-(trifluoromethoxy) benzeneboronic acid gave the title compound as a yellow oil (31%). MS: 419.0 (MH⁺).

B] [5-Cyclopropyl-3-pyrimidin-5-yl-1-(3-trifluoromethoxy-phenyl)-1H-pyrazol-4-yl]-(4-pyrrolidin-1-yl-piperidin-1-yl)-methanone Following the sequence described in Example 162D] to 162E], 5-cyclopropyl-3-pyrimidin-5-yl-1-(3-trifluoromethoxy-phenyl)-1H-pyrazole-4-carboxylic acid ethyl ester gave the title compound as a white solid (58%). MS: 527.2 (MH⁺).

Example 179

[5-Cyclopropyl-3-pyrimidin-5-yl-1-(4-trifluoromethoxy-phenyl)-1H-pyrazol-4-yl]-(4-pyrrolidin-1-yl-piperidin-1-yl)-methanone

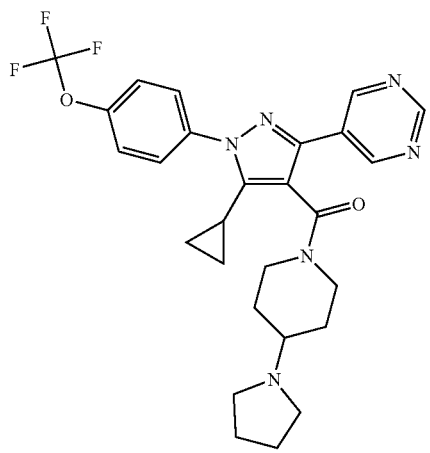

A] 5-Cyclopropyl-3-pyrimidin-5-yl-1-(4-trifluoromethoxy-phenyl)-1H-pyrazole-4-carboxylic acid ethyl ester In analogy to the procedure described in Example 162C], 5-cyclopropyl-3-pyrimidin-5-yl-1H-pyrazole-4-carboxylic acid ethyl ester (Example 177B]) and 4-(trifluoromethoxy) benzeneboronic acid gave the title compound as a yellow oil (29%). MS: 419.0 (MH⁺).

B] [5-Cyclopropyl-3-pyrimidin-5-yl-1-(4-trifluoromethoxy-phenyl)-1H-pyrazol-4-yl]-(4-pyrrolidin-1-yl-piperidin-1-yl)-methanone Following the sequence described in Example 162D] to 162E], 5-cyclopropyl-3-pyrimidin-5-yl-1-(4-trifluoromethoxy-phenyl)-1H-pyrazole-4-carboxylic acid ethyl ester gave the title compound as a light yellow gum (11%). MS: 527.1 (MH⁺).

Example 180

5-Cyclopropyl-3-methyl-1-(3-trifluoromethoxy-phenyl)-1H-pyrazol-4-yl]-[4-((2S,3S)-3-hydroxy-2-methyl-pyrrolidin-1-yl)-piperidin-1-yl]-methanone

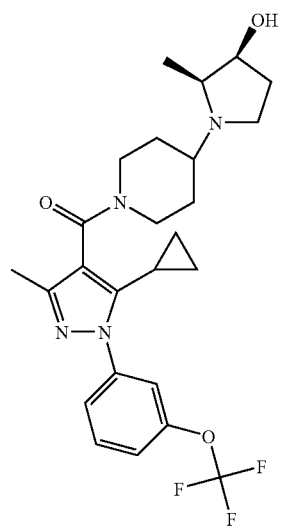

A] (2S,3R)-1-Benzyl-3-benzyloxy-2-methyl-pyrrolidine

To a cooled (0° C.) suspension of lithium aluminium hydride (2.81 g, 74 mmol) in dry THF (30 ml) was added a solution of (4R,5S)-1-benzyl-4-benzyloxy-5-methyl-pyrrolidin-2-one (3.13 g, 11 mmol) (Tetrahedron 1998, 54, 12547) in THF (20 mL). The mixture was allowed to come to room temperature and stirred for 16 h after which lime it was cooled to 0° C. and water was cautiously added. The resulting suspension was the filtered over Hyflo, washing the salts with EtOAc. The filtrate was washed with brine, dried (Na₂SO₄) and concentrated. Purification by flash column chromatography (CH₂Cl₂:MeOH 98:2-5:95) afforded the title compound (1.5 g, 50%) as a yellow oil. MS: 282.2 (MH⁺).

B] (2S,3R)-2-Methyl-pyrrolidin-3-ol hydrochloride (2S,3R)-1-Benzyl-3-benzyloxy-2-methyl-pyrrolidine (1.5 g, 5 mmol) was dissolved in MeOH (10 ml) and the pH adjusted to 1 by addition of 25% hydrochloric acid. 10% Palladium on charcoal was added (100 mg) and the mixture stirred under one atmosphere of hydrogen (balloon) for 16 h after which time it was filtered over Hyflo and concentrated to afford the title compound (0.55 g, 75%) as a yellow solid. MS: 102.1 (MH⁺).

C] (2S,3R)-3-Hydroxy-2-methyl-pyrrolidine-1-carboxylic acid tert-butyl ester Boc anhydride (0.44 g, 2 mmol) in THF (5 ml) was added to a solution of (2S,3R)-2-methyl-pyrrolidin-3-ol hydrochloride (0.28 g, 2 mmol) in aqueous saturated sodium hydrogen carbonate (5 ml) and the mixture stirred for 4 h. The organic layer was separated and concentrated affording the title compound (0.34 g, 85%) as a gum. MS: 202.2 (MH+).

D] (2S,3S)-2-Methyl-pyrrolidin-3-ol hydrochloride

To an ice cold solution of (2S,3R)-3-hydroxy-2-methyl-pyrrolidine-1-carboxylic acid tert-butyl ester (0.34 g, 2 mmol), 4-nitrobenzoic acid (0.34 g, 2 mmol), triphenylphosphine (0.53 g, 2 mmol) in THF (10 ml) was added di-isopropylcarbodiimide (0.39 ml, 2 mmol), the ice bath removed and the reaction allowed to come to room temperature. The mixture was stirred for 2 h after which time silica gel was added to the reaction, the solvent removed by evaporation and (2S,3S)-2-methyl-3-(4-nitro-benzoyloxy)-pyrrolidine-1-carboxylic acid tert-butyl ester eluted with EtOAc:n-heptane (1:1). The eluent was concentrated under vacuum and the residue (0.24 g, 1 mmol) redissolved in MeOH (5 ml) and aqueous sodium hydroxide (0.23 ml, 6 M in water, 1 mmol) added and the mixture stirred for 40 minutes. The reaction was then concentrated, the residue redissolved in CH₂Cl₂ and washed with water, the organic was dried (Na₂SO₄) and concentrated. Treatment of the residue (0.1 g, 0.05 mmol) with a 4 M solution of hydrochloric acid in dioxane (5 ml) for 1 h affords the title compound (0.1 g, quant) as a yellow gum after concentration. MS: 102.1 (MH+).

E] 5-Cyclopropyl-3-methyl-1-(3-trifluoromethoxy-phenyl)-1H-pyrazol-4-yl]-[4-((2S,3S)-3-hydroxy-2-methyl-pyrrolidin-1-yl)-piperidin-1-yl]-methanone The title compound was prepared from intermediate 15 and (2S,3S)-2-methyl-pyrrolidin-3-ol hydrochloride in direct analogy to the general procedure used in example 129. MS: 493.2 (MH+).

Example 181

[5-Cyclopropyl-3-methyl-1-(3-trifluoromethyl-phenyl)-1H-pyrazol-4-yl]-[4-((S)-2-hydroxymethyl-pyrrolidin-1-yl)-piperidin-1-yl]-methanone

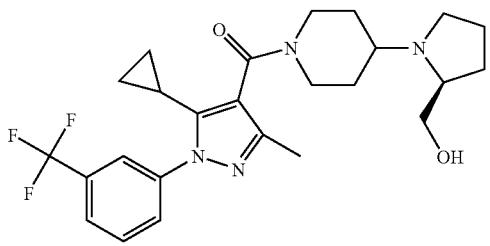

A] 5-Cyclopropyl-3-methyl-1-(3-trifluoromethyl-phenyl)-1H-pyrazole-4-carboxylic acid The title compound was prepared analogously to intermediate 14, starting from 3-trifluoromethylhydrazine. MS: 311.1 (MH+).

B] [5-Cyclopropyl-3-methyl-1-(3-trifluoromethyl-phenyl)-1H-pyrazole-4-carbonyl]-piperidin-4-one The title compound was prepared analogously to intermediate 15 from 5-cyclopropyl-3-methyl-1-(3-trifluoromethyl-phenyl)-1H-pyrazole-4-carboxylic acid and 4-piperidone hydrate. MS: 392.2 (MH+).

C] [5-Cyclopropyl-3-methyl-1-(3-trifluoromethyl-phenyl)-1H-pyrazol-4-yl]-[4-((S)-2-hydroxymethyl-pyrrolidin-1-yl)-piperidin-1-yl]-methanone The title compound was prepared from 1-[5-Cyclopropyl-3-methyl-1-(3-trifluoromethyl-phenyl)-1H-pyrazole-4-carbonyl]-piperidin-4-one and (S)-1-pyrrolidin-2-yl-methanol in direct analogy to the general procedure used in example 129. MS: 477.3 (MH+).

Example 182

[5-Cyclopropyl-3-methyl-1-(3-trifluoromethyl-phenyl)-1H-pyrazol-4-yl]-[4-((R)-2-hydroxymethyl-pyrrolidin-1-yl)-piperidin-1-yl]-methanone

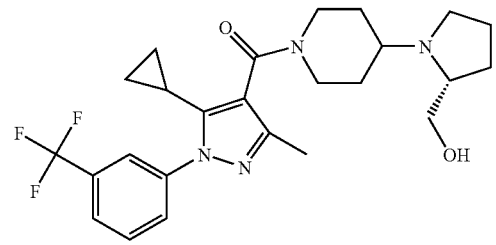

The title compound was prepared from 1-[5-Cyclopropyl-3-methyl-1-(3-trifluoromethyl-phenyl)-1H-pyrazole-4-carbonyl]-piperidin-4-one (Example 181B) and (R)-1-pyrrolidin-2-yl-methanol in direct analogy to the general procedure used in example 129. MS: 477.3 (MH+).

Example 183

[5-Cyclopropyl-3-methyl-1-(3-trifluoromethyl-phenyl)-1H-pyrazol-4-yl]-[4-((S)-3-hydroxy-pyrrolidin-1-yl)-piperidin-1-yl]-methanone

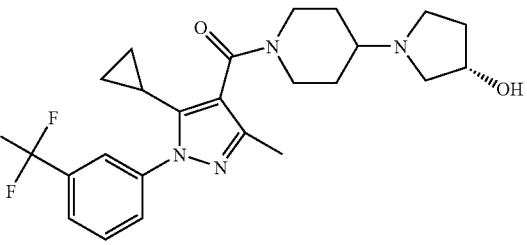

The title compound was prepared from 1-[5-Cyclopropyl-3-methyl-1-(3-trifluoromethyl-phenyl)-1H-pyrazole-4-carbonyl]-piperidin-4-one (Example 181B) and (S)-3-hydroxyl-pyrrolidine in direct analogy to the general procedure used in example 129. MS: 463.3 (MH+).

Example 184

[5-Cyclopropyl-3-methyl-1-(3-trifluoromethyl-phenyl)-1H-pyrazol-4-yl]-[4-((R)-3-hydroxy-pyrrolidin-1-yl)-piperidin-1-yl]-methanone

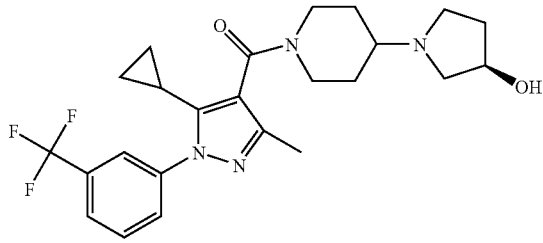

The title compound was prepared from 1-[5-Cyclopropyl-3-methyl-1-(3-trifluoromethyl-phenyl)-1H-pyrazole-4-carbonyl]-piperidin-4-one (Example 181B) and (R)-3-hydroxyl-pyrrolidine in direct analogy to the general procedure used in example 129. MS: 463.3 (MH$^+$).

Example 185

N—((R)-1-{1-[5-Cyclopropyl-3-methyl-1-(3-trifluoromethyl-phenyl)-1H-pyrazole-4-carbonyl]-piperidin-4-yl}-pyrrolidin-3-yl)-acetamide

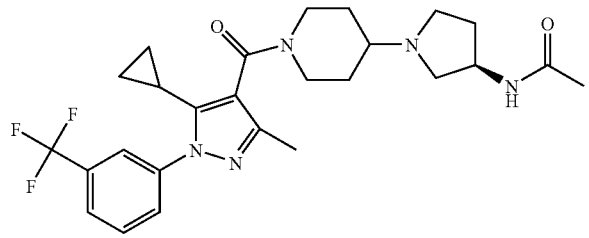

The title compound was prepared from 1-[5-Cyclopropyl-3-methyl-1-(3-trifluoromethyl-phenyl)-1H-pyrazole-4-carbonyl]-piperidin-4-one (Example 181B) and (R)—N-pyrrolidin-3-yl-acetamide in direct analogy to the general procedure used in example 129. MS: 504.3 (MH$^+$).

Example 186

N—((S)-1-{1-[5-Cyclopropyl-3-methyl-1-(3-trifluoromethyl-phenyl)-1H-pyrazole-4-carbonyl]-piperidin-4-yl}-pyrrolidin-3-yl)-acetamide

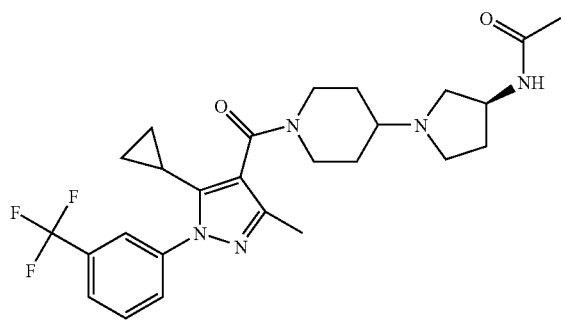

The title compound was prepared from 1-[5-Cyclopropyl-3-methyl-1-(3-trifluoromethyl-phenyl)-1H-pyrazole-4-carbonyl]-piperidin-4-one (Example 181B) and (S)—N-pyrrolidin-3-yl-acetamide in direct analogy to the general procedure used in example 129. MS: 504.3 (MH$^+$).

Example 187

[5-Cyclopropyl-3-methyl-1-(3-trifluoromethoxy-phenyl)-1H-pyrazol-4-yl]-[4-((2R,3S)-3-hydroxy-2-methyl-pyrrolidin-1-yl)-piperidin-1-yl]-methanone

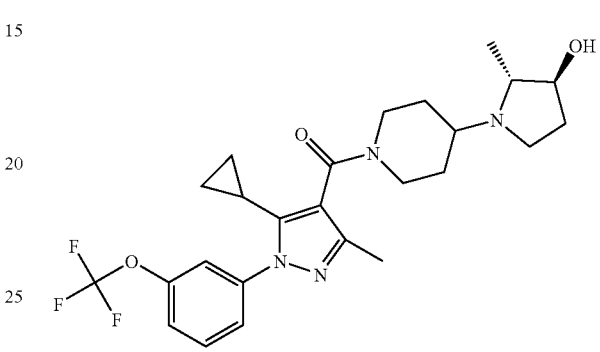

A] (2R,3S)-2-Methyl-pyrrolidin-3-ol hydrochloride

The title compound was prepared in analogy to example 180B (starting from L-malic acid). MS: 101.2 (MH$^+$).

B] [5-Cyclopropyl-3-methyl-1-(3-trifluoromethoxy-phenyl)-1H-pyrazol-4-yl]-[4-((2R,3S)-3-hydroxy-2-methyl-pyrrolidin-1-yl)-piperidin-1-yl]-methanone The title compound was prepared from intermediate 15 and (2R,3S)-2-methyl-pyrrolidin-3-ol hydrochloride in direct analogy to the general procedure used in example 129. MS: 493.3 (MH$^+$).

Example 188

[5-Cyclopropyl-3-methyl-1-(3-trifluoromethoxy-phenyl)-1H-pyrazol-4-yl]-[4-((2R,3R)-3-hydroxy-2-methyl-pyrrolidin-1-yl)-piperidin-1-yl]-methanone

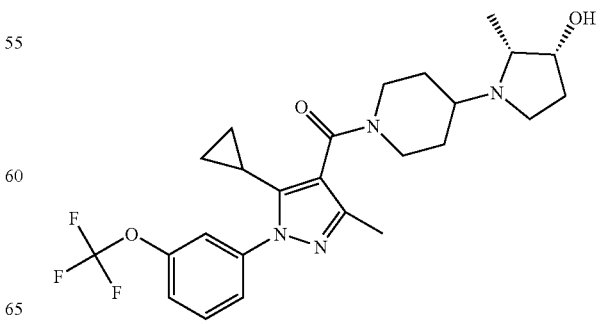

A] (2R,3R)-2-methyl-pyrrolidin-3-ol hydrochloride

The title compound was prepared in analogy to example 180E starting from (2R,3S)-2-methyl-pyrrolidin-3-ol hydrochloride (example 180A). MS: 101.2 (MH$^+$).

B] [5-Cyclopropyl-3-methyl-1-(3-trifluoromethoxy-phenyl)-1H-pyrazol-4-yl]-[4-((2R,3S)-3-hydroxy-2-methyl-pyrrolidin-1-yl)-piperidin-1-yl]-methanone The title compound was prepared from intermediate 15 and (2R,3R)-2-methyl-pyrrolidin-3-ol hydrochloride in direct analogy to the general procedure used in example 150. MS: 493.2 (MH$^+$).

Example 189

[5-Cyclopropyl-3-methyl-1-(3-trifluoromethyl-phenyl)-1H-pyrazol-4-yl]-[4-((2R,3S)-3-hydroxy-2-methyl-pyrrolidin-1-yl)-piperidin-1-yl]-methanone

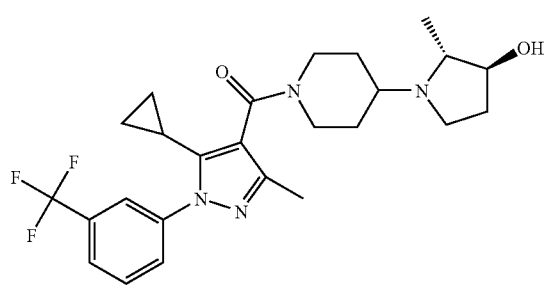

The title compound was prepared from 1-[5-Cyclopropyl-3-methyl-1-(3-trifluoromethyl-phenyl)-1H-pyrazole-4-carbonyl]-piperidin-4-one (Example 181B) and (2R,3S)-2-methyl-pyrrolidin-3-ol hydrochloride (example 187A) in direct analogy to the general procedure used in example 129. MS: 477.2 (MH$^+$).

Example 190

[5-Cyclopropyl-3-methyl-1-(3-trifluoromethyl-phenyl)-1H-pyrazol-4-yl]-[4-((2R,3R)-3-hydroxy-2-methyl-pyrrolidin-1-yl)-piperidin-1-yl]-methanone

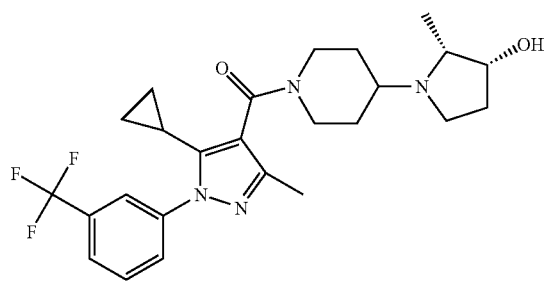

The title compound was prepared from 1-[5-Cyclopropyl-3-methyl-1-(3-trifluoromethyl-phenyl)-1H-pyrazole-4-carbonyl]-piperidin-4-one (Example 181B) and (2R,3R)-2-methyl-pyrrolidin-3-ol hydrochloride (example 188A) in direct analogy to the general procedure used in example 129. MS: 477.3 (MH$^+$).

Example 191

[5-Cyclopropyl-3-methyl-1-(3-trifluoromethoxy-phenyl)-1H-pyrazol-4-yl-(3,3-dimethyl-4-pyrrolidin-1-yl-piperidin-1-yl)-methanone

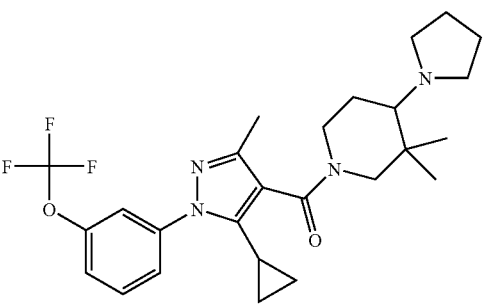

A] 1-(1-Benzyl-3,3-dimethyl-piperidin-4-yl)-pyrrolidin-2-one

To an ice cold solution of 1-benzyl-3,3-dimethyl-piperidin-4-one (0.5 g, 2 mmol) (J. Med. Chem. Lett. 2003, 13, 1627) in CH$_2$Cl$_2$ (10 ml) was added methyl 4-aminobutyrate hydrochloride (0.7 g, 5 mmol), acetic acid (0.4 ml, 7 mmol), triethylamine (0.5 ml, 5 mmol) and sodium triacetoxyborohydride (0.5 g, 3 mmol). The mixture was allowed to reach room temperature and was stirred for 16 h after which time it was washed with saturated sodium hydrogen carbonate solution, dried (Na$_2$SO$_4$) and concentrated. The residue (0.6 g, 2 mmol) was then redissolved in MeOH (10 ml), potassium carbonate (0.3 g, 2 mmol) added and the mixture heated to 70° C. for 2 h. The mixture was then filtered, the methanol evaporated and the residue redissolved in DMF (10 ml) and reacted with EDCl (0.4 g, 2 mmol) at 60° C. for 2 h after which time the DMF was evaporated, the residue taken up in CH$_2$Cl$_2$, washed with saturated sodium hydrogen carbonate solution, dried (Na$_2$SO$_4$) and concentrated. Flash column chromatography (EtOAc:n-heptane 2:1) afforded the title compound (0.4 g, 85%) as yellow oil. MS: 287.4 (MH$^+$).

B] 3,3-Dimethyl-4-pyrrolidin-1-yl-piperidine dihydrochloride

To a solution of 1-(1-benzyl-3,3-dimethyl-piperidin-4-yl)-pyrrolidin-2-one (0.4 g, 1 mmol) in dry THF under Ar was added lithium aluminium hydride (0.2 g, 5 mmol). The mixture was stirred for 2 h, after which time it was cautiously poured onto cold saturated sodium hydrogen carbonate and extracted with CH$_2$Cl$_2$ and the combined organic dried (Na$_2$SO$_4$) and concentrated. The residue was redissolved in MeOH (10 ml), the pH made acidic by addition of 25% hydrochloric acid, 10% palladium on charcoal (0.05 g) added and the mixture stirred under an atmosphere of hydrogen for 16 h. Filtration of the reaction over Hyflo and concentration afforded the title compound (0.4 g, quant) as a white solid. MS: 183.2 (MH+).

C] [5-Cyclopropyl-3-methyl-1-(3-trifluoromethoxy-phenyl)-1H-pyrazol-4-yl]-(3,3-dimethyl-4-pyrrolidin-1-yl-piperidin-1-yl)-methanone The title compound was prepared from intermediate 14 and 3,3-dimethyl-4-pyrrolidin-1-yl-piperidine dihydrochloride in direct analogy to the general procedure used in example 150. MS: 491.4 (MH+).

Example 192

[5-Cyclopropyl-3-methyl-1-(3-trifluoromethyl-phenyl)-1H-pyrazol-4-yl]-(3,3-dimethyl-4-pyrrolidin-1-yl-piperidin-1-yl)-methanone

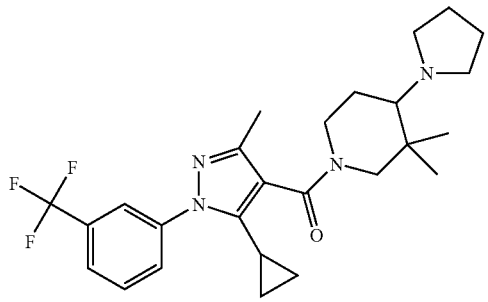

The title compound was prepared from 5-cyclopropyl-3-methyl-1-(3-trifluoromethyl-phenyl)-1H-pyrazole-4-carboxylic acid (Example 181A) and 3,3-dimethyl-4-pyrrolidin-1-yl-piperidine dihydrochloride in direct analogy to the general procedure used in example 150. MS: 457.4 (MH+).

Example 193

[5-Cyclopropyl-3-methyl-1-(3-trifluoromethoxy-phenyl)-1H-pyrazol-4-yl]-((trans)-2-hydroxymethyl-4-pyrrolidin-1-yl-piperidin-1-yl)-methanone

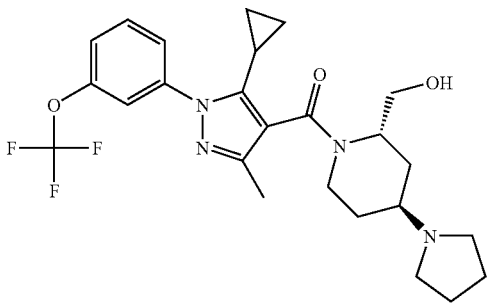

A] (trans)-4-Pyrrolidin-1-yl-piperidine-1,2-dicarboxylic acid 1-tert-butyl ester 2-ethyl ester To a solution of 1-benzyl-4-oxo-piperidine-2-carboxylic acid ethyl ester (0.8 g, 3 mmol) (Tetrahedron 2001, 57, 4995) in CH2Cl2 (10 ml) was added pyrrolidine (0.3 ml, 4 mmol), acetic acid (0.2 ml, 4 mmol) and sodium triacetoxyborohydride (0.8 g, 4 mmol) and the mixture stirred for 1 h, after which time it was washed with saturated sodium hydrogen carbonate solution, dried (Na2SO4) and concentrated. The residue was redissolved in MeOH (10 ml), Boc anhydride (0.8 g, 3 mmol), 10% palladium on charcoal (0.1 g) were added and the mixture stirred under an atmosphere of hydrogen for 16 h. The reaction was filtered over Hyflo and concentrated. Flash column chromatography (CH2Cl2:MeOH 98:2-9:1) afforded the title product (0.5 g, 48%) as a yellow oil. MS: 327.3 (MH+).

B] trans-(4-Pyrrolidin-1-yl-piperidin-2-yl)-methanol dihydrochloride

To an ice-cold suspension of lithium aluminium hydride (0.1 g, 3 mmol) in THF (5 ml) was added a solution (trans)-4-pyrrolidin-1-yl-piperidine-1,2-dicarboxylic acid 1-tert-butyl ester 2-ethyl ester (0.4 g, 1 mmol). The mixture was allowed to reach room temperature and was stirred for a further 1 h after which time water was cautiously added to the reaction, the reaction filtered, washing with EtOAc, and the filtrate concentrated. The residue was taken up in 4M hydrochloric acid in dioxane (2 ml) and stirred for 30 minutes, after which time the reaction mixture was concentrated to afford the title compound (0.2 g, 55%) as a white powder. MS: 185.1 (MH+).

C] [5-Cyclopropyl-3-methyl-1-(3-trifluoromethoxy-phenyl)-1H-pyrazol-4-yl]-((trans)-2-hydroxymethyl-4-pyrrolidin-1-yl-piperidin-1-yl)-methanone The title compound was prepared from intermediate 14 and trans-(4-pyrrolidin-1-yl-piperidin-2-yl)-methanol dihydrochloride in direct analogy to the general procedure used in example 150. MS: 493.2 (MH+).

Example 194

[5-Cyclopropyl-3-methyl-1-(3-trifluoromethyl-phenyl)-1H-pyrazol-4-yl]-((trans)-2-hydroxymethyl-4-pyrrolidin-1-yl-piperidin-1-yl)-methanone

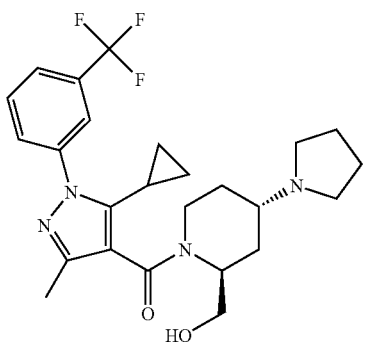

The title compound was prepared from 5-cyclopropyl-3-methyl-1-(3-trifluoromethyl-phenyl)-1H-pyrazole-4-carboxylic acid (Example 181A) and trans-(4-pyrrolidin-1-yl-piperidin-2-yl)-methanol dihydrochloride (example 193B) in direct analogy to the general procedure used in example 150. MS: 477.2 (MH+).

Example 195

[5-Cyclopropyl-3-methyl-1-(3-trifluoromethoxy-phenyl)-1H-pyrazol-4-yl]-((3S,4S)-3-methyl-4-pyrrolidin-1-yl-piperidin-1-yl)-methanone

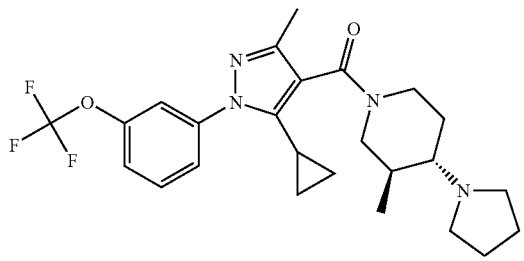

A] 4-Amino-3-methyl-piperidine-1-carboxylic acid tert-butyl ester

To an ice-cold solution of 1-benzyl-3-methyl-4-piperidone (5 g, 25 mmol) in MeOH (30 ml) was added, portionwise, sodium borohydride (1.1 g, 30 mmol). The mixture was allowed to reach room temperature and stirred for a further 45 minutes after which time the solvent was evaporated, the residue taken up in $CH_2Cl_2$ and washed with water, dried ($Na_2SO_4$) and concentrated. The residue was redissolved in MeOH, Boc anhydride (5.7 g, 25 mmol) and 10% palladium on charcoal (0.2 g) added and the mixture stirred under an atmosphere of hydrogen for 16 h, after which time it was filtered over Hyflo and concentrated. The residue (3.75 g, 17 mmol) was dissolved in $CH_2Cl_2$ (30 ml) with triethylamine (4.8 ml, 35 mmol), cooled to 0° C. and methanesulfonyl chloride (1.5 ml, 19 mmol) was added dropwise. On completion of the addition the reaction was washed with water, dried ($Na_2SO_4$) and concentrated. The crude mesylate (5.0 g, 17 mmol) was then redissolved in DMF (15 ml), sodium azide added (2.2 g, 34 mmol) and the mixture heated at 80° C. for 2 days. Water was then added to the reaction and the mixture repeatedly extracted with EtOAc, the combined organic was dried ($Na_2SO_4$) and concentrated. The crude azide (3.6 g, 15 mmol) was redissolved in MeOH (20 ml), Rainey nickel added (0.5 g) and the mixture stirred under an atmosphere of hydrogen for 16 h, after which time it was filtered over Hyflo and concentrated affording the title compound (2.5 g, 44%) as a yellow liquid. MS: 215.1 ($MH^+$).

B] (cis)-3-Methyl-4-(2-oxo-pyrrolidin-1-yl)-piperidine-1-carboxylic acid tert-butyl ester and (trans)-3-methyl-4-(2-oxo-pyrrolidin-1-yl)-piperidine-1-carboxylic acid tert-butyl ester To an ice-cold solution of 4-amino-3-methyl-piperidine-1-carboxylic acid tert-butyl ester (2.5 g 12 mmol) and triethylamine (31 ml, 23 mmol) in $CH_2Cl_2$ (100 ml) was added 4-chlorobutyric acid chloride (11 ml, 14 mmol) and the reaction allowed to come to room temperature. The reaction was then washed with water, was dried ($Na_2SO_4$) and concentrated. The crude amide (1.9 g, 6 mmol) was redissolved in DMF (50 ml), cooled to 0° C. and sodium hydride (0.3 g, 12 mmol) was added portionwise. The mixture was allowed to reach room temperature, the reaction concentrated and the residue redissolved in $CH_2Cl_2$ and washed with saturated sodium hydrogen carbonate, dried ($Na_2SO_4$) and concentrated. Flash column chromatography (EtOAc:n-heptane 9:1-95:5) separated the title compounds affording (cis)-3-Methyl-4-(2-oxo-pyrrolidin-1-yl)-piperidine-1-carboxylic acid tert-butyl ester (0.3 g, 18%) and (trans)-3-methyl-4-(2-oxo-pyrrolidin-1-yl)-piperidine-1-carboxylic acid tert-butyl ester (0.63 g, 39%) as yellow oils. MS: 283.4 ($MH^+$).

C] (trans)-3-Methyl-4-pyrrolidin-1-yl-piperidine dihydrochloride

The title compound was prepared in analogy to 193B, by reduction of (trans)-3-methyl-4-(2-oxo-pyrrolidin-1-yl)-piperidine-1-carboxylic acid tert-butyl ester with lithium aluminium hydride and subsequent deprotection with 4M hydrochloric acid in dioxane. MS: 169.2 ($MH^+$).

D] [5-Cyclopropyl-3-methyl-1-(3-trifluoromethoxy-phenyl)-1H-pyrazol-4-yl]-((3S,4S)-3-methyl-4-pyrrolidin-1-yl-piperidin-1-yl)-methanone The title compound was prepared from intermediate 14 and (trans)-3-methyl-4-pyrrolidin-1-yl-piperidine dihydrochloride in direct analogy to the general procedure used in example 150. MS: 477.3 ($MH^+$).

Example 196

[5-Cyclopropyl-3-methyl-1-(3-trifluoromethyl-phenyl)-1H-pyrazol-4-yl]-((3S,4S)-3-methyl-4-pyrrolidin-1-yl-piperidin-1-yl)-methanone

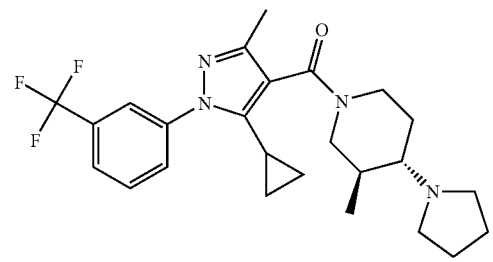

The title compound was prepared from 5-cyclopropyl-3-methyl-1-(3-trifluoromethyl-phenyl)-1H-pyrazole-4-carboxylic acid (Example 181A) and (trans)-3-methyl-4-pyrrolidin-1-yl-piperidine dihydrochloride (example 195C) in direct analogy to the general procedure used in example 150. MS: 461.3 ($MH^+$).

Example 197

[5-Cyclopropyl-3-methyl-1-(3-trifluoromethoxy-phenyl)-1H-pyrazol-4-yl]-((cis)-2-methyl-4-pyrrolidin-1-yl-piperidin-1-yl)-methanone

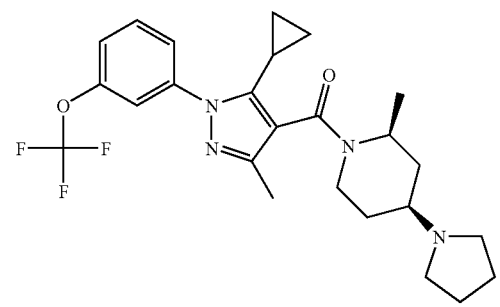

A] (cis)-3-Methyl-4-pyrrolidin-1-yl-piperidine dihydrochloride

The title compound was prepared in analogy to 193B, by reduction of (cis)-3-methyl-4-(2-oxo-pyrrolidin-1-yl)-piperidine-1-carboxylic acid tert-butyl ester (Example 195B) with lithium aluminium hydride and subsequent deprotection with 4M hydrochloric acid in dioxane. MS: 169.2 (MH$^+$).

B] [5-Cyclopropyl-3-methyl-1-(3-trifluoromethoxy-phenyl)-1H-pyrazol-4-yl]-((cis)-2-methyl-4-pyrrolidin-1-yl-piperidin-1-yl)-methanone The title compound was prepared from intermediate 14 and (cis)-3-methyl-4-pyrrolidin-1-yl-piperidine dihydrochloride in direct analogy to the general procedure used in example 150. MS: 477.2 (MH$^+$).

Example 198

[5-Cyclopropyl-3-methyl-1-(3-trifluoromethyl-phenyl)-1H-pyrazol-4-yl]-((cis)-2-methyl-4-pyrrolidin-1-yl-piperidin-1-yl)-methanone

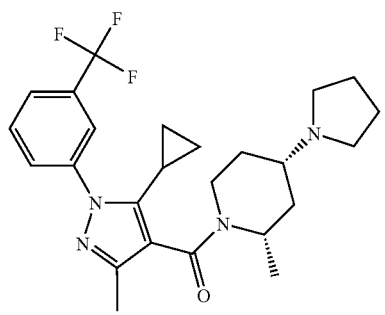

The title compound was prepared from 5-cyclopropyl-3-methyl-1-(3-trifluoromethyl-phenyl)-1H-pyrazole-4-carboxylic acid (Example 181A) and (cis)-3-methyl-4-pyrrolidin-1-yl-piperidine dihydrochloride (example 197A) in direct analogy to the general procedure used in example 150. MS: 461.2 (MH$^+$).

Example 199

[5-Cyclopropyl-3-methyl-1-(3-trifluoromethoxy-phenyl)-1H-pyrazol-4-yl]-((trans)-2-methyl-4-pyrrolidin-1-yl-piperidin-1-yl)-methanone

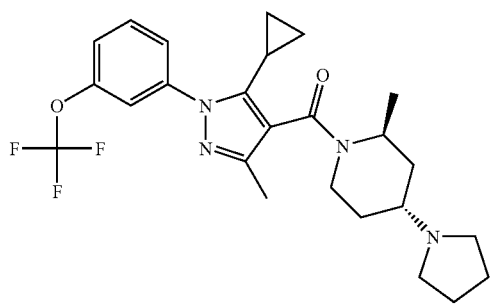

A] (trans) 2-Methyl-4-pyrrolidin-1-yl-piperidine-1-carboxylic acid tert-butyl ester To a solution of 1-benzyl-2-methylpiperdinone (0.6 g, 3 mmol) (Eur. J. Org. Chem. 2001, 975), pyrrolidine (0.26 ml, 3 mmol), acetic acid (0.3 ml, 6 mmol) in CH$_2$Cl$_2$ (10 ml) was added sodium triacetoxyborohydride (0.7 g, 3 mmol). The mixture was stirred for 1 h after which time the reaction was washed with saturated sodium hydrogen carbonate, dried (Na$_2$SO$_4$) and concentrated. The residue (0.7 g, 3 mmol) is then redissolved in MeOH (10 ml), Boc anhydride (0.6 g, 3 mmol) and 10% palladium on charcoal (0.1 g) added and the mixture stirred under an atmosphere of hydrogen for 1 h, after which time it was filtered over Hyflo and concentrated. Flash column chromatography (CH$_2$Cl$_2$:MeOH 95:5) afforded the title compound (0.1 g, 12%) as the minor isomer. MS: 269.2 (MH$^+$).

B] (trans)-2-Methyl-4-pyrrolidin-1-yl-piperidine dihydrochloride

Treatment of (trans) 2-methyl-4-pyrrolidin-1-yl-piperidine-1-carboxylic acid tert-butyl ester (0.1 g, 0.4 mmol) with 4M hydrochloric acid in dioxane (5 ml) for 1 h and subsequent evaporation of the solvent afforded the title compound (0.06 g, 84%) as a white powder. MS: 169.1 (MH$^+$).

C] [5-Cyclopropyl-3-methyl-1-(3-trifluoromethoxy-phenyl)-1H-pyrazol-4-yl]-((trans)-2-methyl-4-pyrrolidin-1-yl-piperidin-1-yl)-methanone The title compound was prepared from intermediate 14 and (trans)-2-methyl-4-pyrrolidin-1-yl-piperidine dihydrochloride in direct analogy to the general procedure used in example 150. MS: 477.2 (MH$^+$).

Example 200

[5-Cyclopropyl-3-methyl-1-(3-trifluoromethyl-phenyl)-1H-pyrazol-4-yl]-((trans)-2-methyl-4-pyrrolidin-1-yl-piperidin-1-yl)-methanone

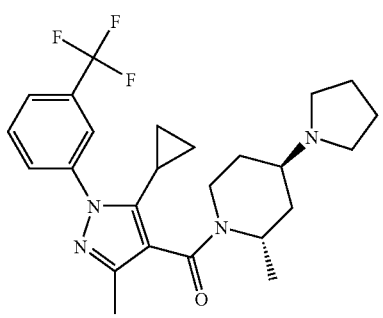

The title compound was prepared from 5-cyclopropyl-3-methyl-1-(3-trifluoromethyl-phenyl)-1H-pyrazole-4-carboxylic acid (Example 181A) and (trans)-2-methyl-4-pyrrolidin-1-yl-piperidine dihydrochloride (example 199B) in direct analogy to the general procedure used in example 150. MS: 461.2 (MH+).

Example 201

[5-Cyclopropyl-3-methyl-1-(3-trifluoromethoxy-phenyl)-1H-pyrazol-4-yl]-((3'S,5'S)-5'-hydroxymethyl-[1,3']bipyrrolidinyl-1'-yl)-methanone

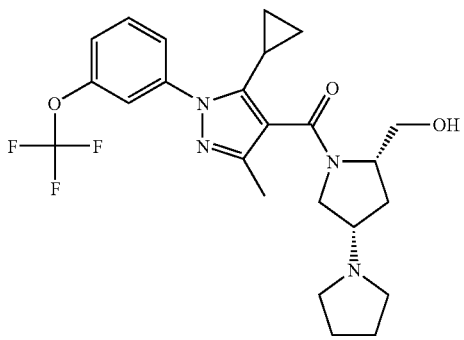

A] 3'S,5'S)-[1,3']Bipyrrolidinyl-1',5'-dicarboxylic acid 1'-tert-butyl ester 5'-methyl ester To a solution of N-t-butoxycarbonyl-4-oxo-L-proline methyl ester (1.0 g, 4 mmol) (J. Org. Chem. 2001, 10, 3593), pyrrolidine (0.4 ml, 5 mmol), acetic add (0.3 ml, 5 mmol) in CH₂Cl₂ (20 ml) was added sodium triacetoxyborohydride (1.0 g, 5 mmol) and the mixture stirred for 2 h. After which time it was washed with saturated sodium hydrogen carbonate, dried (Na₂SO₄) and concentrated. Flash column chromatography (EtOAc:MeOH 95:5) afforded the title compound (1.0 g, 81%) as a yellow oil.

B] (3'S,5'S)-1-[1,3]Bipyrrolidinyl-5'-yl-methanol dihydrochloride

The title compound was prepared in analogy to 193B, by reduction of 3'S,5'S)-[1,3']Bipyrrolidinyl-1',5'-dicarboxylic acid 1'-tert-butyl ester 5'-methyl ester with lithium aluminium hydride and subsequent deprotection with 4M hydrochloric acid in dioxane. MS: 171.3 (MH+).

C] [5-Cyclopropyl-3-methyl-1-(3-trifluoromethoxy-phenyl)-1H-pyrazol-4-yl]-((3'S,5'S)-5'-hydroxymethyl-[1,3']bipyrrolidinyl-1'-yl)-methanone The title compound was prepared from intermediate 14 and (3'S,5'S)-1-[1,3']bipyrrolidinyl-5'-yl-methanol dihydrochloride in direct analogy to the general procedure used in example 150. MS: 479.2 (MH+).

Example 202

N-((3R,5S)-1-{1-[5-Cyclopropyl-3-methyl-1-(3-trifluoromethoxy-phenyl)-1H-pyrazole-4-carbonyl]-piperidin-4-yl}-5-hydroxymethyl-pyrrolidin-3-yl)-acetamide

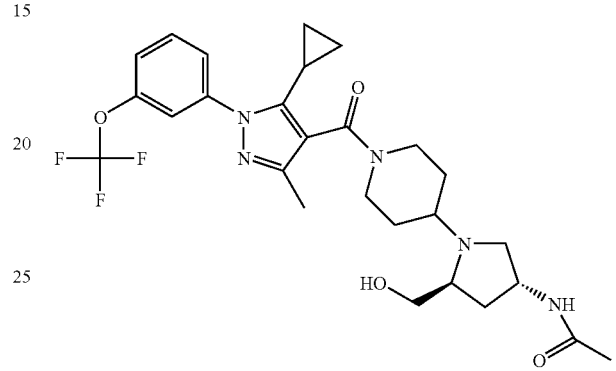

A] N-((3R,5S)-5-Hydroxymethyl-pyrrolidin-3-yl)-acetamide hydrochloride

To an ice-cold suspension of lithium aluminium hydride (0.6 g, 15 mmol) in THF (10 ml) was added a solution of (2S,4R)-4-azido-pyrrolidine-1,2-dicarboxylic acid 1-tert-butyl ester 2-methyl ester (1.0 g, 4 mmol) in THF (5 mL) and the mixture stirred for 1 h. Water was then cautiously added to the reaction and the mixture filtered and concentrated. The residue was then taken up in CH₂Cl₂ (10 ml) and saturated sodium carbonate (10 ml) and acetic anhydride (0.3 ml, 3 mmol) added. The mixture was stirred for 2 h after which time the organic was collected, dried (Na₂SO₄) and concentrated. The residue (0.6 g, 2 mmol) was then treated with 4 M hydrochloric acid in dioxane (5 ml) for 1 h, evaporation of the solvent afforded the title compound (0.5 g, 80%) as a yellow solid. MS: 159.1 (MH+).

B] N-((3R,5S)-1-{1-[5-Cyclopropyl-3-methyl-1-(3-trifluoromethoxy-phenyl)-1H-pyrazole-4-carbonyl]-piperidin-4-yl}-5-hydroxymethyl-pyrrolidin-3-yl)-acetamide The title compound was prepared from intermediate 15 and N-((3R,5S)-5-hydroxymethyl-pyrrolidin-3-yl)-acetamide hydrochloride in direct analogy to the general procedure used in example 129. MS: 550.3 (MH+).

Example 203

N-((3R,5S)-1-{1-[5-Cyclopropyl-3-methyl-1-(3-trifluoromethyl-phenyl)-1H-pyrazole-4-carbonyl]-piperidin-4-yl}-5-hydroxymethyl-pyrrolidin-3-yl)-acetamide

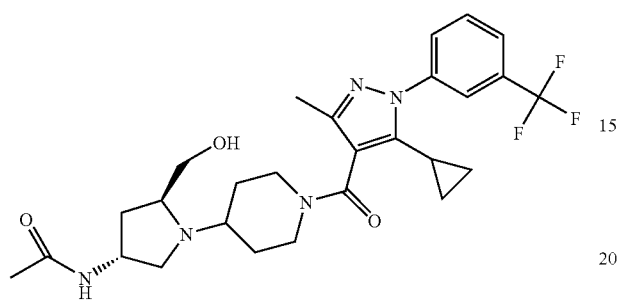

The title compound was prepared from 1-[5-Cyclopropyl-3-methyl-1-(3-trifluoromethyl-phenyl)-1H-pyrazole-4-carbonyl]-piperidin-4-one (Example 181B) and N-((3R,5S)-5-hydroxymethyl-pyrrolidin-3-yl)-acetamide hydrochloride in direct analogy to the general procedure used in example 129. MS: 534.2 (MH$^+$).

Example 204

N-((2S,3R)-1-{1-[5-Cyclopropyl-3-methyl-1-(3-trifluoromethoxy-phenyl)-1H-pyrazole-4-carbonyl]-piperidin-4-yl}-2-hydroxymethyl-pyrrolidin-3-yl)-acetamide

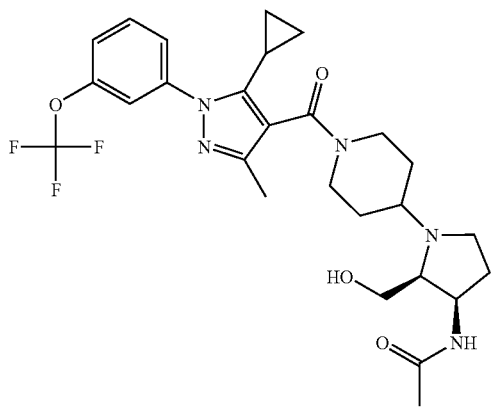

A] N-((2S,3R)-2-Hydroxymethyl-pyrrolidin-3-yl)-acetamide hydrochloride

The title compound was prepared from (2S,3R)-3-azido-pyrrolidine-1,2-dicarboxylic acid 1-tert-butyl ester 2-methyl ester (Org. Lett. 2001, 3, 2481) in direct analogy to example 202A. MS: 159.1 (MH$^+$).

B] N-((2S,3R-1-{1-[5-Cyclopropyl-3-methyl-1-(3-trifluoromethoxy-phenyl)-1H-pyrazole-4-carbonyl]-piperidin-4-yl}-2-hydroxymethyl-pyrrolidin-3-yl)-acetamide The title compound was prepared from intermediate 15 and N-((2S,3R)-2-hydroxymethyl-pyrrolidin-3-yl)-acetamide hydrochloride in direct analogy to the general procedure used in example 129. MS: 550.2 (MH$^+$).

Example 205

N-((2S,3R)-1-{1-[5-Cyclopropyl-3-methyl-1-(3-trifluoromethyl-phenyl)-1H-pyrazole-4-carbonyl]-piperidin-4-yl}-2-hydroxymethyl-pyrrolidin-3-yl)-acetamide

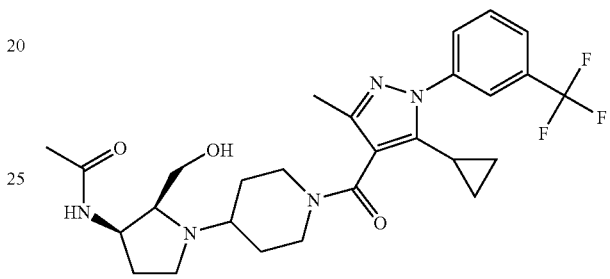

The title compound was prepared from 1-[5-Cyclopropyl-3-methyl-1-(3-trifluoromethyl-phenyl)-1H-pyrazole-4-carbonyl]-piperidin-4-one (Example 181B) and N-((2S,3R)-2-hydroxymethyl-pyrrolidin-3-yl)-acetamide hydrochloride in direct analogy to the general procedure used in example 129. MS: 534.2 (MH$^+$).

Example 206

[5-Cyclopropyl-3-methyl-1-(4-trifluoromethoxy-phenyl)-1H-pyrazol-4-yl]-(4-pyrrolidin-1-yl-piperidin-1-yl)-methanone

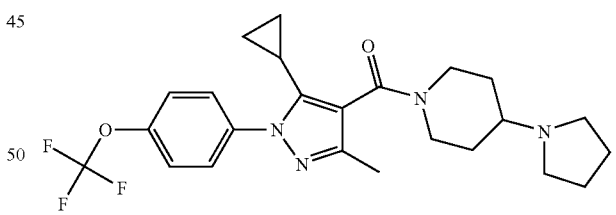

A] 5-Cyclopropyl-3-methyl-1-(4-trifluoromethoxy-phenyl)-1H-pyrazole-4-carboxylic acid The title compound was prepared analogously to intermediate 14, starting from 3-trifluoromethoxyphenylhydrazine. MS: 327.13 (MH$^+$).

B] [5-Cyclopropyl-3-methyl-1-(4-trifluoromethoxy-phenyl)-1H-pyrazol-4-yl]-(4-pyrrolidin-1-yl-piperidin-1-yl)-methanone A The title compound was prepared from 5-Cyclopropyl-3-methyl-1-(4-trifluoromethoxy-phenyl)-1H-pyrazole-4-carboxylic acid and 4-pyrrolidin-1-yl-piperidine in direct analogy to the general procedure used in example 150. MS: 463.2 (MH⁺).

Example 207

[5-Cyclopropyl-3-methyl-1-(4-trifluoromethoxy-phenyl)-1H-pyrazol-4-yl]-[4-((S)-2-hydroxymethyl-pyrrolidin-1-yl)-piperidin-1-yl]-methanone

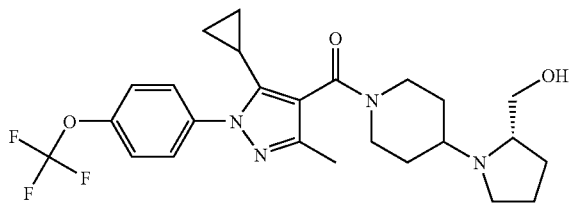

The title compound was prepared from 5-cyclopropyl-3-methyl-1-(4-trifluoromethoxy-phenyl)-1H-pyrazole-4-carboxylic acid and ((S)-1-piperidin-4-yl-pyrrolidin-2-yl)-methanoldihydrochloride (Example 161A]) in direct analogy to the general procedure used in example 150. MS: 493.2 (MH⁺).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidon in water. The granulate is mixed with magnesiumstearate and the flavouring additives and filled into sachets.

What is claimed:

1. A Compound of formula (I)

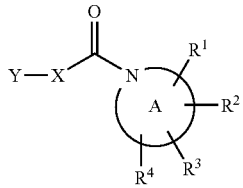

wherein

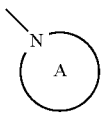

is a non-aromatic mono-cyclic radical of four to eight ring atoms, in which one or two ring atoms are nitrogen atoms, with the remaining ring atoms being carbon atoms;

provided that, when

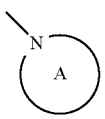

contains the second ring nitrogen atom, said ring nitrogen atom is not directly bonded to another heteroatom or to a carbonyl group;

X is—

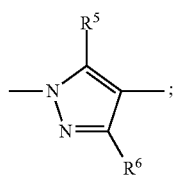

Y is phenyl, and said phenyl is substituted by one, two or three substituents independently selected from the group consisting of $C_{1-8}$ alkyl, halo $C_{1-6}$ alkyl, $C_{1-6}$ alkoxy, halo $C_{1-6}$ alkyoxy, halogen, cyano, optionally substituted phenyl, optionally substituted heteroaryl, optionally substituted $C_{3-7}$ cycloalkyl, optionally substituted heterocyclyl, $C_{1-6}$ alkylvinyl, halo $C_{1-6}$ alkylvinyl, optionally substituted $C_{3-7}$ cycloalkylvinyl, optionally substituted heterocyclylvinyl, optionally substituted phenylvinyl, optionally substituted heteroarylvinyl, $C_{1-6}$ alkylethynyl, halo $C_{1-6}$ alkylethynyl, optionally substituted $C_{3-7}$ cycloalkylethynyl, optionally substituted heterocyclylethynyl, optionally substituted phenylethynyl, optionally substituted heteroarylethynyl, $C_{1-6}$ alkylcarbonylamino, halo $C_{1-6}$ alkyl carbonylamino, optionally substituted $C_{3-7}$ cycloalkylcarbonylamino, optionally substituted heterocyclylcarbonylamino, optionally substituted phenylcarbonylamino and optionally substituted heteroarylcarbonylamino;

$R^1$, $R^2$, $R^3$ and $R^4$ when attached to a ring carbon atom, independently are selected from the group consisting of hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, halogen, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl or amino optionally substituted by one or two substituents independently selected from $C_{1-6}$ alkyl, acyl, heteroalkyl, optionally substituted $C_{3-7}$ cycloalkyl or optionally substituted heterocyclyl and optionally substituted heterocyclyl, in which one of the ring carbon atoms of the heterocyclyl may be a ring carbon atom of another ring which is $C_{3-7}$ cycloalkyl or heterocyclyl, one or two ring carbon atoms of said another ring being optionally replaced by a carbonyl group; and, when two of $R^1$, $R^2$, $R^3$ and $R^4$ are attached to the same ring carbon atom, they can, together with the carbon atom to which they are attached, form a $C_{3-7}$ cycloalkyl ring or heterocyclyl ring; or when attached to a ring nitrogen atom, $R^1$, $R^2$, $R^3$ and $R^4$ are independently hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl, optionally substituted $C_{3-7}$ cycloalkyl $C_{1-6}$ alkyl, optionally substituted heterocyclyl or optionally substituted heterocyclyl-$C_{1-6}$ alkyl;

$R^5$ is hydrogen, $C_{1-6}$ alkyl, heteroalkyl, or optionally substituted $C_{3-7}$ cycloalkyl;

$R^6$ is hydrogen, $C_{1-6}$ alkyl, heteroalkyl or $C_{3-7}$ cycloalkyl;

provided that compounds wherein Y is mono- or difluorosubstituted phenyl, mono- or di-methyl substituted phenyl, mono-chloro substituted phenyl, monomethoxy substituted phenyl, mono-phenyl substituted phenyl, mono-chloro-mono-methyl substituted phenyl and mono-fluoro-mono-methoxy substituted phenyl are excluded;

or pharmaceutically acceptable salt thereof.

2. The compound of claim 1, wherein

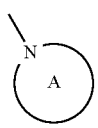

is diazepan-1-yl, piperazin-1-yl, piperidin-1-yl or pyrrolidin-1-yl.

3. The compound of claim 2, wherein

is piperidin-1-yl.

4. The compound of claim 3, wherein two of $R^1$, $R^2$, $R^3$ and $R^4$ are hydrogen, and the other two are,
- when attached to a ring carbon atom, independently hydrogen, hydroxy, amino optionally substituted by one or two substituents independently selected from the group consisting of $C_{1-6}$ alkyl, heteroalkyl, optionally substituted $C_{3-7}$ cycloalkyl and optionally substituted heterocyclyl or optionally substituted heterocyclyl, in which one of the ring carbon atoms of the heterocyclyl may be a ring carbon atom of another ring which is a heterocyclyl, one or two ring carbon atoms of said other ring being optionally replaced by a carbonyl group, and
- when they are attached to the same ring carbon atom, they can, together with the carbon atom to which they are attached, form a heterocyclyl ring, and
- when attached to a ring nitrogen atom, the other two are independently hydrogen, $C_{1-6}$ alkyl, heteroalkyl, optionally substituted $C_{3-7}$ cycloalkyl or optionally substituted heterocyclyl-$C_{1-6}$ alkyl.

5. The compound of claim 1, wherein three of $R^1$, $R^2$, $R^3$ and $R^4$ are hydrogen, and the other one is attached to a ring carbon atom and optionally substituted heterocyclyl, in which one of the ring carbon atoms of the heterocyclyl may be a ring carbon atom of another ring which is a heterocyclyl, one or two ring carbon atoms of said other ring being optionally replaced by a carbonyl group.

6. The compound of claim 5, wherein three of $R^1$, $R^2$, $R^3$ and $R^4$ are hydrogen, and the other one is attached to a ring carbon atom and optionally substituted pyrrolidin-1-yl, in which one of the ring carbon atoms of the pyrrolidin-1-yl may be a ring carbon atom of another ring which is a heterocyclyl, one or two ring carbon atoms of said other ring being optionally replaced by a carbonyl group.

7. The compound of claim 6, wherein $R^5$ is $C_{1-6}$ alkyl or optionally substituted $C_{3-7}$ cycloalkyl.

8. The compound of claim 7, wherein $R^5$ is methyl or cyclopropyl.

9. The compound of claim 8, wherein $R^6$ is $C_{1-6}$ alkyl.

10. The compound of claim 9, wherein $R^6$ is methyl.

11. The compound of claim 10, wherein Y is phenyl, said phenyl being substituted by one or two substituents independently selected from the group consisting of $C_{1-8}$ alkyl, halo $C_{1-6}$ alkyl, $C_{1-6}$ alkoxy, halo $C_{1-6}$ alkyoxy, halogen, optionally substituted phenyl, optionally substituted heteroaryl, optionally substituted $C_{3-7}$ cycloalkylvinyl, optionally substituted phenylvinyl, $C_{1-6}$ alkylethynyl, optionally substituted phenylethynyl, halo $C_{1-6}$ alkyl carbonylamino and optionally substituted phenylcarbonylamino.

12. The compound of claim 11, wherein Y is phenyl, said phenyl being substituted by one or two substituents independently selected from the group consisting of chloro, halo $C_{1-6}$ alkyl and halo $C_{1-6}$ alkyoxy.

13. The compound of claim 12, wherein Y is phenyl, said phenyl, being substituted by one substituent which is halo $C_{1-6}$ alkyl or halo $C_{1-6}$ alkyoxy.

14. The compound of claim 13, wherein Y is phenyl said phenyl being substituted by one substituent which is trifluoromethyl or trifluoromethoxy.

15. A compound of claim 1 selected from the group consisting of
- [5-Cyclopropyl-3-methyl-1-(3-trifluoromethoxy-phenyl)-1H-pyrazol-4-yl]-(4-pyrrolidin-1-yl-piperidin-1-yl)-methanone,
- [5-Cyclopropyl-3-methyl-1-(3-trifluoromethyl-phenyl)-1H-pyrazol-4-yl]-(4-pyrrolidin-1-yl-piperidin-1-yl)-methanone,
- [5-Cyclopropyl-3-methyl-1-(3-trifluoromethoxy-phenyl)-1H-pyrazol-4-yl]-[4-((S)-2-hydroxymethyl-pyrrolidin-1-yl)-piperidin-1-yl]-methanone,
- 7-{1-[5-Cyclopropyl-3-methyl-1-(3-trifluoromethoxy-phenyl)-1H-pyrazole-4-carbonyl]-piperidin-4-yl}-1,3,7-triaza-spiro[4.4]nonane-2,4-dione,
- [5-Cyclopropyl-3-methyl-1-(3-trifluoromethoxy-phenyl)-1H-pyrazol-4-yl]-[4-((R)-3-hydroxy-pyrrolidin-1-yl)-piperidin-1-yl]-methanone,
- N—((R)-1-{1-[5-Cyclopropyl-3-methyl-1-(3-trifluoromethoxy-phenyl)-1H-pyrazole-4-carbonyl]-piperidin-4-yl}-pyrrolidin-3-yl)-acetamide,
- [5-Cyclopropyl-3-methyl-1-(3-trifluoromethyl-phenyl)-1H-pyrazol-4-yl]-[4-((S)-2-hydroxymethyl-pyrrolidin-1-yl)-piperidin-1-yl]-methanone,
- N—((R)-1-{1-[5-Cyclopropyl-3-methyl-1-(3-trifluoromethyl-phenyl)-1H-pyrazole-4-carbonyl]-piperidin-4-yl}-pyrrolidin-3-yl)-acetamide and
- N—((3R,5S)-1-{1-[5-Cyclopropyl-3-methyl-1-(3-trifluoromethoxy-phenyl)-1H-pyrazole-4-carbonyl]-piperidin-4-yl}-5-hydroxymethyl-pyrrolidin-3-yl)-acetamide.

16. A process for manufacturing compounds of formula (I)

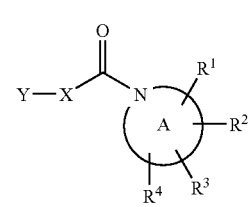

(I)

comprising a step of reacting compounds of formula (II)

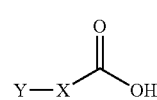

(II)

with compounds of formula (III)

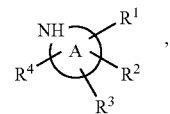

(III)

wherein

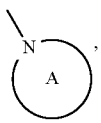

$R^1$, $R^2$, $R^3$, $R^4$, X and Y are as defined in claim 1.

17. A Pharmaceutical composition comprising a compound of the formula

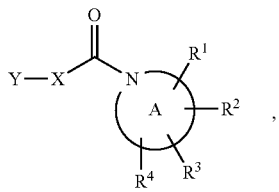 (I)

wherein

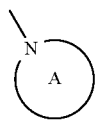

is a non-aromatic mono-cyclic radical of four to eight ring atoms, in which one or two ring atoms are nitrogen atoms with the remaining ring atoms being carbon atoms;
provided that, when

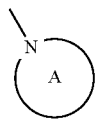

contains the second ring nitrogen atom, said ring nitrogen atom is not directly bonded to another heteroatom or to a carbonyl group;

X

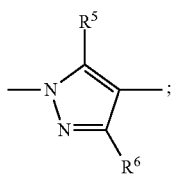

Y is phenyl, said phenyl being substituted by one, two or three substituents independently selected from the group consisting of $C_{1-8}$ alkyl, halo $C_{1-6}$ alkyl, $C_{1-6}$ alkoxy, halo $C_{1-6}$ alkyoxy, halogen, cyano, optionally substituted phenyl, optionally substituted heteroaryl, optionally substituted $C_{3-7}$ cycloalkyl, optionally substituted heterocyclyl, $C_{1-6}$ alkylvinyl, halo $C_{1-6}$ alkylvinyl, optionally substituted $C_{3-7}$ cycloalkylvinyl, optionally substituted heterocyclylvinyl, optionally substituted phenylvinyl, optionally substituted heteroarylvinyl, $C_{1-6}$ alkylethynyl, halo $C_{1-6}$ alkylethynyl, optionally substituted $C_{3-7}$ cycloalkylethynyl, optionally substituted heterocyclylethynyl, optionally substituted phenylethynyl, optionally substituted heteroarylethynyl, $C_{1-6}$ alkylcarbonylamino, halo $C_{1-6}$ alkyl carbonylamino, optionally substituted $C_{3-7}$ cycloalkylcarbonylamino, optionally substituted heterocyclylcarbonylamino, optionally substituted phenylcarbonylamino and optionally substituted heteroarylcarbonylamino;

$R^1$, $R^2$, $R^3$ and $R^4$ when attached to a ring carbon atom, independently are selected from the group consisting of hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, hydroxy, $C_{1-6}$ alkoxy, halo $C_{1-6}$ alkoxy, heteroalkoxy, halogen, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl or amino optionally substituted by one or two substituents independently selected from $C_{1-6}$ alkyl, acyl, heteroalkyl, optionally substituted $C_{3-7}$ cycloalkyl and optionally substituted heterocyclyl, and or optionally substituted heterocyclyl, in which one of the ring carbon atoms of the heterocyclyl may be a ring carbon atom of another ring which is $C_{3-7}$ cycloalkyl or heterocyclyl, one or two ring carbon atoms of said another ring being optionally replaced by a carbonyl group; and when two of $R^1$, $R^2$, $R^3$ and $R^4$ are attached to the same ring carbon atom, they can, together with the carbon atom to which they are attached, form a $C_{3-7}$ cycloalkyl ring or heterocyclyl ring; or when attached to a ring nitrogen atom, $R^1$, $R^2$, $R^3$ and $R^4$ are independently hydrogen, $C_{1-6}$ alkyl, halo $C_{1-6}$ alkyl, heteroalkyl, $C_{2-6}$ alkenyl, $C_{2-6}$ alkynyl, hydroxy $C_{2-6}$ alkenyl, hydroxy $C_{2-6}$ alkynyl, $C_{1-6}$ alkoxy $C_{2-6}$ alkenyl, $C_{1-6}$ alkoxy $C_{2-6}$ alkynyl, optionally substituted $C_{3-7}$ cycloalkyl, or optionally substituted $C_{3-7}$ cycloalkyl $C_{1-6}$ alkyl, optionally substituted heterocyclyl or optionally substituted heterocyclyl-$C_{1-6}$ alkyl;

$R^5$ is hydrogen, $C_{1-6}$ alkyl, heteroalkyl, or optionally substituted $C_{3-7}$ cycloalkyl;

$R^6$ is hydrogen, $C_{1-6}$ alkyl, heteroalkyl or $C_{3-7}$ cycloalkyl;

provided that the compounds wherein Y is mono- or di-fluorosubstituted phenyl, mono- or di-methyl substituted phenyl, mono-chloro substituted phenyl, mono-methoxy substituted phenyl, mono-phenyl substituted phenyl, mono-chloro-mono-methyl substituted phenyl and mono-fluoro-mono-methoxy substituted phenyl are excluded;

or a pharmaceutically acceptable salt thereof
and a pharmaceutically acceptable excipient.

* * * * *